US007511058B2

(12) United States Patent
Hurley et al.

(10) Patent No.: US 7,511,058 B2
(45) Date of Patent: Mar. 31, 2009

(54) HETEROCYCLIC INHIBITORS OF MEK AND METHODS OF USE THEREOF

(75) Inventors: T. Brian Hurley, Boston, MA (US); Eli M. Wallace, Lyons, CO (US); Joseph P. Lyssikatos, Superior, CO (US); James Blake, Longmont, CO (US)

(73) Assignee: Array BioPharma Inc., Boulder, CO (US)

( * ) Notice: Subject to any disclaimer, the term of this patent is extended or adjusted under 35 U.S.C. 154(b) by 495 days.

(21) Appl. No.: 11/410,336

(22) Filed: Apr. 24, 2006

(65) Prior Publication Data

US 2006/0189808 A1   Aug. 24, 2006

Related U.S. Application Data

(62) Division of application No. 10/654,580, filed on Sep. 3, 2003, now Pat. No. 7,144,907.

(51) Int. Cl.
*A61K 31/437* (2006.01)
*C07D 471/02* (2006.01)

(52) U.S. Cl. ............... 514/303; 546/112; 546/113; 546/118; 546/119; 546/120; 514/299; 514/300

(58) Field of Classification Search ............. 546/112, 546/113, 118, 119, 120; 514/299, 300, 303
See application file for complete search history.

(56) References Cited

U.S. PATENT DOCUMENTS

| | | | |
|---|---|---|---|
| 5,919,807 | A | 7/1999 | Muller et al. |
| 6,221,850 | B1 | 4/2001 | McKay et al. |
| 6,310,060 | B1 | 10/2001 | Barrett et al. |
| 7,030,119 | B1 | 4/2006 | Barrett et al. |
| 7,144,907 | B2 * | 12/2006 | Wallace et al. ............ 514/379 |
| 7,230,099 | B2 * | 6/2007 | Wallace et al. ............ 544/127 |
| 7,271,178 | B2 * | 9/2007 | Wallace et al. ............ 514/300 |
| 2002/0052373 | A1 | 5/2002 | Zorn |
| 2003/0004193 | A1 | 1/2003 | Barrett et al. |
| 2003/0045521 | A1 | 3/2003 | Tecle |
| 2003/0078428 | A1 | 4/2003 | Barrett et al. |
| 2003/0092748 | A1 | 5/2003 | Barrett et al. |

FOREIGN PATENT DOCUMENTS

| | | |
|---|---|---|
| EP | 0602 242 | 6/1994 |
| WO | WO 99/01421 | 1/1999 |
| WO | WO 99/01426 | 1/1999 |
| WO | WO 00/41505 A2 | 7/2000 |
| WO | WO 00/41505 A3 | 7/2000 |
| WO | WO 00/42002 | 7/2000 |
| WO | WO 00/42003 | 7/2000 |
| WO | WO 00/42022 | 7/2000 |
| WO | WO 0041994 | 7/2000 |
| WO | WO 01/68619 | 9/2001 |
| WO | WO 02/06213 A2 | 1/2002 |
| WO | WO 02/06213 A3 | 1/2002 |

OTHER PUBLICATIONS

Rosenberger, et al. "Macrophages Inhibit *Salmonella typhimurium* Replication through MEK/ERK Kinase and Phagocyte NADPH Oxidase Activities"; J. Bio. Chem. May 2002; pp. 18753-18762; vol. 277, No. 21; US.
Russian Application No. 2006109599/04, Office Action (English Translation); Mar. 13, 2008.
Singapore Patent Application No. 200601338-7, Office Action; Jun. 19, 2008.

* cited by examiner

*Primary Examiner*—Golam M Shameem
(74) *Attorney, Agent, or Firm*—John R. Moore; Hogan & Hartson

(57) ABSTRACT

Disclosed are compounds of the Formula III

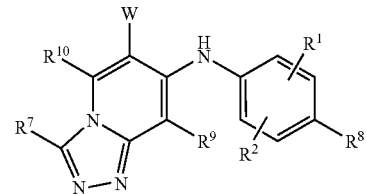

and pharmaceutically acceptable salts and prodrugs thereof, wherein $R^1$, $R^2$, $R^7$, $R^8$, $R^9$ $R^{10}$, and W are as defined in the specification. Such compounds are MEK inhibitors and useful in the treatment of hyperproliferative diseases, such as cancer and inflammation, in mammals. Also disclosed are methods of using such compounds in the treatment of hyperproliferative diseases in mammals and pharmaceutical compositions containing such compounds.

18 Claims, 18 Drawing Sheets

39

HCHO
(CF$_3$SO$_3$)$_3$Sc

33a

73a: W = Br, Y = Cl, X = H
73b: W = Br, Y = Cl, X = F

HETEROCYCLIC INHIBITORS OF MEK AND METHODS OF USE THEREOF

CROSS-REFERENCE TO RELATED APPLICATIONS

This application is a divisional application of U.S. application Ser. No. 10/654,580, which is incorporated herein by reference in its entirety.

BACKGROUND OF THE INVENTION

1. Field of the Invention

This invention relates to a series of novel heterocyclic compounds that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

2. Description of the State of the Art

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology*, 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology*, 2001, 332, 417-431). Phosphorylated ERK dimerizes and then translocates to the nucleus where it accumulates (Khokhlatchev et al., *Cell*, 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell*, 2000, 6, 1343-1354). Overall, treatment of cells with growth factors leads to the activation of ERK1 and 2 which results in proliferation and, in some cases, differentiation (Lewis et al., *Adv. Cancer Res.*, 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science*, 1993, 260, 1834-1837). Recently, bRaf mutations have been identified in more than 60% of malignant melanoma (Davies, H. et al., *Nature*, 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene*, 1999, 18, 813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al, *Nature-Medicine*, 1999, 5 (7), 810-816; Trachet et al., AACR Apr. 6-10, 2002, Poster #5426; Tecle, H., IBC 2$^{nd}$ International Conference of Protein Kinases, Sep. 9-10, 2002), block static allodynia in animals (WO 01/05390 published Jan. 25, 2001) and inhibit growth of acute myeloid leukemia cells (Milella et al., *J. Clin. Invest.*, 2001, 108 (6), 851-859).

Small molecule inhibitors of MEK have been disclosed. At least thirteen patent applications have appeared in the last several years: U.S. Pat. No. 5,525,625 filed Jan. 24, 1995; WO 98/43960 published Oct. 8, 1998; WO 99/01421 published Jan. 14, 1999; WO 99/01426 published Jan. 14, 1999; WO 00/41505 published Jul. 20, 2000; WO 00/42002 published Jul. 20, 2000; WO 00/42003 published Jul. 20, 2000; WO 00/41994 published Jul. 20, 2000; WO 00/42022 published Jul. 20, 2000; WO 00/42029 published Jul. 20, 2000; WO 00/68201 published Nov. 16, 2000; WO 01/68619 published Sep. 20, 2001; and WO 02/06213 published Jan. 24, 2002.

SUMMARY OF THE INVENTION

This invention provides for novel heterocyclic compounds, and pharmaceutically acceptable salts and prodrugs thereof that are useful in the treatment of hyperproliferative diseases. Specifically, one aspect of the present invention relates to compounds of Formula I that act as MEK inhibitors. Also provided is a method for treatment of cancer. Also provided are formulations containing compounds of Formula I and methods of using the compounds to treat a patient in need thereof. In addition, there are described processes for preparing the inhibitory compounds of Formula I.

Accordingly, the present invention provides compounds of the Formula I:

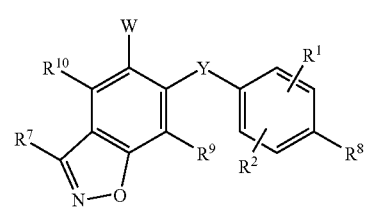

and pharmaceutically acceptable salts, prodrugs and solvates thereof, where:

$R^1$, $R^2$, $R^7$, $R^8$, $R^9$, and $R^{10}$ are independently hydrogen, halogen, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl;

R$^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate, or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted from oxo, halogen, cyano, nitro, trifluoromethyl, difluoromethoxy, trifluoromethoxy, azido, —NR'SO$_2$R"", —SO$_2$NR'R", —C(O)R', C(O)OR', —OC(O)R', —NR'C(O)OR"", —NR'C(O)R", —C(O)NR'R", —SR', —S(O)R"", —SO$_2$R"", —NR'R", —NR'C(O)NR"R''', —NR'C(NCN)NR"R''', —OR', aryl, heteroaryl, arylalkyl, heteroarylalkyl, heterocyclyl, and heterocyclylalkyl, or R$^3$ and R$^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR'SO$_2$R"", —SO$_2$NR'R", —C(O)R', —C(O)OR', —OC(O)R', —NR'C(O)OR"", —NR'C(O)R", —C(O)NR'R", —SO$_2$R"", —NR'R", —NR'C(O)NR"R''', —NR'C(NCN)NR"R''', —OR', aryl, heteroaryl, arylalkyl, heteroarylalkyl, heterocyclyl, and heterocyclylalkyl;

R', R" and R''' independently are hydrogen, lower alkyl, lower alkenyl, aryl and arylalkyl, and R"" is lower alkyl, lower alkenyl, aryl and arylalkyl, or any two of R', R", R''' or R"" together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

R$^4$ and R$^5$ independently are hydrogen or $C_1$-$C_6$ alkyl, or R$^4$ and R$^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR'SO$_2$R"", —SO$_2$NR'R", —C(O)R"", —C(O)OR', —OC(O)R', —NR'C(O)OR"", —NR'C(O)R", —C(O)NR'R", —SO$_2$R"", —NR'R", —NR'C(O)NR"R''', —NR'C(NCN)NR"R''', —OR', aryl, heteroaryl, arylalkyl, heteroarylalkyl, heterocyclyl, and heterocyclylalkyl;

R$^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO$_2$R"", —SO$_2$NR'R", —C(O)R', —C(O)OR', —OC(O)R', —NR'C(O)OR"", —NR'C(O)R", —C(O)NR'R", —SO$_2$R"", —NR'R", —NR'C(O)NR"R''', —NR'C(NCN)NR"R''', —OR', aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)($C_3$-$C_{10}$ cycloalkyl), —C(O)($C_1$-$C_{10}$ alkyl), —C(O)(aryl), —C(O)(heteroaryl), —C(O)(heterocyclyl) or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)($C_3$-$C_{10}$ cycloalkyl), —C(O)($C_1$-$C_{10}$ alkyl) —C(O)(aryl), —C(O)(heteroaryl), —C(O)(heterocyclyl), and CR$^3$OR$^3$ are optionally substituted with one or more groups independently selected from —NR$^3$R$^4$, —OR$^3$, —R$^2$, $C_1$-$C_{10}$ alkyl, $C_2$-$C_{10}$ alkenyl, and $C_2$-$C_{10}$ alkynyl, wherein any of said $C_1$-$C_{10}$ alkyl, $C_2$-$C_{10}$ alkenyl, and $C_2$-$C_{10}$ alkynyl are optionally substituted with 1 or more groups independently selected from —NR$^3$R$^4$ and —OR$^3$;

m is 0, 1, 2, 3, 4 or 5;

j is 1 or 2; and

Y is a linker.

In another embodiment, this invention relates to compounds of the general Formula II:

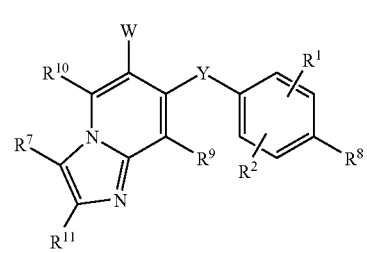

II where R$^1$, R$^2$, R$^3$, R$^4$, R$^5$, R$^6$, R$^7$, R$^8$, R$^9$, R$^{10}$, R', R", R''', R"", W, Y, m and j are as defined above, and R$^{11}$ is hydrogen, halogen, cyano, nitro, trifluoromethyl, difluoromethoxy, trifluoromethoxy, azido, —OR$^3$, —C(O)R$^3$, —C(O)OR$^3$, NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl.

In another embodiment, this invention relates to compounds of the general Formula III:

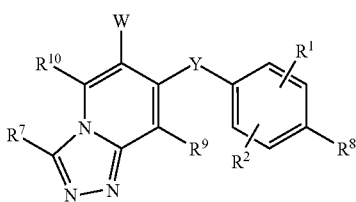

III where $R^1$, $R^2$, $R^3$, $R^4$, $R^5$, $R^6$, $R^7$, $R^8$, $R^9$, $R^{10}$, R', R'', R''', R'''', W, Y, m and j are as defined above.

In another embodiment, this invention relates to compounds of the general Formula IV:

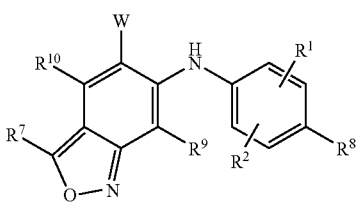

IV where $R^1$, $R^2$, $R^3$, $R^4$, $R^5$, $R^6$, $R^7$, $R^8$, $R^9$, $R^{10}$, R', R'', R''', R'''', W, Y m and j are as defined above.

In another embodiment, this invention relates to compounds of the general Formula V:

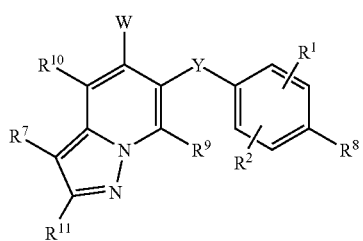

V where $R^1$, $R^2$, $R^3$, $R^4$, $R^5$, $R^6$, $R^7$, $R^8$, $R^9$, $R^{10}$, R', R'', R''', R'''', W, Y, m and j are as defined above.

In a further aspect the present invention provides compositions that inhibit MEK comprising compounds of Formulas I-V.

The invention is also directed to pharmaceutically acceptable prodrugs, pharmaceutically active metabolites, and pharmaceutically acceptable salts of compounds of Formula I-V. Methods of making the compounds of Formula I-V are also described.

In a further aspect the present invention provides a method of using the compounds of this invention to treat diseases or medical conditions mediated by MEK. For example, this invention provides a method for treatment of a hyperproliferative disorder in a mammal comprising administrating to said mammal one or more compounds of Formulas I-V or a pharmaceutically acceptable salt or prodrug thereof in an amount effective to treat said hyperproliferative disorder.

In a further aspect the present invention provides treating or preventing an MEK-mediated condition, comprising administering to a human or animal in need thereof a pharmaceutical composition comprising a compound of Formula I-V or a pharmaceutically-acceptable salt or in vivo cleavable prodrug thereof in an amount effective to treat or prevent said MEK-mediated condition.

The inventive compounds may further be used advantageously in combination with other known therapeutic agents.

The invention also relates to pharmaceutical compositions comprising an effective amount of an agent selected from compounds of Formulas I-V or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures:

FIG. 1 shows a reaction scheme for the synthesis of compound 10a.

FIG. 2 shows a reaction scheme for the synthesis of compound 12a.

FIG. 3 shows a reaction scheme for the synthesis of compound 13a.

FIG. 9 shows a reaction scheme for the synthesis of compound 33a.

FIG. 14 shows a reaction scheme for the synthesis of compounds 53a, 53b and 54a.

DETAILED DESCRIPTION OF THE INVENTION

Figure 1:
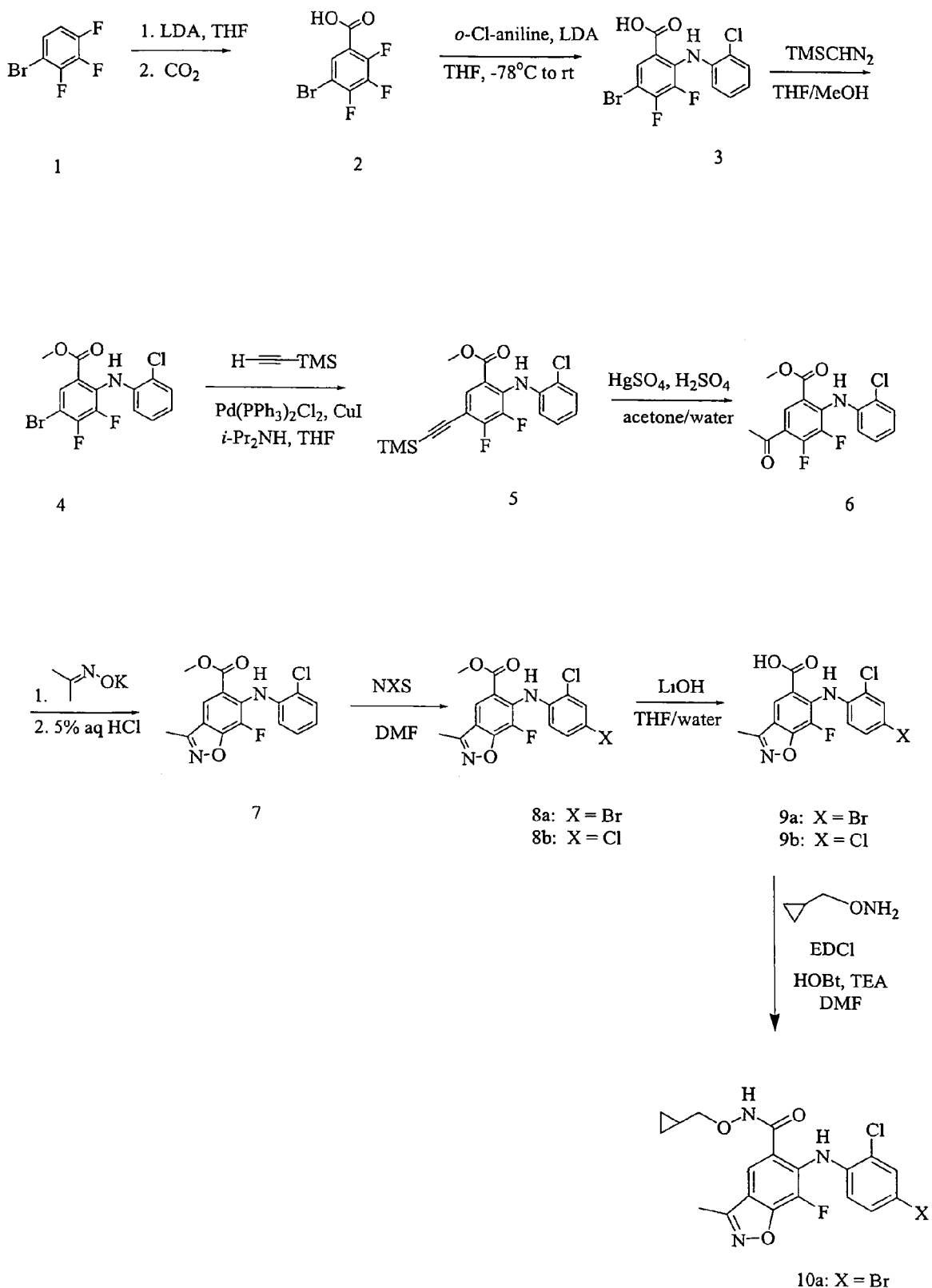

The inventive compounds of the Formulas I-V and the pharmaceutically acceptable salts and prodrugs thereof of this invention are useful in the treatment of hyperproliferative diseases. Specifically, one aspect the present invention relates to compounds of Formula I-V that act as MEK inhibitors. In general, one aspect of the invention relates to compounds having the general Formula I:

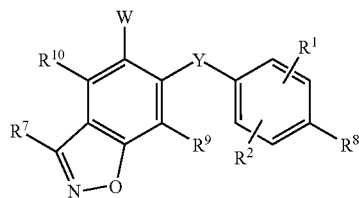

I and pharmaceutically acceptable salts, prodrugs and solvates thereof, where:

$R^1$, $R^2$, $R^7$, $R^8$, $R^9$, and $R^{10}$ are independently hydrogen, halogen, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)N^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate, or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO$_2$R'''', —SO$_2$NR'R'', —C(O)R', C(O)OR', —OC(O)R', —NR'C(O)OR'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O) NR'R'', —SO$_2$R'''', —NR'R'', —NR'C(O)NR''R''', —NR'C(NCN)NR''R''', —OR, aryl, arylalkyl, heteroarylalkyl, heterocyclyl and heterocyclylalkyl;

R', R'' and R''' independently are hydrogen, lower alkyl, lower alkenyl, aryl and arylalkyl, and R'''' is lower alkyl, lower alkenyl, aryl and arylalkyl, or any two of R', R'', R''' or R'''' together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl, heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O) (heteroaryl), —C(O)(heterocyclyl) or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O) (heteroaryl), —C(O)(heterocyclyl), and CR$^3$OR$^3$ are optionally substituted with one or more groups independently selected from —NR$^3$R$^4$, —OR$^3$, —R$^2$, C$_1$-C$_{10}$ alkyl, C$_2$-C$_{10}$ alkenyl, and C$_2$-C$_{10}$ alkynyl, wherein any of said C$_1$-C$_{10}$ alkyl, C$_2$-C$_{10}$ alkenyl, and C$_2$-C$_{10}$ alkynyl are optionally substituted with 1 or more groups independently selected from —NR$^3$R$^4$ and —OR$^3$;

m is 0, 1, 2, 3, 4 or 5;

j is 1 or 2; and

Y is a linker.

A "linker" is a molecular entity that connects two or more molecular entities through covalent or non-covalent interactions. Examples of linkers include, but are not limited to, NR$^3$, O, S, S(O), S(O)$_2$, C(O), and CH$_2$, where R$^3$ is as defined above.

FIGS. 1-6 show non-limiting examples of the synthesis of compounds of this invention having the general Formula I.

In addition to compounds of the general Formula I, this invention further includes compounds of the general Formula II:

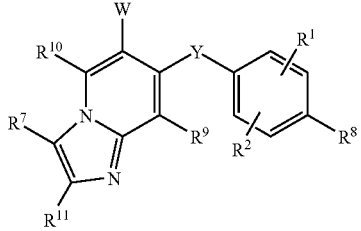

where $R^1$, $R^2$, $R^3$, $R^4$, $R^5$, $R^6$, $R^7$, $R^8$, $R^9$, $R^{10}$, R', R'', R''', R'''', W, Y, m and j are as defined above, and $R^{11}$ is hydrogen, halogen, cyano, nitro, trifluoromethyl, difluoromethoxy, trifluoromethoxy, azido, —$OR^3$, —C(O)$R^3$, —C(O)$OR^3$, $NR^4$C(O)$OR^6$, —OC(O)$R^3$, —$NR^4SO_2R^6$, —$SO_2NR^3R^4$, —$NR^4$C(O)$R^3$, —C(O)$NR^3R^4$, —$NR^5$C(O)$NR^3R^4$, —$NR^5$C(NCN)$NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^4SO_2R^6$, —$SO_2NR^3R^4$, —C(O)$R^3$, —C(O)$OR^3$, —OC(O)$R^3$, —$NR^4$C(O)$OR^6$, —$NR^4$C(O)$R^3$, —C(O)$NR^3R^4$, —$NR^3R^4$, —$NR^5$C(O)$NR^3R^4$, —$NR^5$C(NCN)$NR^3R^4$, —$OR^3$, aryl, heteroaryl, arylalkyl, heteroarylalkyl, heterocyclyl, and heterocyclylalkyl.

Figure 18:
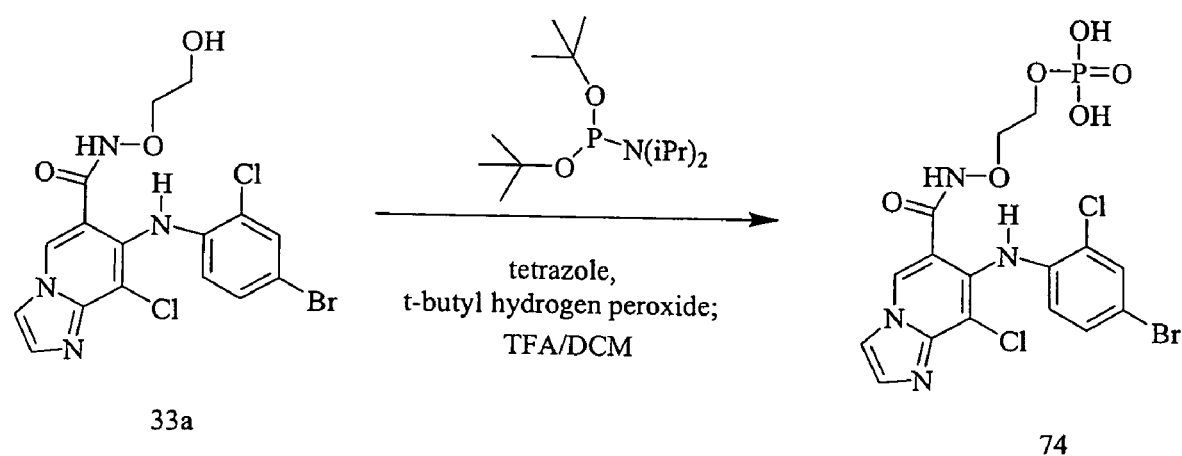
FIG. 18 shows a reaction scheme for the synthesis of compound 74.

FIGS. 7-13 show non-limiting examples of the synthesis of compounds of this invention having the general Formula II. FIG. 18 shows the synthesis of a phosphate prodrug of a compound having the general Formula II.

In another embodiment, this invention relates to compounds of the general Formula III:

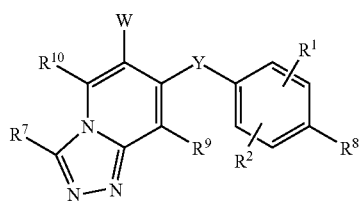

where $R^1$, $R^2$, $R^3$, $R^4$, $R^5$, $R^6$, $R^7$, $R^8$, $R^9$, $R^{10}$, R', R'', R''', R'''', W, Y, m and j are as defined above.

Figure 14:
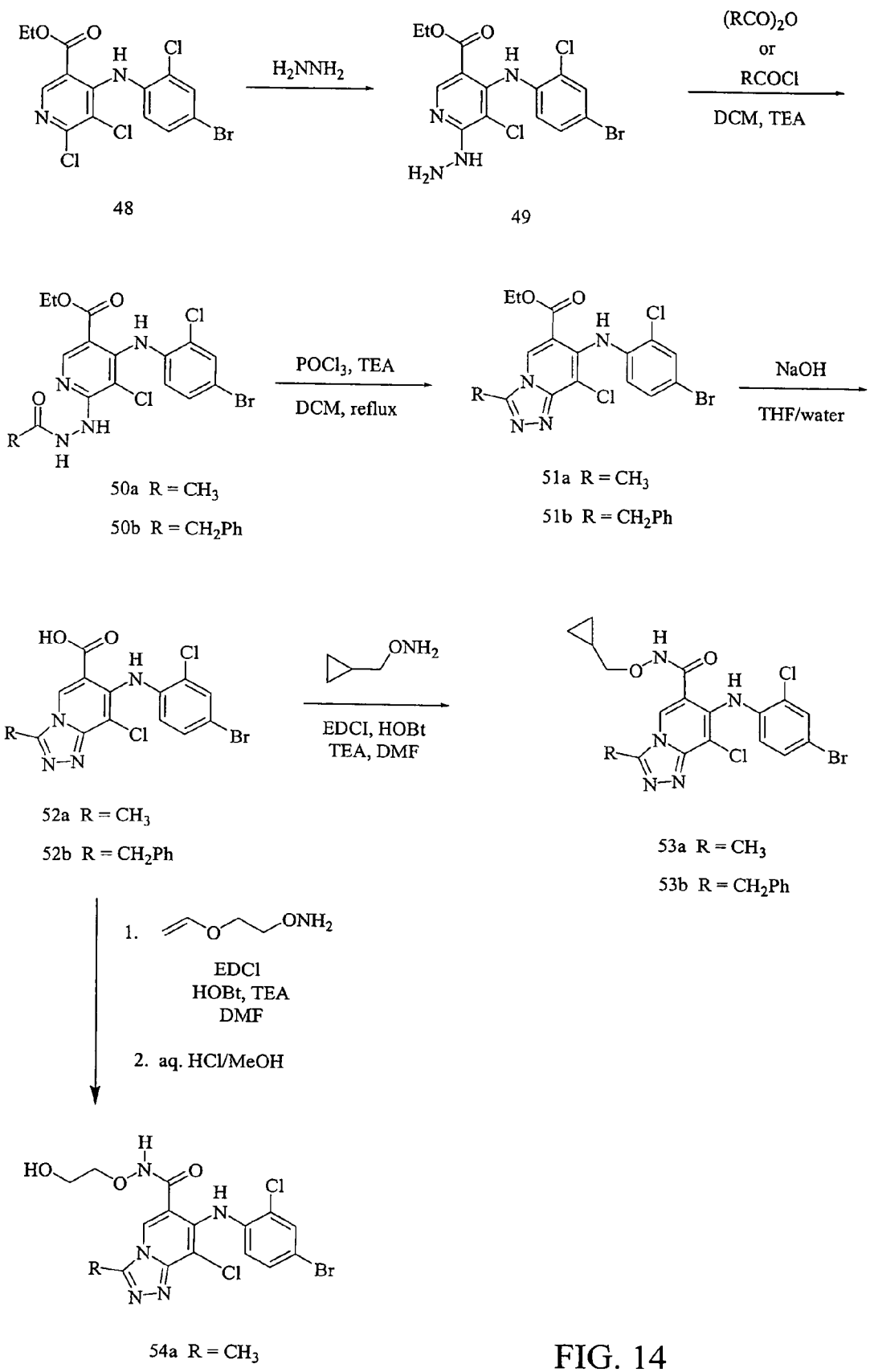

FIG. 14 shows a non-limiting example of the synthesis of compounds of this invention having the general Formula III.

In another embodiment, this invention relates to compounds of the general Formula IV:

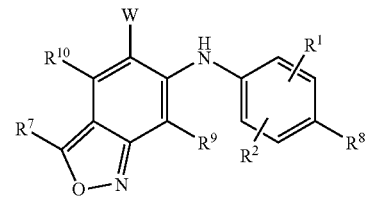

where $R^1$, $R^2$, $R^3$, $R^4$, $R^5$, $R^6$, $R^7$, $R^8$, $R^9$, $R^{10}$, R', R'', R''', R'''', W, Y, m and j are as defined above.

Figure 15:
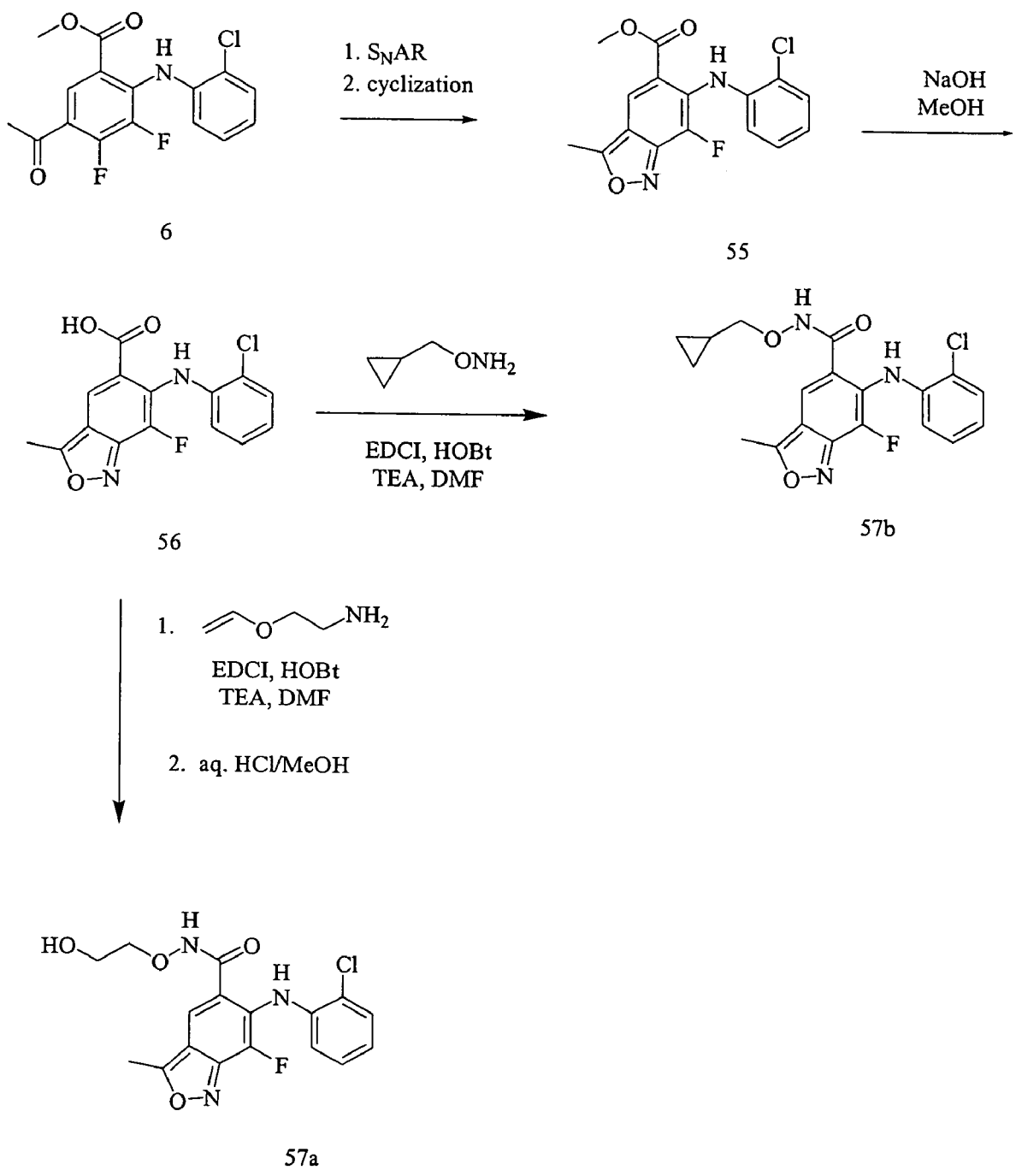
FIG. 15 shows a reaction scheme for the synthesis of compounds 57a and 57b.

FIG. 15 shows a non-limiting example of the synthesis of compounds of this invention having the general Formula IV.

Figure 16:
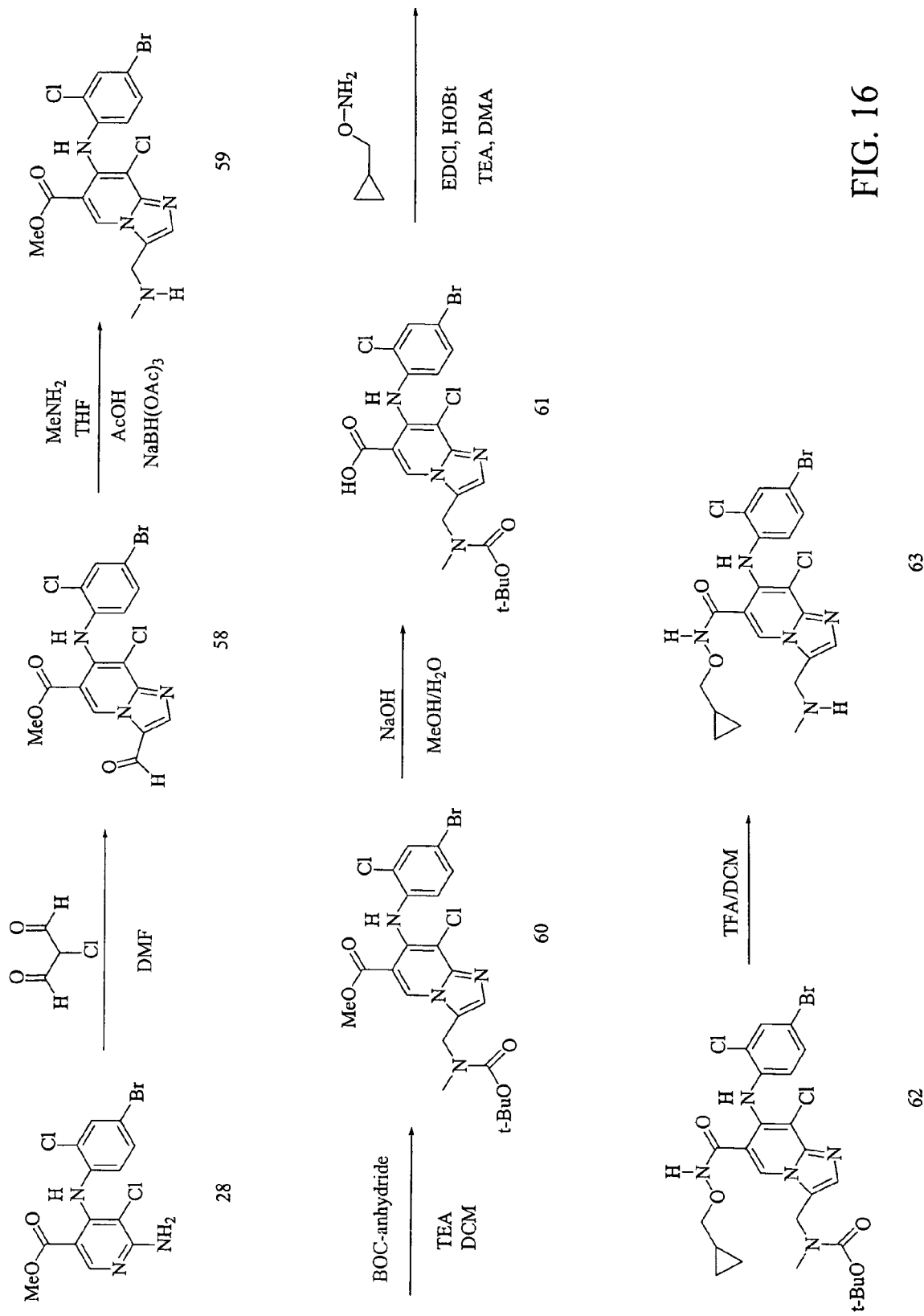
FIG. 16 shows a reaction scheme for the synthesis of compound 63.
Figure 17:
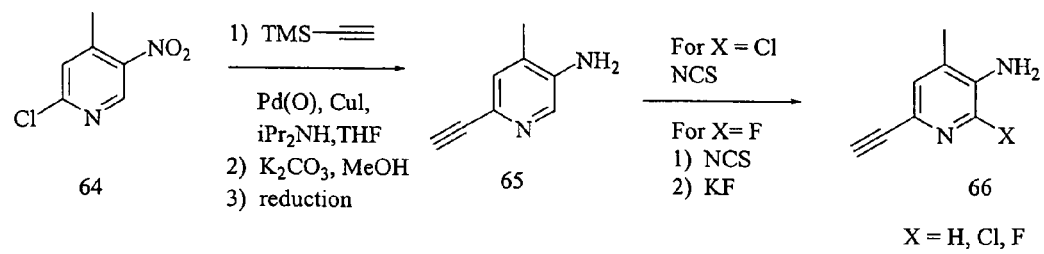
FIG. 17 shows a reaction scheme for the synthesis of compounds 73a and 73b.
Figure 17:
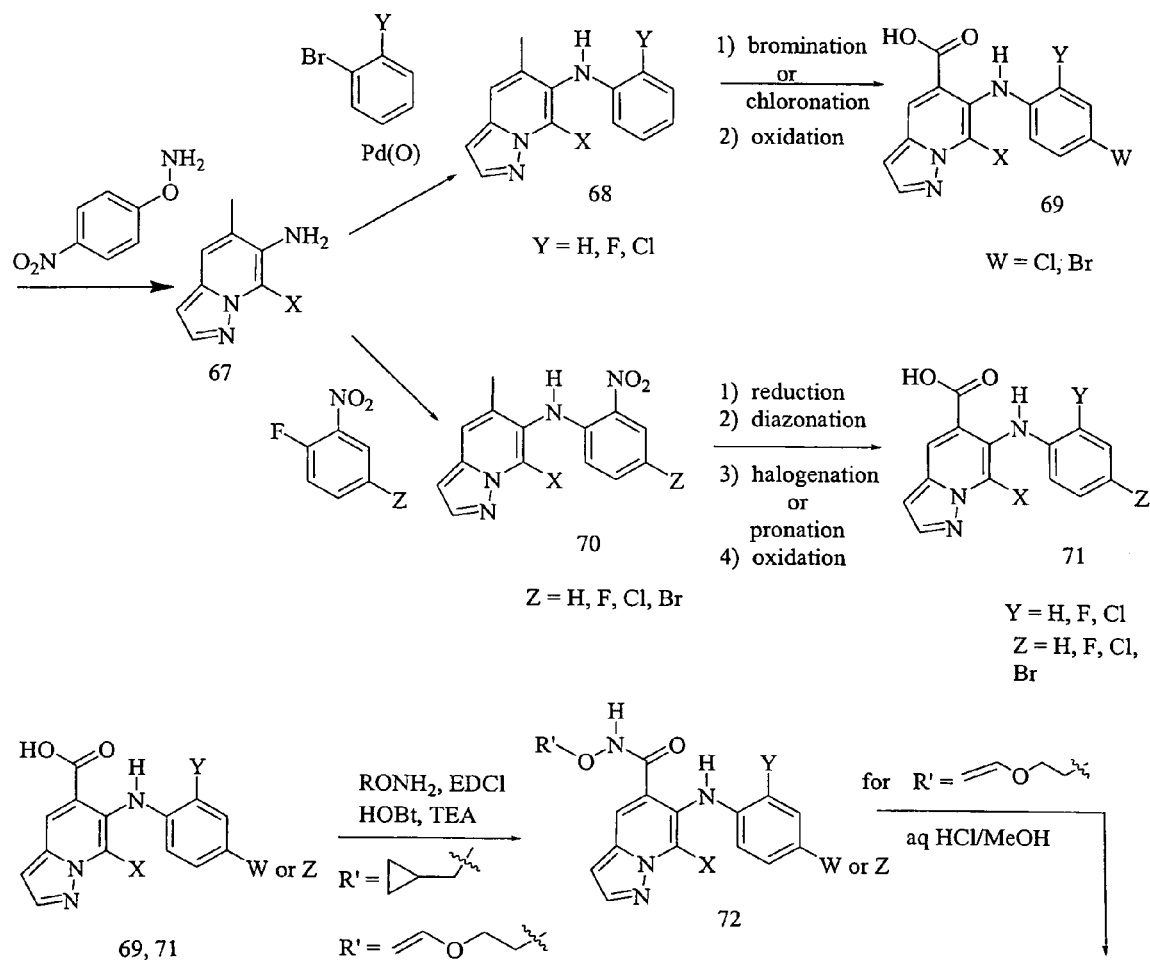
Figure 17:
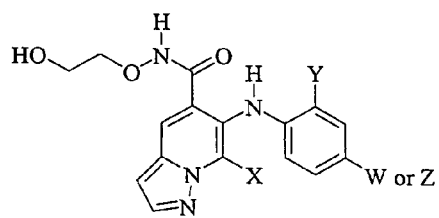

In another embodiment, this invention relates to compounds of the general Formula V:

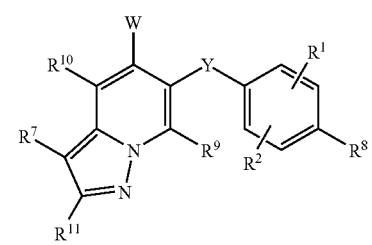

where $R^1$, $R^2$, $R^3$, $R^4$, $R^5$, $R^6$, $R^7$, $R^8$, $R^9$, $R^{10}$, $R^{11}$, R', R'', R''', R'''', W, Y, m and j are as defined above. FIGS. 16-17 show non-limiting examples of the synthesis of compounds of this invention having the general Formula V.

The terms "$C_1$-$C_{10}$ alkyl", "alkyl" and "lower alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "$C_2$-$C_{10}$ alkenyl", "lower alkenyl" and "alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "$C_2$-$C_{10}$ alkynyl," "lower alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "allyl" refers to a radical having the formula RC═CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The terms "carbocycle," "carbocyclyl," "cycloalkyl" or "$C_3$-$C_{10}$ cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "hetercyclyl" refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2, 3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$) alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

The term "halogen" represents fluorine, bromine, chlorine, and iodine.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

In general, the various moieties or functional groups of the compounds of Formulas I-V may be optionally substituted by one or more substituents. Examples of substituents suitable for purposes of this invention include, but are not limited to, oxo, halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, where $R^3$, $R^4$, $R^5$ and $R^6$ are as defined herein.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the compounds of the present invention, where terms such as $(CR^4R^5)_m$ or $(CR^4R^5)_t$ are used, $R^4$ and $R^5$ may vary with each iteration of m or t above 1. For instance, where m or t is 2, the terms $(CR^4R^5)_m$ or $(CR^4R^5)_t$ may equal —CH$_2$CH$_2$— or —CH(CH$_3$)C(CH$_2$CH$_3$)(CH$_2$CH$_2$CH$_3$)— or any number of similar moieties falling within the scope of the definitions of $R^4$ and $R^5$.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and pure enantiomers of the Formulas I-V. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

This invention also encompasses pharmaceutical compositions containing a compound of Formula I-V and methods of treating proliferative disorders, or abnormal cell growth, by administering compounds of the present invention. Compounds of the present invention having free amino, amido, hydroxy or carboxylic groups can be converted into pharmaceutically acceptable prodrugs.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of Formula I-V covalently joined to a phosphate residue. Another preferred prodrug of this invention is a compound of Formula I-V covalently joined to a valine residue.

Additional types of prodrugs are also encompassed. For instance, free carboxyl groups can be derivatized as amides or alkyl esters. Free hydroxy groups may be derivatized using groups including but not limited to phosphate esters, hemisuccinates, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.,* 1996, 39, 10. Free amines can also be derivatized as amides, sulfonamides or phosphonamides. All of these prodrug moieties may incorporate groups including but not limited to ether, amine and carboxylic acid functionalities.

In addition, the invention also includes solvates, pharmaceutically active metabolites, and pharmaceutically acceptable salts of compounds of Formulas I-V.

The term "solvate" refers to an aggregate of a molecule with one or more solvent molecules.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs,* edited by H. Bundgaard, (Elsevier, 1985) and *Methods in Enzymology,* Vol. 42, p. 309-396, edited by K. Widder, et al. (Academic Press, 1985); b) *A Textbook of Drug Design and Development,* edited by Krogsgaard-Larsen and H. Bundgaard, Chapter 5 *"Design and Application of Prodrugs,"* by H. Bundgaard p. 113-191 (1991); c) H. Bundgaard, *Advanced Drug Delivery Reviews,* 8, 1-38 (1992); d) H. Bundgaard, et al., *Journal of Pharmaceutical Sciences,* 77:285 (1988); and e) N. Kakeya, et al., *Chem. Pharm. Bull.,* 32: 692 (1984), each of which is specifically incorporated herein by reference.

A "pharmaceutically acceptable salt" as used herein, unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

The inventive compounds may be prepared using the reaction routes and synthesis schemes as described below, employing the techniques available in the art using starting materials that are readily available or can be synthesized using methods known in the art.

Illustrations of the preparation of compounds of the present invention are shown in Schemes 1-11.

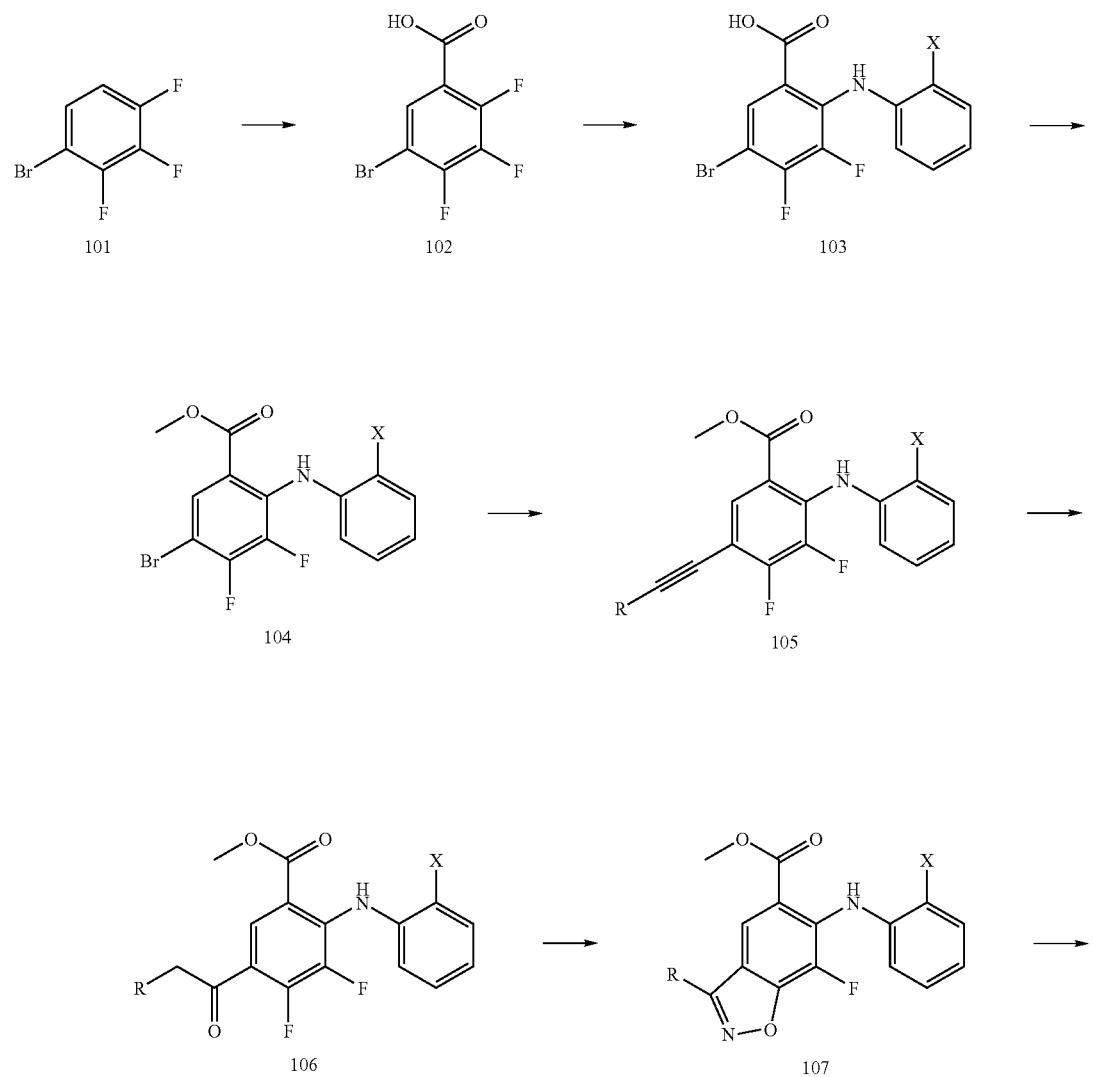

-continued
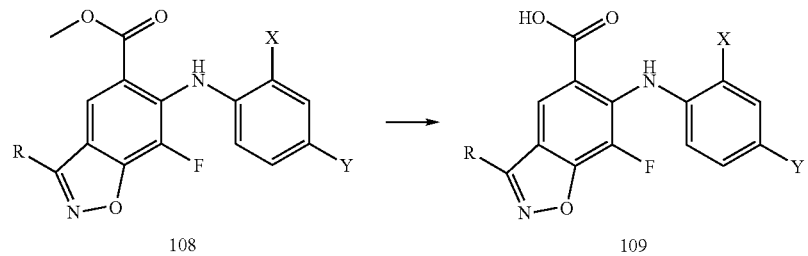
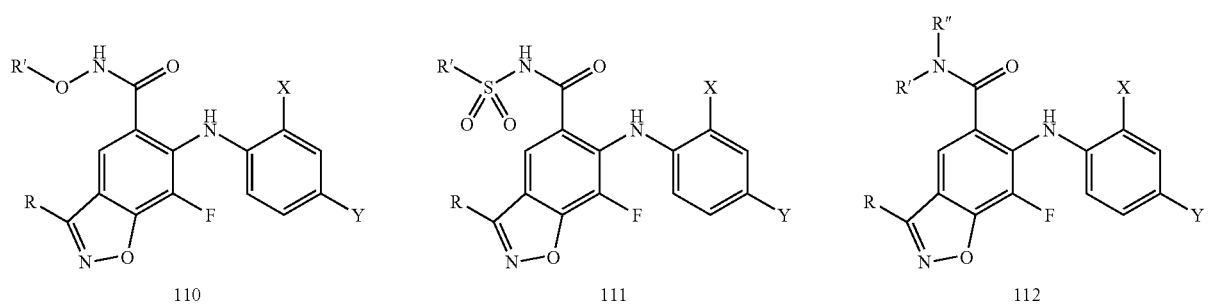
SCHEME 2
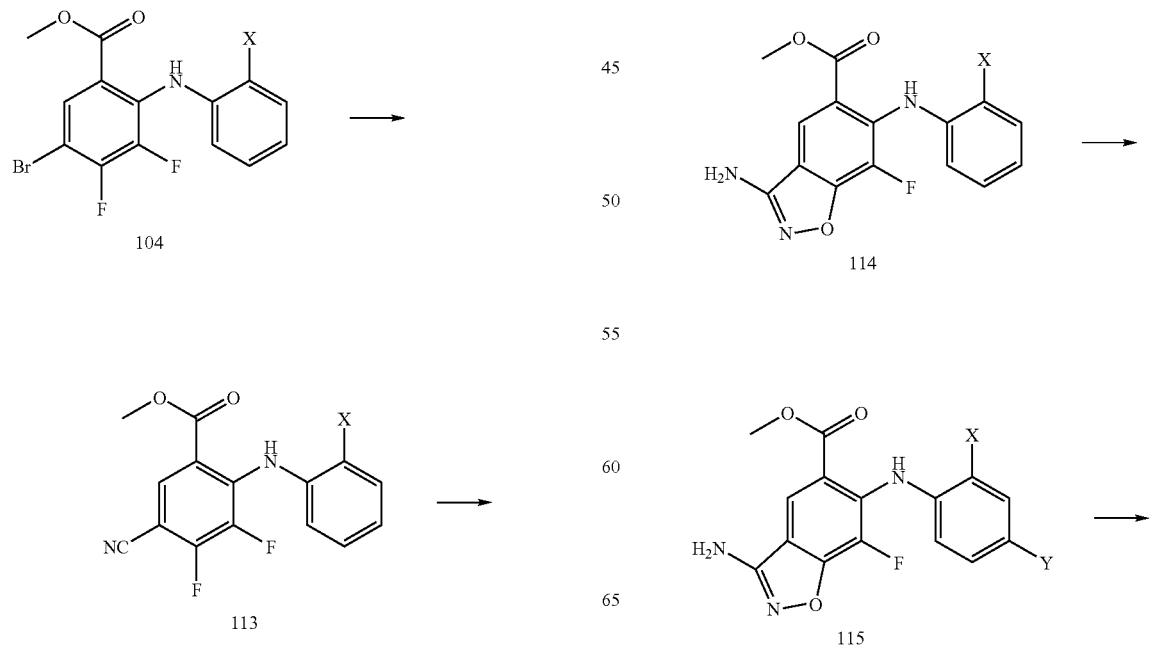

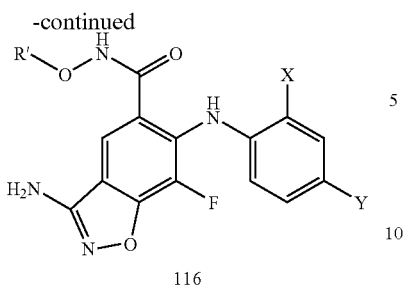
116
SCHEME 3
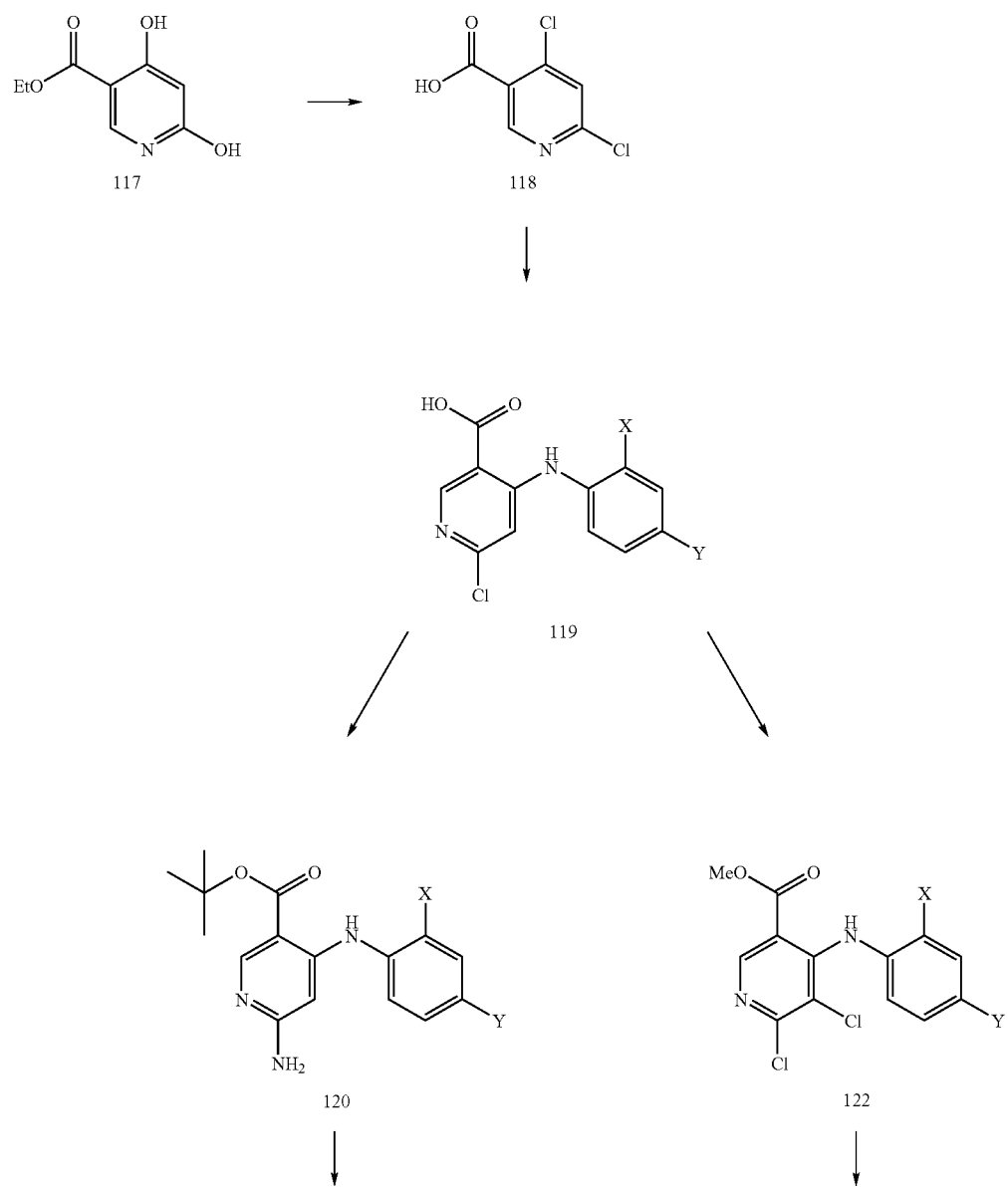

21
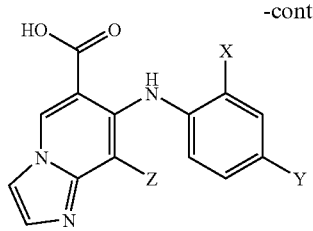
121
22
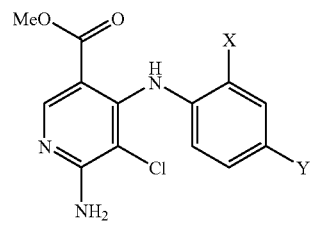
123
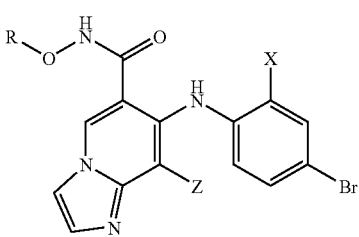
125
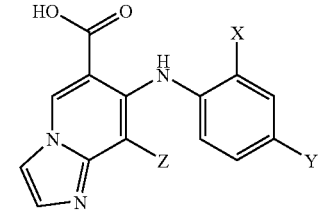
124
SCHEME 4
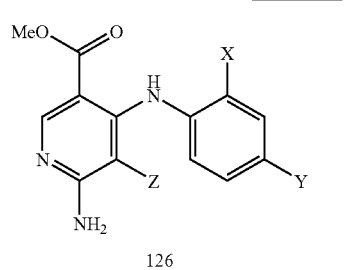
126
+
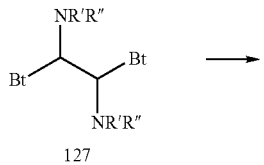
127
-continued
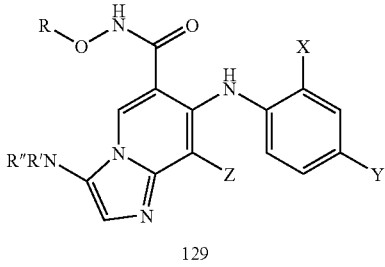
129
Bt = benzotriazole
SCHEME 5
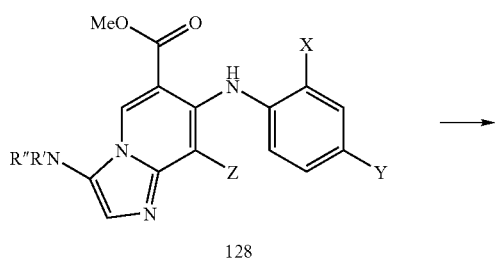
128
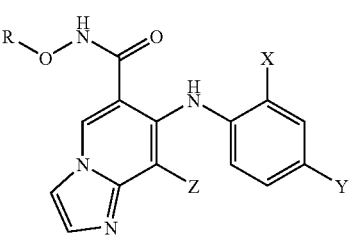
130

-continued
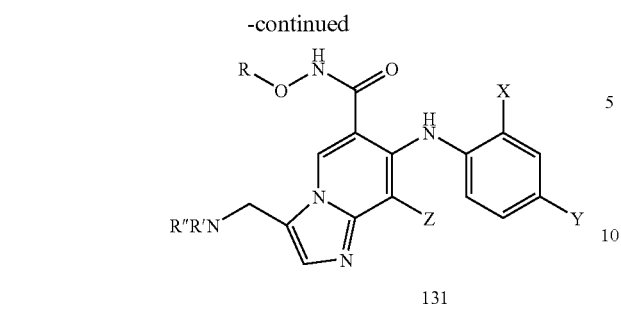
131
SCHEME 6
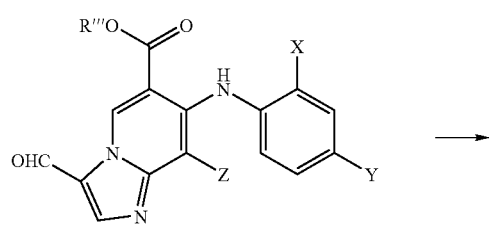
132
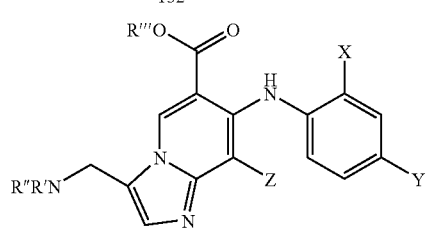
133
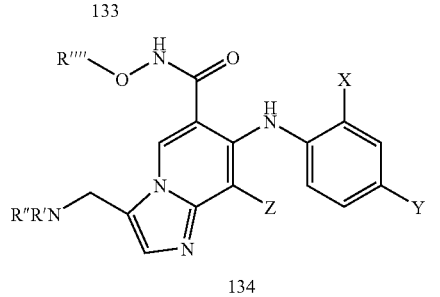
134
SCHEME 7
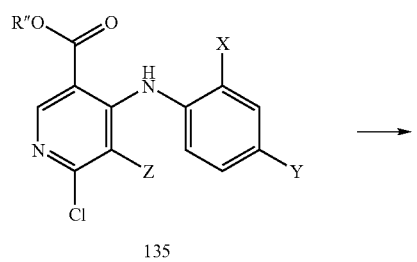
135
-continued
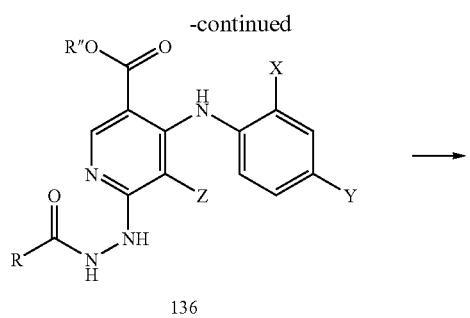
136
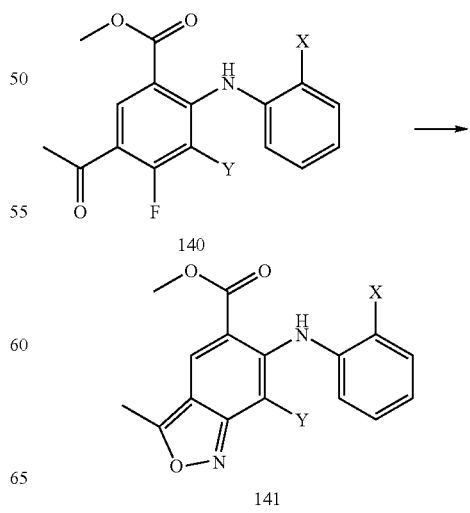
137
138
139
SCHEME 8
140
141

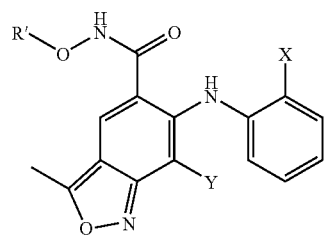

142

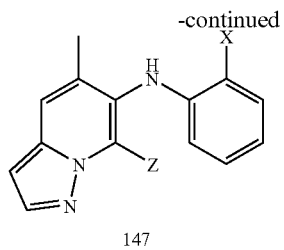

147

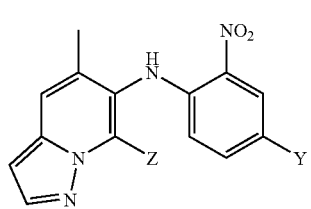

148

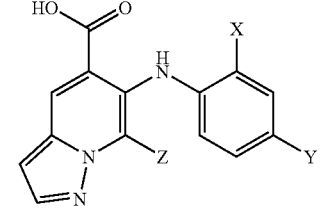

149

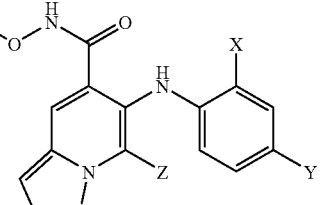

150

SCHEME 9

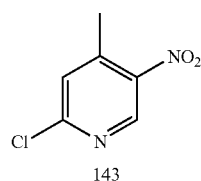

143

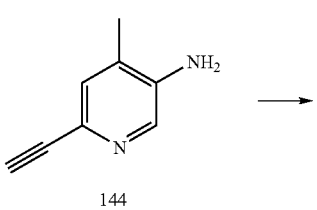

144

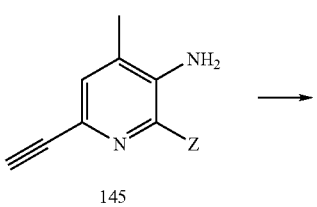

145

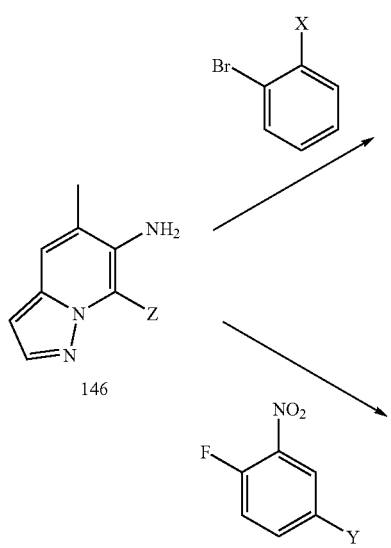

146

Scheme 1 illustrates one method of preparing compounds of the Formula I. Carboxylic acid 102 can be prepared from arene 101 by deprotonation at low temperature (−100 to −60° C.) in the appropriate ethereal solvent such as THF or diethyl ether followed by carbon dioxide quench, which can be performed with solid dry ice. The deprotonation can be accomplished with LDA in THF at −78° C. One quench method comprises adding the aryllithium THF solution via cannula to a saturated solution of dry carbon dioxide in THF at −78° C. and then warming to room temperature. Aniline 103 can be prepared by deprotonation of an appropriate 2-substituted aniline with KHMDS, LiHMDS, NaHMDS or LDA at low temperature (−100 to −60° C.) in an appropriate ethereal solvent such as THF or diethyl ether, followed by addition of carboxylic acid 102 and warming to room temperature. In one embodiment, deprotonation is accomplished with LDA at −78° C. in THF, followed by addition of carboxylic acid 102 and warming to room temperature. Ester 104 can be prepared by standard methods including, but not limited to, Fisher esterification (MeOH, $H_2SO_4$), reaction with $TMSCHN_2$ or TMSCl in MeOH. Acetylene derivative 105 is prepared by Sonagashria coupling of bromide 104 using an appropriately substituted acetylene, CuI, an amine base, palladium catalyst and organic solvent such as DME, THF, or DMF at temperatures between 25 and 100° C. Suitable palladium catalysts include, but are not limited to, PdCl$_2$(dppf), Pd(Ph$_3$P)$_4$, and Pd$_2$dba$_3$/dppf. Suitable amine bases include, but are not limited to, Et$_3$N, Hunig's base, and diisopropyl amine. In one embodiment, the Pd(0) mediated coupling to prepare acetylene 105 is accomplished with Pd(PPh$_3$)$_2$Cl$_2$, CuI, diisopropyl amine, and the appropriate substituted acetylene in THF at room temperature. Hydrolysis of acetylene 105 to prepare ketone 106 can be accomplished by standard methods including but not limited to H$_2$SO$_4$, TFA, trifluorosulfonamide, FeCl$_3$, or HgSO$_4$/H$_2$SO$_4$. Benzisoxazole 107 can be prepared in a two step procedure from ketone 106. Addition of the potassium salt of acetone oxime in suitable organic solvent such as THF or Et$_2$O at temperatures ranging from −78 to 5° C. is followed by acid catalyzed cyclization. The acetone oxime addition is most easily performed by addition of a THF solution of ketone 106 to the salt at 0° C. The cyclization can be accomplished with a variety of acidic aqueous conditions at a range of temperatures. In one embodiment cyclization is accomplished by treatment of the isopropylideneaminooxybenzoic acid methyl ester with 5% aqueous HCl in MeOH at reflux. Halogenation to form benzisoxazole 108 is accomplished using standard procedures such as NCS or NBS in DMF. Hydrolysis of ester 108 to form carboxylic acid 109 can be performed under standard conditions. The acid can be converted to hydroxamate 110 or amide 112 by standard coupling procedures including but not limited to EDCI/HOBt, PyBOP, or DIC and the appropriate hydroxyl amine or amine. Alternatively, hydroxamate 110 or amide 112 can be prepared in two steps by initial conversion to the acid chloride by standard methods followed by addition of the hydroxyl amine or amine. Acyl sulfonamide 111 can be synthesized by preparing an activated ester of carboxylic acid 109 followed by treatment with the appropriate sulfonamide and tertiary amine base in a suitable organic solvent such as THF. In one embodiment, acyl sulfonamide 111 is prepared by treatment of carboxylic acid 109 with CDI at elevated temperature (50° C.) in THF followed treatment with the appropriate sulfonamide and DBU.

Scheme 2 illustrates an alternative method for synthesizing compounds of the Formula I. Nitrile 113 can be prepared by palladium mediated coupling of bromide 104 with zinc cyanide in suitable organic solvent such as DMA, NMP or DMF at elevated temperatures ranging from 50 to 120° C. Several palladium catalysts may be employed including but not limited to Pd(PPh$_3$)$_4$, PdCl$_2$(dppf), or Pd$_2$dba$_3$ with ligands such as dppe, dppp, dppf or BINAP. In one embodiment, nitrile 113 is prepared from bromide 104 by treatment with zinc cyanide, Pd$_2$dba$_3$, and dppf in NMP at 120° C. Amino benzisoxazole 114 can be prepared in a two step procedure from nitrile 113 by the addition of the potassium salt of acetone oxime in suitable organic solvent such as THF or Et$_2$O at temperatures ranging from −78 to 5° C. followed by acid catalyzed cyclization. In one embodiment the acetone oxime addition can be performed by addition of a THF solution of nitrile 113 to the salt at 0° C. in THF followed by warming to room temperature. The cyclization can be accomplished under a variety of acidic conditions at a range of temperatures. In one embodiment the cyclization method comprises treatment of the oxime addition product in MeOH with 2 M HCl in Et$_2$O. Halogenation to form benzisoxazole 115 is accomplished using standard procedures such as NCS or NBS in DMF. Compound 116 is prepared in a two step procedure comprising hydrolysis of ester 115 under standard conditions to form the corresponding carboxylic acid, followed by conversion of the carboxylic acid to hydroxamate 116 by standard coupling procedures, including but not limited to, EDCI/HOBt, PyBOP, or DIC and the appropriate hydroxyl amine.

Scheme 3 illustrates one method of synthesizing compounds of the Formula II. 4,6-Dichloronicotinic acid 118 can be prepared from 4,6-dihydroxynicotinic acid ethyl ester 117 in two steps. In the first step, 4,6-dihydroxynicotinic acid ethyl ester 117 is chlorinated using an appropriate reagent such as POCl$_3$, oxalyl chloride or thionyl chloride. In one embodiment, chlorination is accomplished with POCl$_3$ and Et$_3$N at elevated temperatures. Hydrolysis of the resulting dichloroethyl ester to provide compound 118 can be performed under standard conditions. Aniline 119 can be prepared by deprotonation of the properly substituted aniline with KHMDS, LiHMDS, NaHMDS or LDA at low temperature (−100 to −60° C.) in appropriate ethereal solvent such as THF or diethyl ether followed by addition of carboxylic acid 118 and warming to room temperature. In one embodiment, deprotonation is accomplished with LiHMDS at −78° C. in THF, followed by addition of carboxylic acid 118 and warming to room temperature. Amino pyridine 120 is prepared in three steps from aniline 119. In the first step, the tert-butyl ester is prepared by treating the acid 119 with 2-tert-butyl-1,3-diisopropylisourea in THF at temperatures ranging from 25 to 75° C. In the second step, sodium azide is added to the tert-butyl ester in DMF at 80° C. The amino pyridine 120 is prepared by reduction of the azide under standard conditions including but not limited to Zn dust/AcOH, Pt/C or PtO$_2$ in the presence of H$_2$ gas, Ph$_3$P or SnCl$_2$/MeOH. In one embodiment, the azide reduction is accomplished by treatment with Zn dust in a mixture of methylene chloride and acetic acid. Imidazopyridine 121 where Z=F is prepared in two steps from amino pyridine 120. In the first step, fluorination is accomplished by treatment of the amino pyridine 120 with SELECTFLUOR™ in a mixture of MeOH and water or pH 7 phosphate buffer. Cyclization to form imidazopyridine 121 (Z=H or F) can be accomplished by treatment with chloro or bromo acetaldehyde in suitable organic solvent such as DMF or EtOH at elevated temperatures (50 to 120° C.). In one embodiment, cyclization is realized by treatment with chloroacetaldehyde in EtOH at 70° C. Alternatively, aniline 119 can be converted to dichloroester 122 in two steps. In the first step, chlorination is performed under standard conditions such as NCS in DMF. In the second step, esterification can be achieved by standard methods including but not limited to Fisher esterification (MeOH, H$_2$SO$_4$), reaction with TMSCHN$_2$ or TMSCl in MeOH. Aminopyridine 123 can be prepared as described above for aminopyridine 120 with the exception that the sodium azide addition can be accomplished at room temperature. Cyclization (achieved as described above for imidazopyridine 121) followed by standard basic saponification gives imidazopyridine 124. Hydroxamate 125 can be prepared from either imidazopyridine 121 or 124 using standard coupling procedures including but not limited to EDCI/HOBt, PyBOP, or DIC and the appropriate hydroxylamine. Alternatively, hydroxamate 125 can be prepared in two steps by initial conversion to the acid chloride by standard methods followed by addition of the hydroxyl amine.

Scheme 4 illustrates an alternative method of preparing compounds of Formula II. An appropriately functionalized 2-aminopyridine 126 in a suitable organic solvent such as dichloromethane or dichloroethane is reacted with a Lewis acid such as zinc bromide and condensation product (127) as disclosed by Katritzky et al. (*J. Org. Chem.*, 2003, 68, 4935-4937: *J. Org. Chem.*, 1990, 55, 3209-3213) to provide the 3-dialkyamino-imidazo[1,2-a]pyridine ring system 128. Condensation products 127 (i.e., condensation of a glyoxal, benzotriazole and a secondary amine) can be generated using benzotriazole, glyoxal and any appropriate secondary amine including, but not limited to dimethylamine, diethylamine, pyrrolidine, piperidine, morpholine, 1-methylpiperazine, N-methyl allylamine, diallyamine, and N-methyl benzylamine. The ester 128 is hydrolyzed by standard saponification methods, and the resulting acid can be converted to hydroxamate 129 by standard coupling procedures including but not limited to EDCI/HOBt, PyBOP, or DIC and the appropriate hydroxylamine. Alternatively, hydroxamate 129 can be prepared in two steps by initial conversion of the carboxylic acid to the acid chloride or activated ester by standard methods followed by addition of the hydroxylamine.

Scheme 5 illustrates an alternative method of preparing compounds of the Formula II. The preparation of 3-aminomethyl imidazo[1,2-a]pyridines 131 using the modified Mannich reaction procedure developed by Kercher et al. (manuscript in preparation) is illustrated. The reaction is generally carried out by combining 37% aqueous formaldehyde and a suitable amine in 6:1 acetonitrile/water. Several secondary amines can be employed including but not limited to pyrrolidine, piperadine, morpholine, dimethylamine, N-BOC-piperazine and 1-methylpiperazine. The solution of amine and formaldehyde is stirred for approximately half an hour after which time scandium triflate and the appropriate imidazo[1,2-a]pyridine 130 are sequentially added. The Mannich reaction is preferentially catalyzed by a group IIIA lanthanide triflate, preferably scandium triflate, though alternatively it may be performed using an excess of protic acid (AcOH or HCl) or elevated temperatures.

Scheme 6 illustrates an alternative method of preparing compounds of Formula II. In Scheme 6, the preparation of 3-aminomethyl imidazo[1,2-a]pyridines 134 via reductive alkylation is illustrated. In step 1, the 3-aminomethyl imidazo[1,2-a]pyridine 133 is prepared from the appropriate 3-formyl-imidazo[1,2-a]pyridine 132 and a suitable amine using standard reduction methods such as Na(CN)BH$_3$, Na(OAc)$_3$BH, NMe$_4$BH(OAc)$_3$ with or without the addition of acetic acid in a suitable nonreactive organic solvent such as methylene chloride, acetonitrile or tetrahydrofuran. The reductive amination is generally accomplished by treatment of the aldehyde derivative 132 with the amine and acetic acid in tetrahydrofuran at room temperature followed by the addition of Na(OAc)$_3$BH. In cases where R"=H, the corresponding secondary amine 133 can optionally be protected, for example with an acid labile protecting group such as tert-butyl carbamate (BOC) to facilitate handling in subsequent steps. In step 2, the ester is hydrolyzed by standard saponification methods, and the resulting acid can be converted to hydroxamate 134 by standard coupling procedures including but not limited to EDCI/HOBt, PyBOP, or DIC and the appropriate hydroxyl amine. Alternatively, hydroxamate 134 can be prepared in two steps by initial conversion of the carboxylic acid to the acid chloride or activated ester by standard methods followed by addition of the hydroxylamine. Protecting groups, if present, are removed after coupling.

Scheme 7 illustrates one method of preparing compounds of Formula III. In Scheme 7 the preparation of 3-alkyl-[1,2,4]triazolo[4,3-a]pyridine derivatives is illustrated. Compound 136 is prepared from compound 135 in a two step process. A suitably functionalized 2-chloropyridine derivative 135 is converted to the 2-hydrazinopyridine by reaction with hydrazine. The reaction is generally accomplished by reaction of hydrazine with 2-chloropyridine derivative 135 in an unreactive organic solvent such as DMF or DMA at elevated temperature (50 to 100° C.). The 2-hydrazinopyridine is then acylated with the appropriate carboxylic acid halide such as fluoride, chloride or bromide, or the appropriate carboxylic acid anhydride or mixed anhydride in a suitable unreactive organic solvent such as dichloromethane, and in the presence of a suitable base such as triethylamine, diisopropylethylamine or pyridine, to provide intermediate 136. Acylation of the 2-hydrazinopyridine can alternatively be accomplished by standard peptide coupling procedures with the appropriate carboxylic acid and appropriate coupling reagent, including but not limited to EDCI/HOBt, PyBOP, or DIC. The intermediate 136 is converted to 3-alkyl-[1,2,4]triazolo[4,3-a]pyridine 137 by treatment with an excess of phosphorus oxychloride in refluxing dichloromethane. The ester 137 is hydrolyzed by standard saponification methods, and the resulting acid 138 can be converted to hydroxamate 139 by standard peptide coupling procedures including but not limited to EDCI/HOBt, PyBOP, or DIC and the appropriate hydroxyl amine. Alternatively, hydroxamate 139 can be prepared in two steps by initial conversion of the carboxylic acid to the acid chloride or activated ester by standard methods followed by addition of the hydroxylamine.

Scheme 8 illustrates one method of preparing compounds of the Formula IV. In Scheme 8, the synthesis of 3-methyl-benzo[c]isoxazole derivatives is illustrated. Compound 141 is prepared from compound 140 in a two step process. Methyl ester 140 is treated with sodium azide in 3:1 acetone/water at elevated temperature (reflux) to effect nucleophilic substitution. The 4-azido derivative is then isolated and heated in water at reflux to effect cyclization to the benzo[c]isoxazole ring system 141. The ester 141 is hydrolyzed by standard saponification methods, and the resulting carboxylic acid can be converted to hydroxamate 142 by standard peptide coupling procedures including but not limited to EDCI/HOBt, PyBOP, or DIC and the appropriate hydroxylamine. Alternatively, hydroxamate 142 can be prepared in two steps by initial conversion of the carboxylic acid to the acid chloride or activated ester by standard methods followed by addition of the hydroxyl amine.

Scheme 9 illustrates one method of preparing compounds of Formula V. 2-Chloro-4-methyl-5-nitropyridine 143 can be converted to amino pyridine 144 in a three step sequence. In the first step, Sonagashria coupling using TMS-acetylene, CuI, amine base, palladium catalyst and organic solvent such as DME, THF, or DMF at temperatures from 25 to 100° C. gives the nitroacetylenic pyridine. Suitable palladium catalysts include, but are not limited to, PdCl$_2$(dppf), Pd(Ph$_3$P)$_4$, Pd(PPh$_3$)$_2$Cl$_2$ and Pd$_2$dba$_3$/dppf. Suitable amine bases include, but are not limited to, Et$_3$N, Hunig's base, and diisopropyl amine. The amino pyridine 144 is then prepared by removal of the TMS group under standard conditions such as K$_2$CO$_3$ in MeOH, followed by reduction of the nitro group using either Zn dust/AcOH, Fe or SnCl$_2$/MeOH. For Z=H, amino pyridine 144 is used directly in the cyclization reaction. When Z=Cl, aminopyridine 144 is halogenated under standard conditions with NCS in DMF and then carried forward to the cyclization. When Z=F, the 2-chloro-3-aminopyridine intermediate is treated with KF, Kryptofix in DMSO to prepare amino pyridine 145. Cyclization to give pyrazolo[1,5-a]pyridine 146 is accomplished by treating aminopyridine 145 with O-(4-nitrophenyl)-hydroxylamine in a suitable organic solvent such as DMF at room temperature in presence of a base such as K$_2$CO$_3$. Carboxylic acid 149 can be prepared, for example, using one the following routes. One route involves palladium mediated cross-coupling with appropriately substituted bromobenzene and amino-pyrazolo[1,5-a]pyridine 146. In this case, the cross-coupling can be accomplished with palladium catalyst and organic solvent such as DME, THF, dioxane, and toluene at temperatures from 60 to 120° C. Suitable palladium catalysts include, but are not limited to, Pd(OAc)$_2$, PdCl$_2$(dppf), Pd$_2$(bda)$_3$, and Pd(dba)$_2$. Suitable ligands include, but are not limited to, BINAP, DPPF, and (o-tol)$_3$P. Suitable amine bases include, but are not limited to, NaOt-Bu, KOt-Bu, and Cs$_2$CO$_3$. The second route involves S$_N$Ar reaction with amino-pyrazolo[1,5-a]pyridine 146 and the appropriately substituted 2-fluoronitro-benzene. In this case, the coupling can be accomplished by mixing the two components in a suitable organic solvent such as xylenes, toluene, DMSO or DMF at elevated temperatures (80 to 150° C.). Optionally, a base can be employed in the S$_N$Ar coupling such as K$_2$CO$_3$ or Cs$_2$CO$_3$. The carboxylic acid 149 is then prepared by functionalization of the aromatic ring followed by oxidation. In the first case, functionalization involves halogenation under standard conditions with either NCS or NBS in DMF. In the second case, functionalization involves Sandmeyer chemistry to convert the nitroarene into the desired arene or arylhalide (nitro group reduction; diazonation; halogentation or protonation). In both routes, the last step to prepare carboxylic acid 149 is oxidation of the toluyl moiety. This can be achieved using standard methods including but not limited to KMnO$_4$, NaOCl/RuCl$_3$ or Na$_2$Cr$_2$O$_7$/HCl. The resulting carboxylic acid 149 can be converted to hydroxamate 150 by standard peptide coupling procedures including but not limited to EDCI/HOBt, PyBOP, or DIC and the appropriate hydroxylamine. Alternatively, hydroxamate 150 can be prepared in two steps by initial conversion of the carboxylic acid to the acid chloride or activated ester by standard methods followed by addition of the hydroxylamine.

The invention also relates to a pharmaceutical composition for the treatment of a hyperproliferative disorder in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or the treatment of pain in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemanglioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, prodrug or hydrate thereof. In one embodiment, said method relates to the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemanglioma, glioma, melanoma, Kaposi's sarcoma and ovarian, breast, lung, pancreatic, prostate, colon and epidermoid cancer.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective in sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the present invention and pharmaceutical compositions described herein. Examples of useful COX-II inhibitors include CELEBREX™ (alecoxib), valdecoxib, etoricoxib, lumiracoxib and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of MEK, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I-V or a pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-V, or a pharmaceutically acceptable salt or prodrug thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 0.5 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I-V will naturally vary according to the nature and severity of the conditions, the age and sex of the animal or patient and the route of administration, according to well known principles of medicine.

The compounds of this invention may be used alone in combination with other drugs and therapies used in the treatment of disease states which would benefit from the inhibition of MEK. For example, a compound of this invention may be applied in combination with one or more other anti-tumor substances, including, but not limited to, mitotic inhibitors such as vinblastine; alkylating agents such as cisplatin, carboplatin and cyclophosphamide; anti-metabolites such as 5-fluorouracil, cytosine arabinside and hydroxyurea; or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; signal transduction inhibitors, such as agents that can inhibit EGFR (epiderman growth factor receptor) responses, such as EGRF antibodies, EGF antibodies and molecules that are EGFR inhibitors such as the compounds ZD-1839 (AstraZeneca) and BIBX-1382 (Boehringer Ingelheim); VEGF inhibitors such as SU-6668 (Sugen Inc. of South San Francisco, Calif., USA) or the anti-VEGF monoclonal antibody of Genentech, Inc. of South San Francisco, Calif.; cell cycle inhibitors; intercalating antibiotics such as adriamycin and bleomycin; enzymes, for example, interferon; and anti-hormone such as anti-estrogens such as Nolvadex™ (tamoxifen); or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

Although the compounds of Formula I-V are primarily of value as therapeutic agents for use in warm-blooded animals (including man), they are also useful whenever it is required to inhibit the effects of MEK. Thus, they are useful as pharmacological standards for use in the development of new biological tests and in the search for new pharmacological agents.

The activity of the compounds of the present invention may be determined by the following procedure. N-terminal 6 His-tagged, constitutively active MEK-1 (2-393) is expressed in *E. coli* and protein is purified by conventional methods (Ahn et al., *Science* 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in *E. coli* and is purified by conventional methods, in the presence of MEK-1. The assay is carried out in 96-well polypropylene plate. The incubation mixture (100 µL) comprises of 25 mM Hepes, pH 7.4, 10 mM $MgCl_2$, 5 mM $\beta$-glycerolphosphate, 100 µM Na-orthovanadate, 5 mM DTT, 5 nM MEK1, and 1 µM ERK2. Inhibitors are suspended in DMSO, and all reactions, including controls are performed at a final concentration of 1% DMSO. Reactions are initiated by the addition of 10 µM ATP (with 0.5 µCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 µL/well of Packard Microscint 20, and plates are counted using a Packard TopCount. In this assay, compounds of the invention exhibited an $IC_{50}$ of less than 50 micromolar.

Representative compounds of the present invention, which are encompassed by the present invention include, but are not limited to the compounds of the examples and their pharmaceutically acceptable acid or base addition salts or prodrugs thereof. The examples presented below are intended to illustrate particular embodiments of the invention, and are not intended to limit the scope of the specification or the claims in any way.

The disclosures in this application of all articles and references, including patents, are incorporated herein by reference.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Bruker instrument operating at 300 MHz or on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

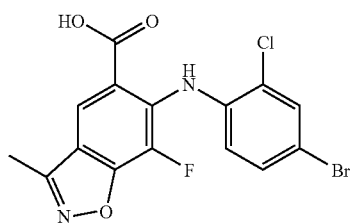

Synthesis of 6-(4-bromo-2-chlorophenylamino)-7-fluoro-3-methylbenzo[d]isoxazole-5-carboxylic acid (9a)

The reaction scheme for the synthesis of compound 9a is shown in FIG. 1.

Step A: Preparation of 5-bromo-2,3,4-trifluorobenzoic acid (2): To a solution of 1-bromo-2,3,4-trifluorobenzene (1) (5.0 mL, 41.7 mmol) in THF (120 mL) was added lithium diisopropylamine (2.0 M solution, 21 mL, 42 mmol) at −78° C. After stirring for 1 hour at −78° C., the mixture was added to a solution of CO$_2$ in THF (1 L). The dry-ice bath was removed and the reaction mixture stirred overnight at room temperature. The reaction mixture was quenched with 10% aqueous HCl (835 mL), concentrated, and washed with ether (250 mL). The combined organics were washed with 5% aqueous NaOH (300 mL) and water (100 mL, pH 12). The aqueous layer was acidified (pH 0) with concentrated HCl. The resulting suspension was extracted with ether (2×300 mL), dried over MgSO$_4$, filtered, concentrated under reduced pressure to afford 7.70 g (72% yield) of the desired product (2).

Step B: Preparation of 5-bromo-2-(2-chlorophenylamino)-3,4-difluorobenzoic acid (3): To a solution of lithium diisopropylamine (49.0 mL, 2 M in THF/heptane) in THF (40 mL) was added 2-chlorophenylamine (6.50 mL, 60.6 mmol) at −78° C. After vigorous stirring for 10 minutes, a solution of 5-bromo-2,3,4-trifluoro-benzoic acid (2) (7.70 g, 30.2 mmol) in THF (60 mL) was added. The dry-ice bath was removed and the reaction mixture stirred for 4 hours at room temperature. The mixture was concentrated, treated with 10% aqueous HCl (75 mL), and extracted with EtOAc. The combined organic extracts were dried over MgSO$_4$, filtered, and concentrated. Purification by trituration with boiling CH$_2$Cl$_2$ gave 7.24 g (66%) of the desired acid (3) as a yellow solid Step C: Preparation of 5-bromo-2-(2-chlorophenylamino)-3,4-difluorobenzoic acid methyl ester (4): To a solution of 5-bromo-2-(2-chlorophenylamino)-3,4-difluorobenzoic acid (3) (4.50 g, 12.4 mmol) in a 3:1 mixture of THF:MeOH (32 mL) was added (trimethylsilyl)-diazomethane (8.10 ml of a 2 M solution in hexanes) at room temperature. After stirring for 2 hours, the reaction mixture was quenched with acetic acid, diluted with EtOAc, and washed with water. The organic layer was dried (MgSO$_4$) and concentrated under reduced pressure to give 4.35 g (93%) of the desired methyl ester (4).

Step D: Preparation of 2-(2-chlorophenylamino)-3,4-difluoro-5-trimethylsilanylethynyl-benzoic acid methyl ester (5): A mixture of 5-bromo-2-(2-chlorophenylamino)-3,4-difluorobenzoic acid methyl ester (4) (101 mg, 0.268 mmol), TMS-acetylene (0.045 mL, 0.31 mmol), Pd(PPh$_3$)$_2$Cl$_2$ (18.7 mg, 0.0261 mmol), CuI (5.1 mg, 0.027 mmol), and i-Pr$_2$NH (0.075 mL, 0.53 mmol) in THF (1.5 mL) was stirred for 16 hours at room temperature. The reaction mixture was concentrated under reduced pressure, and diluted with EtOAc. The organic layer was washed with saturated aqueous NH$_4$Cl and brine, dried over MgSO$_4$, and concentrated. Purification by flash column chromatography using the Biotage system (100% hexane to 1% EtOAc in hexane) gave 81.3 mg (77% yield) of the desired product (5).

Step E: Preparation of 5-acetyl-2-(2-chlorophenylamino)-3,4-difluorobenzoic acid methyl ester (6): A mixture of 2-(2-chlorophenylamino)-3,4-difluoro-5-trimethylsilanylethynylbenzoic acid methyl ester (5) (79.4 mg, 0.20 mmol), HgSO$_4$ (59.8 mg, 2.0 mmol), and conc. H$_2$SO$_4$ (0.02 mL, 0.40 mmol) in 80% aqueous acetone (2.5 mL), were refluxed for 48 hours. The reaction was concentrated under reduced pressure, and diluted with EtOAc. The organic layer was washed with water and brine, dried over MgSO$_4$ and concentrated to give 50.1 mg (73%) of the desired product (6).

Step F: Preparation of 6-(2-chlorophenylamino)-7-fluoro methylbenzo[d]isoxazole-5-carboxylic acid methyl ester (7): t-BuOK (0.47 mL, 1.0 M in THF) was added to propan-2-one oxime (35 mg, 0.47 mmol). After stirring for 30 minutes, THF (0.5 mL) was added, and the reaction mixture was cooled to −78° C. A solution of 5-acetyl-2-(2-chlorophenylamino)-3,4-difluorobenzoic acid methyl ester (6) (50.0 mg, 0.147 mmol) in THF (1 mL) was added. The reaction mixture was slowly warmed to 0° C. and stirred for 2 hours. The reaction mixture was quenched with saturated aqueous NH$_4$Cl, diluted with EtOAc and water. The aqueous layer was separated and extracted with EtOAc. The combined organic extracts were dried over MgSO$_4$, filtered, and concentrated in vacuo to give the 5-acetyl-2-(2-chloro-phenylamino)-3-fluoro-4-isopropylideneaminooxy-benzoic acid methyl ester. The recovered oxime was suspended in a 1:1 mixture of 5% aqueous HCl and MeOH (30 ml) and heated to reflux. After 1 hour, the reaction mixture was cooled to room temperature and diluted with EtOAc. The organic layer was washed with water, dried (MgSO$_4$) and concentrated. Purification by flash column chromatography using the Biotage system (40% methylene chloride in hexanes) provided 17 mg (35% for two steps) of the desired product (7).

Step G: Preparation of 6-(4-bromo-2-chlorophenylamino)-7-fluoro-3-methyl-benzo[d]isoxazole-5-carboxylic acid methyl ester (8a): 6-(2-Chlorophenylamino)-7-fluoro-3-methylbenzo[d]isoxazole-5-carboxylic acid methyl ester (7) (18.6 mg, 0.0556 mmol) and N-bromosuccinimide (12.0 mg, 0.0667 mmol) were stirred in DMF (1 mL) for 16 hours. The reaction mixture was diluted with EtOAc, and washed with water (2×). The organic layer was dried over MgSO$_4$, filtered, and concentrated. Purification by flash column chromatography using the Biotage system (10% EtOAc in hexanes) provided 12.6 mg (55%) of the desired product (8a).

Step H: Preparation of 6-(4-bromo-2-chlorophenylamino)-7-fluoro-3-methylbenzo[d]isoxazole-5-carboxylic acid (9a): To a solution of 6-(4-bromo-2-chlorophenylamino)-7-fluoro-3-methylbenzo[d]isoxazole-5-carboxylic acid methyl ester (8a) (200 mg, 0.48 mmol) in THF-water (3 mL/1.5 mL) was added aqueous LiOH (1 M, 1.00 mL) at room temperature. After 15 hours, the reaction mixture was acidified to pH 1 with aqueous HCl (1 M), diluted with water, and extracted with EtOAc/THF. The organic layer was washed with water, dried over MgSO$_4$, filtered, and concentrated in vacuo to give 191.5 mg (99%) of the crude acid (9a) which was used without further purification. MS APCI (−) m/z 397, 399 (M+, Br, Cl pattern) detected: $^1$H NMR (400 MHz, DMSO-d$_6$) δ 9.55 (s, 1H), 8.37 (s, 1H), 7.75 (s, 1H), 7.42 (d, 1H), 6.97 (t, 1H), 2.60 (s, 3H): $^{19}$F NMR (376 MHz, DMSO-d$_6$) −140.15 (s, 1F).

Example 2

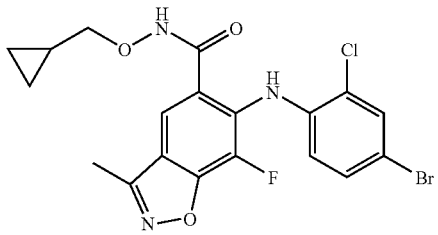

Synthesis of 6-(4-bromo-2-chlorophenylamino)-7-fluoro-3-methylbenzo[d]isoxazole-5-carboxylic acid cyclopropylmethoxyamide (10a)

The reaction scheme for the synthesis of compound 10a is shown in FIG. 1. To a solution of 6-(4-bromo-2-chlorophenylamino)-7-fluoro-3-methylbenzo[d]isoxazole-5-carboxylic acid (9a) (50.0 mg, 0.125 mmol) in DMF (1 mL) was added HOBt (24.6 mg, 0.161 mmol), Et$_3$N (0.060 mL, 0.43 mmol), O-cyclopropylmethyl-hydroxylamine (15.5 mg, 0.178 mmol), and 1-(3-dimethylaminopropyl)-3-ethylcarbodiimide hydrochloride (EDCl) (32.2 mg, 0.168 mmol) at room temperature. After 6 days, the reaction mixture was diluted with EtOAc, washed with saturated aqueous NH$_4$Cl, brine, saturated aqueous NaHCO$_3$, and brine. The organic layer was dried over MgSO$_4$, filtered, concentrated in vacuo, and purified by flash column chromatography using the Biotage system (0.5% MeOH in CH$_2$Cl$_2$) to give 27.6 mg (47% yield) of the desired product (10a). MS APCI (−) m/z 466, 468 (M+, Br, Cl pattern) detected: $^1$H NMR (400 MHz, CD$_3$OD) δ 7.82 (s, 1H), 7.57 (d, 1H), 7.31 (dd, 1H), 6.74 (dd, 1H), 3.73 (d, 2H), 2.60 (s, 3H), 1.16 (m, 1H), 0.55 (m, 2H), 0.28 (m, 2H): $^{19}$F NMR (376 MHz, CD$_3$OD) −140.96 (s, 1F).

Example 3

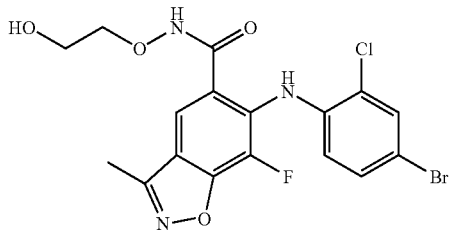

Synthesis of 6-(4-bromo-2-chlorophenylamino)-7-fluoro-3-methylbenzo[d]isoxazole-5-carboxylic acid (2-hydroxyethoxy)-amide (12a)

Figure 2:
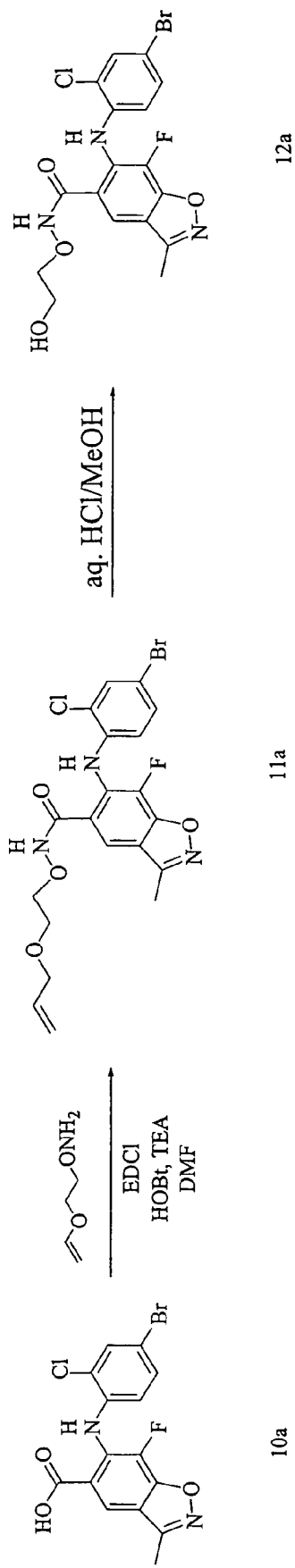

The reaction scheme for the synthesis of compound 12a is shown in FIG. 2.

Step A: Preparation of 6-(4-bromo-2-chlorophenylamino)-7-fluoro-3-methyl-benzo[d]isoxazole-5-carboxylic acid (2-vinyloxyethoxy)-amide (11a): To a solution of 6-(4-bromo-2-chlorophenylamino)-7-fluoro-3-methylbenzo[d]isoxazole-5-carboxylic acid (10a) (75.2 mg, 0.188 mmol) in DMF (1.5 mL) was added HOBt (38.2 mg, 0.249 mmol), Et$_3$N (0.080 mL, 0.571 mmol), O-(2-vinyloxyethyl)hydroxylamine (28.5 mg, 0.276 mmol), and EDCl (47.2 mg, 0.246 mmol) at room temperature. After 6 days, the reaction mixture was diluted with EtOAc, washed with saturated aqueous NH$_4$Cl, brine, saturated aqueous NaHCO$_3$, and brine. The organic layer was dried over MgSO$_4$, filtered, concentrated in vacuo, and purified by flash column chromatography using the Biotage system (3% MeOH in CH$_2$Cl$_2$) to give 57.8 mg (63%) of the desired product (11a).

Step B: Preparation of 6-(4-bromo-2-chlorophenylamino)-7-fluoro-3-methylbenzo[d]isoxazole-5-carboxylic acid (2-hydroxyethoxy)-amide (12a): A solution of 6-(4-bromo-2-chlorophenylamino)-7-fluoro-3-methylbenzo[d]isoxazole-5-carboxylic acid (2-vinyloxyethoxy)amide (11a) (55.4 mg, 0.114 mmol) and aqueous HCl (1 M, 0.23 mL) in EtOH (3 mL) was stirred for 2 hours at room temperature. The pH of the reaction mixture was adjusted to 6-7 with aqueous NaOH (2 N). The reaction was diluted with EtOAc. The organic layer was washed with water, dried over MgSO$_4$, filtered, and concentrated in vacuo to give 50.2 mg (96% yield) of the desired product (12a). MS APCI (−) m/z 456, 458 (M+, Br, Cl pattern) detected: $^1$H NMR (400 MHz, CD$_3$OD) δ 7.87 (s, 1H), 7.57 (d, 1H), 7.31 (dd, 1H), 6.74 (dd, 1H), 4.01 (t, 2H), 3.74 (t, 2H), 2.60 (s, 3H): $^{19}$F NMR (376 MHz, CD$_3$OD) −140.85 (s, 1F).

Example 4

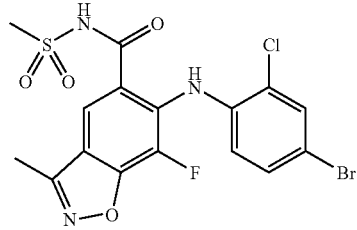

Synthesis of N-[6-(4-bromo-2-chlorophenylamino)-7-fluoro-3-methylbenzo[d]isoxazole-5-carbonyl]-methanesulfonamide (13a)

Figure 3:
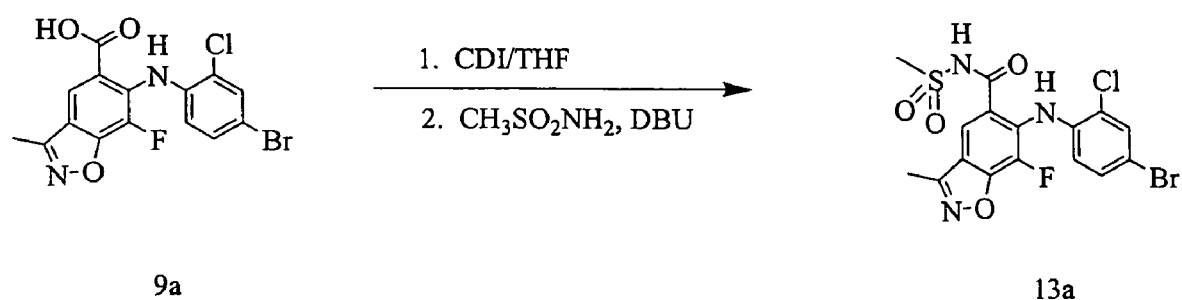

The reaction scheme for the synthesis of compound 13a is shown in FIG. 3. A mixture of 6-(4-bromo-2-chlorophenylamino)-7-fluoro-3-methylbenzo[d]isoxazole-5-carboxylic acid (9a) (41 mg, 0.102 mmol) and carbonyl diimidazole (23 mg, 0.140 mmol) in THF (1 mL) was stirred at 50° C. in a sealed tube reactor. The reaction mixture was cooled to room temperature and methanesulfonamide (17 mg, 0.179 mmol) was added followed by DBU (0.025 ml, 0.164 mmol). After stirring at 50° C. for 1 hour, the reaction mixture was cooled to room temperature, and diluted with EtOAc. The organic layer was washed with water, 1 N HCl, and brine. The organic layer was dried (MgSO$_4$) and concentrated. Purification by flash column chromatography using the Biotage system (7% MeOH in CH$_2$Cl$_2$) provided 34 mg (65% yield) of the desired product (13a). MS APCI (−) m/z 474, 476 (M+, Br, Cl pattern) detected: $^1$H NMR (400 MHz, CD$_3$OD) δ 8.27 (s, 1H), 7.53

(s, 1H), 7.27 (d, 1H), 6.73 (t, 1H), 3.11 (s, 3H), 2.55 (s, 3H): $^{19}$F NMR (376 MHz, CD$_3$OD) −141.84 (s, 1F).

Example 5

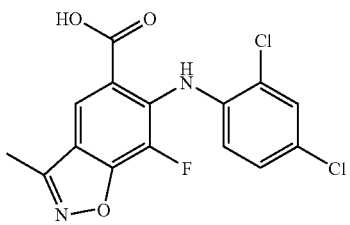

Synthesis of 6-(2,4-dichloro-phenylamino)-7-fluoro-3-methylbenzo[d] isoxazole-5-carboxylic acid (9b)

The reaction scheme for the synthesis of compound 9b is shown in FIG. 1.

Step A: Preparation of 6-(2,4-dichlorophenylamino)-7-fluoro-3-methylbenzo[d]isoxazole-5-carboxylic acid methyl ester (8b): 6-(2-Chlorophenylamino)-7-fluoro-3-methylbenzo[d]isoxazole-5-carboxylic acid methyl ester (7) (129 mg, 0.384 mmol) and N-chlorosuccinimide (57 mg, 0.421 mmol) were stirred in DMF (5 mL) for 16 hours. Concentrated HCl (3 μL) was added and the reaction mixture stirred 2 hours. The reaction mixture was diluted with EtOAc, and washed with water (2×). The organic layer was dried over MgSO$_4$, filtered, and concentrated. Purification by flash column chromatography using the Biotage system (5% EtOAc in hexanes) provided 73 mg (52%) the desired product (8b).

Step B: Preparation of 6-(2,4-dichlorophenylamino)-7-fluoro-3-methylbenzo[d]isoxazole-5-carboxylic acid (9b): Compound 9b was prepared according to Step H of Example 1 using 6-(2,4-dichlorophenylamino)-7-fluoro-3-methylbenzo[d]isoxazole-5-carboxylic acid methyl ester (8b) to provide 68 mg (98% yield) of the desired product (9b). MS APCI (−) m/z 353, 355 (M+, Br, Cl pattern) detected: $^1$H NMR (400 MHz, DMSO-d$_6$) δ 9.58 (s, 1H), 8.34 (s, 1H), 7.65 (d, 1H), 7.31 (dd, 1H), 7.04 (dd, 1H), 2.60 (s, 3H): $^{19}$F NMR (376 MHz, DMSO-d$_6$) −140.36 (s, 1F).

Example 6

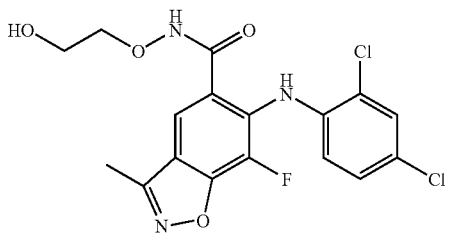

Synthesis of 6-(2,4-dichlorophenylamino)-7-fluoro-3-methylbenzo[d]isoxazole-5-carboxylic acid (2-hydroxyethoxy)amide (12b)

Figure 4:
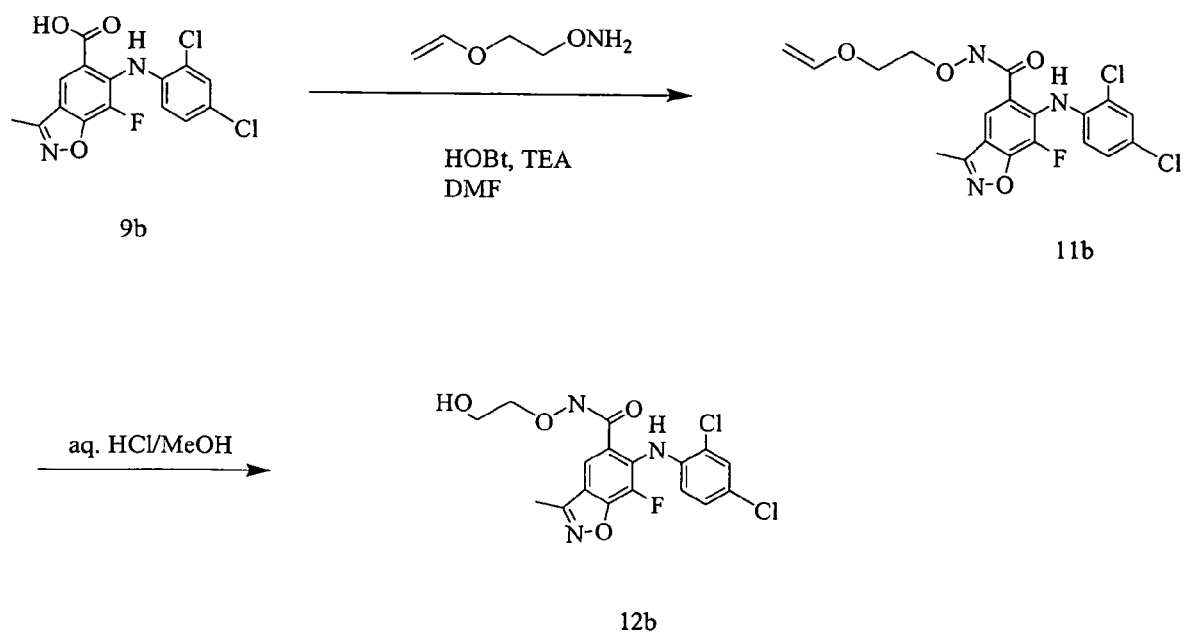
FIG. 4 shows a reaction scheme for the synthesis of compound 12b.

The reaction scheme for the synthesis of compound 12b, as shown in FIG. 4, was carried out according to Steps A and B of Example 3 using 6-(2,4-dichlorophenylamino)-7-fluoro-3-methylbenzo[d]isoxazole-5-carboxylic acid (9b) as the starting material to provide 29 mg (38% yield for two steps) of 12b. MS APCI (−) m/z 412, 414 (M+, Br, Cl pattern) detected: $^1$H NMR (400 MHz, CD3OD) δ 7.87 (s, 1H), 7.45 (m, 1H), 7.19 (m, 1H), 6.80 (m, 1H), 4.02 (t, 2H), 3.75 (t, 2H), 2.60 (s, 3H); $^{19}$F NMR (376 MHz, CD3OD) −141.05 (s, 1F).

Example 7

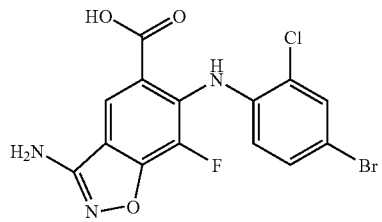

Synthesis of 3-amino-6-(4-bromo-2-chlorophenylamino)-7-fluorobenzo[d]isoxazole-5-carboxylic acid (19)

Figure 5:
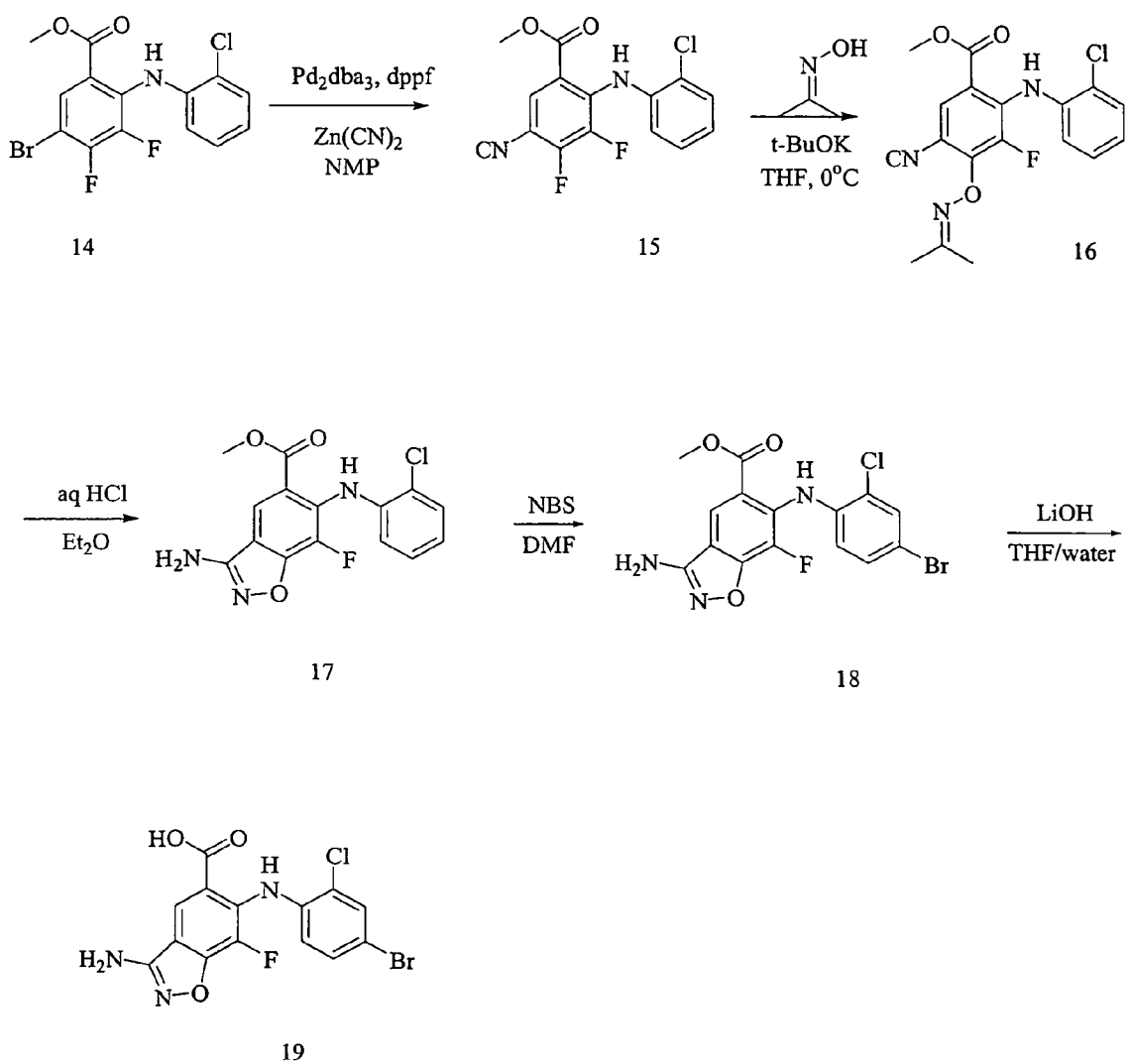
FIG. 5 shows a reaction scheme for the synthesis of compound 19.

The reaction scheme for the synthesis of compound 19 is shown in FIG. 5.

Step A: Preparation of 2-(2-chlorophenylamino)-5-cyano-3,4-difluorobenzoic acid methyl ester (15): A mixture of 5-bromo-2-(2-chlorophenylamino)-3,4-difluorobenzoic acid methyl ester (14) (3.01 g, 7.99 mmol), 1,1'-bis(diphenylphosphino)ferrocene (dppf) (93 mg, 0.162 mmol), Pd$_2$dba$_3$ (73 mg, 0.080 mmol) and Zn(CN)$_2$ (573 mg, 4.78 mmol) in 1-methyl-2-pyrrolidinone (NMP: 4.5 mL) was heated in a sealed tube reactor. After 20 hours, the reaction mixture was cooled to room temperature, quenched by the addition of 8 mL 4:1:4 (volume) mixture of saturated NH$_4$Cl, concentrated NH$_4$OH and water, and extracted with a mixture of EtOAc:THF. The combined organic extracts were washed with 4:1:4 (volume) mixture of saturated NH$_4$Cl, concentrated NH$_4$OH and water, and brine. The organic layer was dried (MgSO$_4$) and concentrated. Purification by flash column chromatography using the Biotage system (twice: 100% hexanes to 35% CH$_2$Cl$_2$ in hexanes, then 30% CH$_2$Cl$_2$ in hexanes) provided 1.33 g (52%) of the desired product (15).

Step B: Preparation of 3-amino-6-(2-chlorophenylamino)-7-fluorobenzo[d]isoxazole-5-carboxylic acid methyl ester (17): t-BuOK (3.80 mL of a 1.0 M solution in THF) was added to a stirred solution of acetone oxime (285 mg, 3.82 mmol) in THF (5 mL) at room temperature. The reaction mixture was further diluted with THF (20 mL) and after 30 minutes cooled to 0° C. A solution of 2-(2-chlorophenylamino)-5-cyano-3,4-difluorobenzoic acid methyl ester (15) (600 mg, 1.86 mmol) in THF (5 mL) was added. The reaction mixture was slowly warmed to room temperature. After 90 minutes, the reaction mixture was quenched with saturated NH$_4$Cl and diluted with EtOAc. The organic layer was washed with saturated NH$_4$Cl and brine, dried (MgSO$_4$) and concentrated. The residue (16) was diluted with MeOH (10 mL) and a solution of 2 M HCl in diethyl ether (10 mL) was added. After 16 hours, the reaction mixture was diluted with EtOAc, washed with water, saturated NaHCO$_3$ and water. The organic layer was dried (MgSO$_4$) and concentrated. Purification by flash column chromatography using the Biotage system (1.5% MeOH in CH$_2$Cl$_2$) provided 399 mg (64%) of the desired product (17).

Step C: Preparation of 3-amino-6-(4-bromo-2-chlorophenylamino)-7-fluorobenzo[d]isoxazole-5-carboxylic acid methyl ester (18): Compound 18 was prepared according to Step G of Example 1 using compound 17 as the starting material.

Step D: Preparation of 3-amino-6-(4-bromo-2-chlorophenylamino)-7-fluoro-benzo[d]isoxazole-5-carboxylic acid (19): Compound 19 was prepared according to Step H of Example 1 using 3-amino-6-(4-bromo-2-chlorophenylamino)-7-fluorobenzo[d]isoxazole-5-carboxylic acid methyl ester (18) as the starting material to provide 188 mg (98% yield) of compound 19. MS APCI (−) m/z 398, 400 (M+, Br, Cl pattern) detected: $^1$H NMR (400 MHz, DMSO-$d_6$) δ 9.47 (s, 1H), 8.49 (s, 1H), 7.73 (m, 1H), 7.41 (dd, 1H), 6.92 (t, 1H), 6.76 (s, 2H): $^{19}$F NMR (376 MHz, DMSO-$d_6$) −141.48 (s, 1F).

Example 8

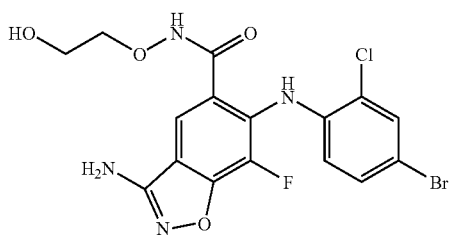

Synthesis of 3-amino-6-(4-bromo-2-chloro-phenylamino)-7-fluorobenzo [d]isoxazole-5-carboxylic acid (2-hydroxyethoxy)-amide (21).

Figure 6:
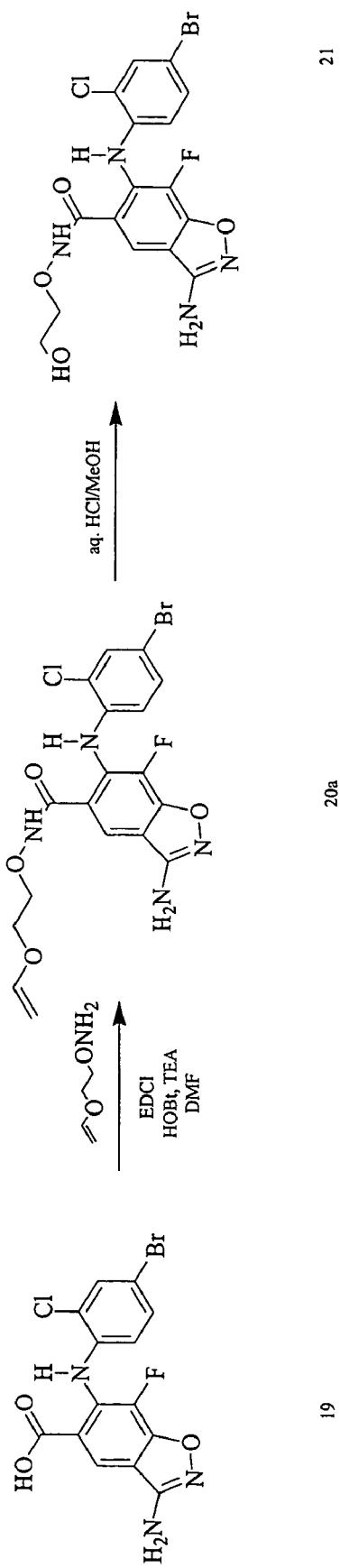
FIG. 6 shows a reaction scheme for the synthesis of compound 21.

The reaction scheme for the synthesis of compound 21, as shown in FIG. 6, was accomplished according to Steps A and B of Example 3 using 3-amino-6-(4-bromo-2-chlorophenylamino)-7-fluorobenzo[d]isoxazole-5-carboxylic acid (19) as the starting material to provide 16 mg (23% yield for two steps) of compound 21. MS APCI (−) m/z 457, 459 (M+, Br, Cl pattern) detected: $^1$H NMR (400 MHz, DMSO-$d_6$) δ 11.92 (s, 1H), 8.59 (s, 1H), 7.94 (s, 1H), 7.69 (s, 1H), 7.36 (d, 1H), 6.75 (dd, 1H), 6.71 (s, 2H), 4.73 (s, 1H), 3.87 (s, 2H), 3.59 (s, 2H): $^{19}$F NMR (376 MHz, DMSO-$d_6$) −140.64 (s, 1F).

Example 9

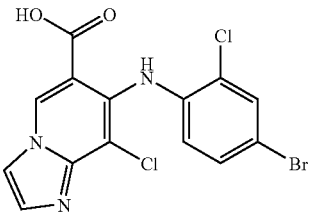

Synthesis of 7-(4-bromo-2-chlorophenylamino)-8-chloroimidazo[1,2-a]pyridine-6-carboxylic acid (30)

Figure 7:
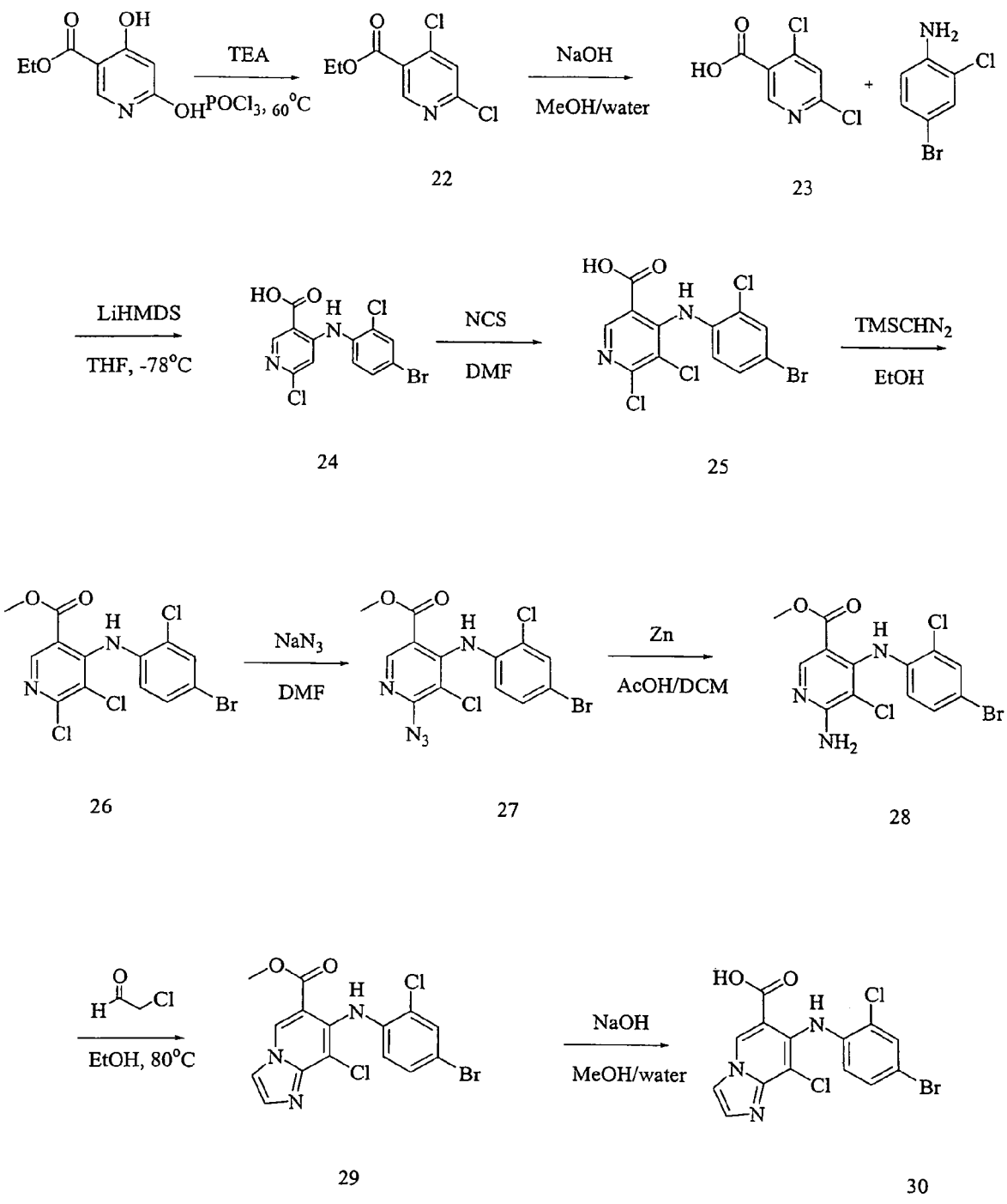
FIG. 7 shows a reaction scheme for the synthesis of compound 30.

The reaction scheme for the synthesis of compound 30 is shown in FIG. 7

Step A: Preparation of 4,6-dichloronicotinic acid ethyl ester (22): POCl$_3$ (100 mL, 1092 mmol) was added to 4,6-dihydroxynicotinic acid ethyl ester (*J. Heterocyclic Chem.* 1983, 20, 1363) (20.0 g, 109 mmol). The resulting suspension was cooled to 0° C. and triethylamine (15.2 mL, 109 mmol) was added dropwise at such a rate as to maintain the internal reaction mixture temperature below 25° C. Upon completion of addition, the reaction mixture was warmed to room temperature and then to 80° C. After 4 hours, the reaction mixture was cooled to room temperature and stirred for 16 hours. The reaction mixture was carefully poured onto 2 L crushed ice. The mixture was extracted with EtOAc and diethyl ether. The combined organic extracts were washed with brine, dried (Na$_2$SO$_4$) and concentrated. The dark brown liquid was purified by passing through a plug of silica gel (CH$_2$Cl$_2$) to give the desired product (22) as a low melting yellow solid (18.7 g, 78%).

Step B: Preparation of 4,6-dichloronicotinic acid (23): Sodium hydroxide (40 mL, 6.25 M solution) was added to a stirred solution of 4,6-dichloronicotinic acid ethyl ester (22) (25.95 g, 118 mmol) in 4:1:1 THF:MeOH:water (600 mL). After 30 minutes, the reaction mixture was acidified to pH 2 with concentrated HCl, diluted with 1:1 EtOAc:Et$_2$O and washed with water and brine. The organic layer was dried (Na$_2$SO$_4$) and concentrated. The resulting off-white solid was twice concentrated from toluene to give the desired product (23) as a white solid (21.73 g, 96%).

Step C: Preparation of 4-(4-bromo-2-chlorophenylamino)-6-chloronicotinic acid hydrochloride salt (24): LiHMDS (261 mL of a 1 M solution in hexanes) was added dropwise over 30 minutes to a solution of 4-bromo-2-chlorophenylamine (35.0 g, 172 mmol) in THF (80 mL) at −78° C. After 1 hour, 4,6-dichloronicotinic acid (23) (15.7 g, 81.7 mmol) was added dropwise over 30 minutes. The reaction mixture was slowly warmed to room temperature and stirred 16 hours. The reaction mixture was quenched with water, diluted with EtOAc and acidified with 1 N HCl. The resulting precipitate was isolated by filtration and washed with EtOAc. The solids were twice concentrated from toluene, triturated with CH$_2$Cl$_2$ and collected by filtration. The solids were further concentrated from toluene (3×) followed by drying in vacuo to give the desired product (24) containing a small amount of water (36.0 g).

Step D. Preparation of 4-(4-Bromo-2-chloro-phenylamino)-5,6-dichloro-nicotinic acid (25): N-Chlorosuccinimide was (13.0 g, 99.0 mmol) added to a suspension of 4-(4-bromo-2-chloro-phenylamino)-6-chloro-nicotinic acid (24) (32.54 g, 89.9 mmol) in DMF (500 mL). The suspension was allowed to stir at room temperature overnight. The reaction mixture was diluted with saturated sodium bisulfite (200 mL) and water (1L) resulting in formation of a thick white precipitate which was isolated by filtration and washed with water. The solids were dissolved into THF. Two volumes of diethyl ether were added and the organic solution washed with brine, dried over NaSO$_4$, filtered, and concentrated in vacuo to provide an orange solid. The solid was triturated with diethyl ether to provide the desired product as an off-white solid (25) (13.34 g, 37%). MS (APCI−) m/z 393, 395, 397 (M−; Cl, Br pattern) detected.

Step E. Preparation of 4-(4-Bromo-2-chloro-phenylamino)-5,6-dichloro-nicotinic acid methyl ester (26): Trimethylsilyldiazomethane (2.0 M solution in hexanes, 37 mL, 74 mmol) was added slowly to a suspension of 4-(4-bromo-2-chloro-phenylamino)-5,6-dichloro-nicotinic acid (25) (14.67 g, 37 mmol). After the addition was complete the resulting slurry was diluted with hexanes (600 mL) and the solids isolated by filtration washing with hexanes. The desired product was isolated as an off-white solid (10.06 g). The hexanes washes were concentrated and the solids passed through a plug of silica gel eluting with dichloromethane. Concentration of the product-containing fractions provided an additional 3.83 g desired product (26) for a total of 13.89 g (91%). MS (APCI+) m/z 409, 411, 413 (M+; Cl, Br pattern) detected.

Step F. Preparation of 6-Azido-4-(4-bromo-2-chloro-phenylamino)-5-chloro-nicotinic acid methyl ester (27): Sodium azide (4.4 g, 68 mmol) was added to a suspension of 4-(4-bromo-2-chloro-phenylamino)-5,6-dichloro-nicotinic acid methyl ester (26) (13.89 g, 33.8 mmol) in DMF (200 mL) and the mixture allowed to stir at room temperature overnight. The solution was diluted with water (600 mL) and the resulting white precipitate was collected by filtration and washed with water. The solids were dissolved into THF. Two volumes of diethyl ether were added and the organic solution washed with brine, dried over $NaSO_4$, filtered, and concentrated in vacuo to the desired product (27) as a light yellow solid (12.94 g, 92%).

Step G. Preparation of 6-Amino-4-(4-bromo-2-chloro-phenylamino)-5-chloro-nicotinic acid methyl ester (28): Zinc powder (10 g, 155 mmol) was added portionwise to a suspension of 6-azido-4-(4-bromo-2-chloro-phenylamino)-5-chloro-nicotinic acid methyl ester (27) (12.94 g, 31 mmol) in 3:1 dichloromethane/acetic acid (300 mL). After fifteen minutes the reaction mixture was poured into 700 mL ethyl acetate, washed with water, saturated sodium bicarbonate and brine. The organic solution was dried over $NaSO_4$, filtered, and concentrated in vacuo to provide the desired product (28) as an off-white solid (11.85 g, 98%). MS (APCI+) m/z 390, 392, 394 (M+; Cl, Br pattern) detected.

Step H. Preparation of 7-(4-Bromo-2-chloro-phenylamino)-8-chloro-imidazo[1,2-a]pyridine-6-carboxylic acid methyl ester (29): Chloroacetaldehyde (50% aqueous solution, 0.70 mL, 5.7 mmol) was added to a suspension of 6-amino-4-(4-bromo-2-chloro-phenylamino)-5-chloro-nicotinic acid methyl ester (28) in DMF (7 mL) contained in a sealed tube. The reaction mixture was heated at 80° C. for four hours and then allowed to cool to room temperature and stir overnight. The dark brown solution was diluted with water (70 mL) the resulting light brown precipitate was collected by filtration and washed with water. The solids were dissolved into THF. Two volumes of ethyl acetate were added and the organic solution washed with brine, dried over $NaSO_4$, filtered, and concentrated in vacuo to provide a brown solid. The aqueous filtrate was extracted with ethyl acetate and the organic extracts were dried over $NaSO_4$, filtered, and concentrated in vacuo. This material was combined with the previously isolated brown solid and the combined material subjected to column chromatography (dichloromethane, followed by 20:1 dichloromethane/methanol). The desired product (29) was isolated as a light yellow solid (0.752 g, 64%). MS (APCI+) m/z 414, 416, 418 (M+; Cl, Br pattern) detected.

Step I. Preparation of 7-(4-Bromo-2-chloro-phenylamino)-8-chloro-imidazo[1,2-a]pyridine-6-carboxylic acid (30): Sodium hydroxide (1.0 M aqueous solution, 14.6 mL, 14.6 mmol) was added to a solution of 7-(4-bromo-2-chloro-phenylamino)-8-chloro-imidazo[1,2-a]pyridine-6-carboxylic acid methyl ester (29) in methanol (30 mL) and the solution allowed to stir at room temperature overnight. Methanol was removed by rotary evaporation and the solution diluted with water and acidified to pH 2 by addition of 1.0 M HCl. The aqueous suspension was extracted with 4:1 ethyl acetate/THF. The organic extracts were washed with brine, dried over $NaSO_4$, filtered, and concentrated in vacuo to provide the desired product as a light orange solid (30). MS (APCI+) m/z 400, 402, 404 (M+: Cl, Br pattern) detected: $^1$H NMR (400 MHz, methanol-$d_4$) δ 9.01 (s, 1H), 7.83 (s, 1H), 7.51 (s, 2H), 7.25 (d, 1H), 6.60 (d, 1H).

Example 10

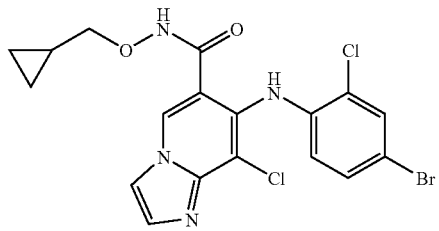

Synthesis of 7-(4-bromo-2-chlorophenylamino)-8-chloroimidazo[1,2-a]pyridine-6-carboxylic acid cyclopropylmethoxyamide (31)

Figure 8:
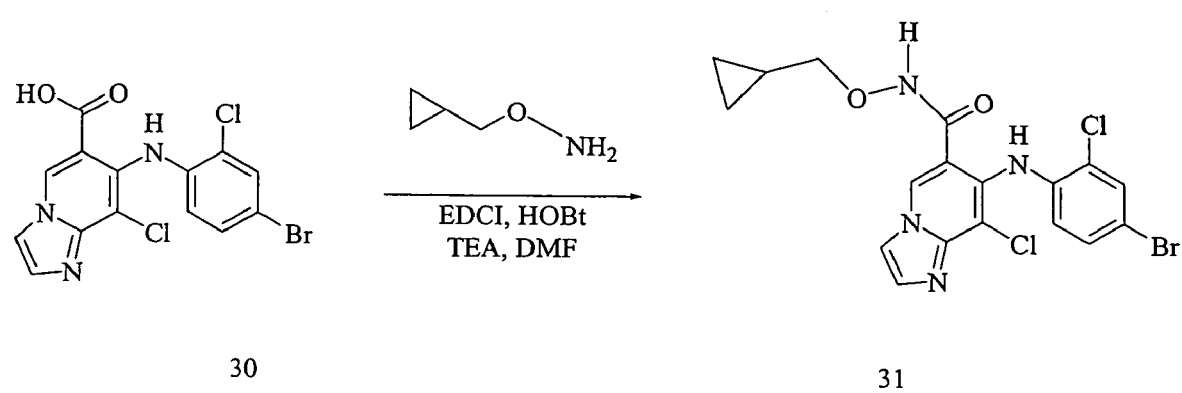
FIG. 8 shows a reaction scheme for the synthesis of compound 31.

FIG. 8 shows the reaction scheme for the synthesis of compound 31, which was prepared according to the method of Example 2, using 7-(4-bromo-2-chlorophenylamino)-8-chloroimidazo[1,2-a]pyridine-6-carboxylic acid (30) as the starting material to provide 4.1 g (53% yield) of compound 31. MS (APCI−) m/z 467, 469, 471 (M−: Cl, Br pattern) detected: $^1$H NMR (400 MHz, methanol-$d_4$) δ 8.76 (s, 1H), 7.95 (d, 1H), 7.64 (d, 1H), 7.56 (d, 1H), 7.26 (dd, 1H), 6.56 (d, 1H), 3.57 (d, 2H), 1.10 (m, 1H), 0.54 (m, 2H), 0.24 (m, 2H).

Figure 9:
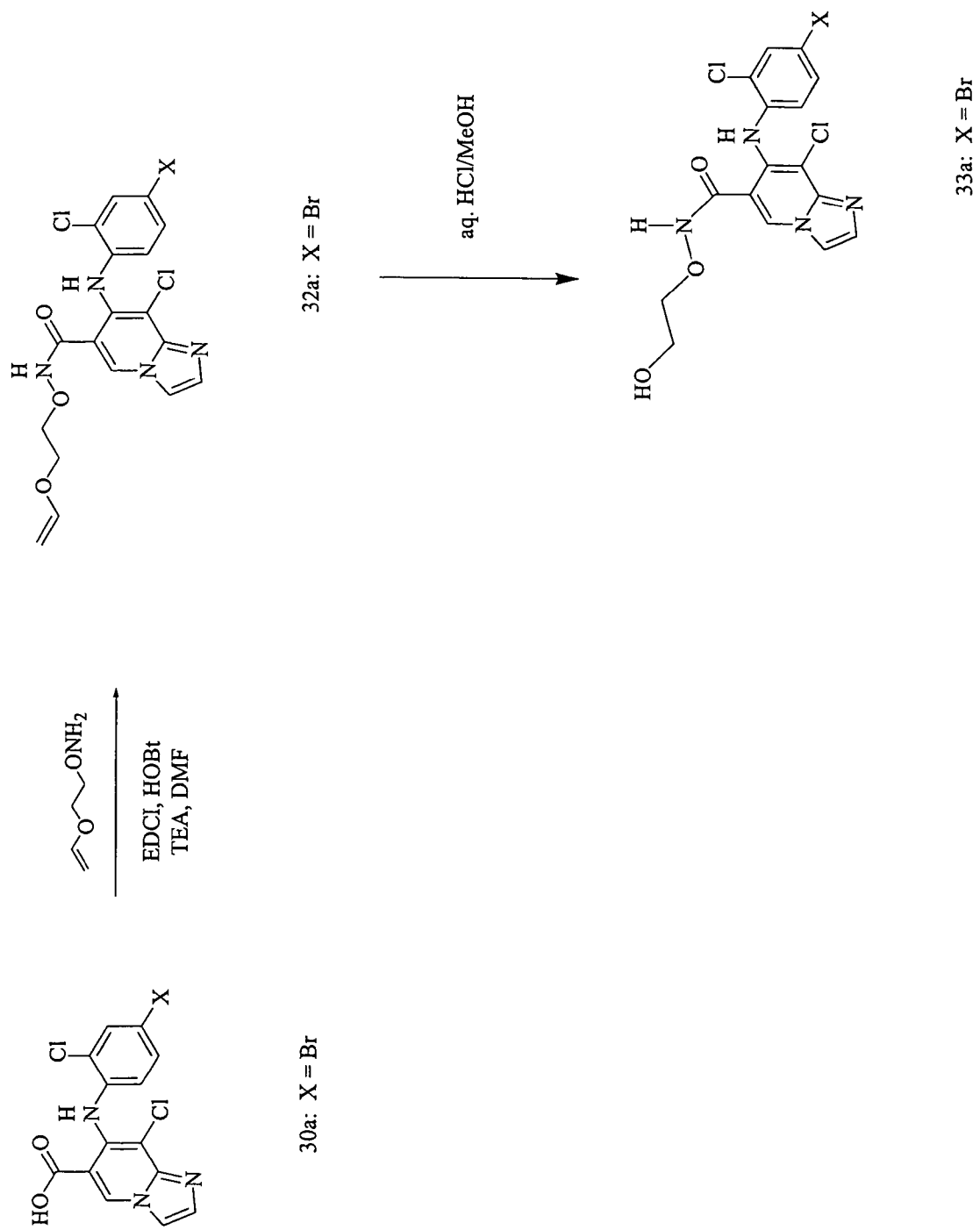

The following compounds were synthesized in a similar manner as shown in FIGS. 7, 8, and 9 using the appropriate aniline in Step C of Example 9.

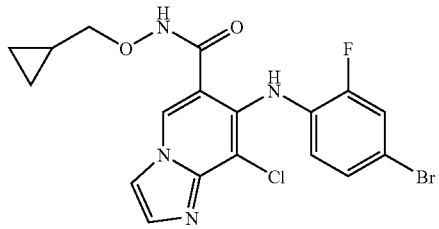

7-(4-Bromo-2-fluorophenylamino)-8-chloroimidazo[1,2-a]pyridine-6-carboxylic acid cyclopropylmethoxyamide MS ESI (+) m/z 453, 455, 457 (M+, Cl, Br pattern) detected. $^1$H NMR (400 MHz, $CD_3OD$) δ 8.70 (s, 1H), 7.95 (s, 1H), 7.67 (s, 1H), 7.34 (m, 1H), 7.20 (m, 1), 6.79 (m, 1H), 3.49 (m, 2H), 1.08 (m, 1H), 0.55 (m, 2H), 0.26 (m, 2H). $^{19}$F NMR (376 MHz, $CD_3OD$) δ-127.4.

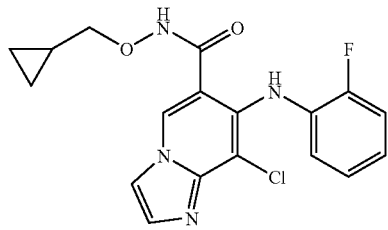

Synthesis of 8-chloro-7-(2-fluorophenylamino)-imidazo[1,2-a]pyridine-6-carboxylic acid cyclopropylmethoxy-amide MS ESI (+) m/z 375, 377 (M+, Cl pattern) detected. $^1$H NMR (400 MHz, CD$_3$OD) δ 8.70 (s, 1H), 7.91 (s, 1H), 7.60 (s, 1H), 7.09 (m, 1H), 7.00 (m, 1H), 6.95 (m, 1H), 6.77 (m, 1H), 3.47 (d, 2H), 1.05 (m, 1H), 0.51 (m, 2H), 0.22 (m, 2H). $^{19}$F NMR (376 MHz, CD$_3$OD) δ-132.1.

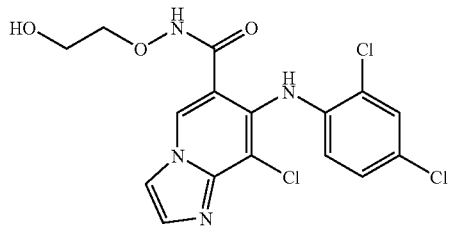

Synthesis of 8-chloro-7-(2,4-dichlorophenylamino)-imidazo[1,2-a]pyridine-6-carboxylic acid (2-hydroxyethoxy) amide MS APCI (−) m/z 413, 415, 417 (M−, Cl pattern) detected: $^1$H NMR (400 MHz, CD$_3$OD) δ 8.78 (s, 1H), 7.90 (s, 1H), 7.87 (s, 1H), 7.10 (dd, 1H), 6.61 (d, 1H), 4.0 (m, 2H), 3.72 (m, 2H).

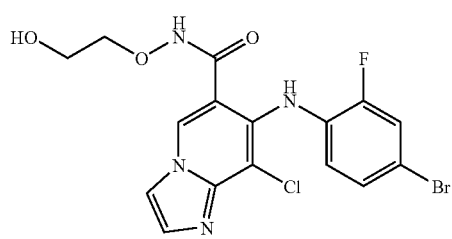

Synthesis of 7-(4-bromo-2-fluor-phenylamino)-8-chloroimidazo[1,2-a]pyridine-6-carboxylic acid (2-hydroxyethoxy)-amide MS ESI (+) m/z 443, 445, 447 (M+, Cl, Br pattern) detected. $^1$H NMR (400 MHz, CD$_3$OD) δ 8.74 (s, 1H), 7.91 (s, 1H), 7.61 (s, 1H), 7.32 (m, 1H), 7.16 (m, 1H), 6.68 (m, 1H), 3.84 (t, 2H), 3.66 (t, 2H). $^{19}$F NMR (376 MHz, CD$_3$OD) δ-128.9.

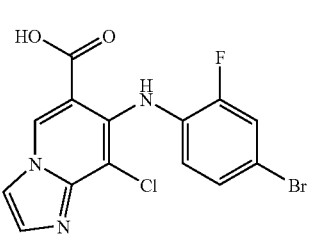

7-(4-Bromo-2-fluorophenylamino)-8-chloro-imidazo[1,2-a]pyridine-6-carboxylic acid MS ESI (+) m/z 384, 386, 388 (M+, Cl, Br pattern) detected. $^1$H NMR (400 MHz, DMSO-d6) δ 9.29 (s, 1H), 8.10 (s, 1H), 7.68 (s, 1H), 7.53 (m, 1H), 7.23 (m, 1H), 6.75 (m, 1H). $^{19}$F NMR (376 MHz, DMSO-d6) δ-127.9.

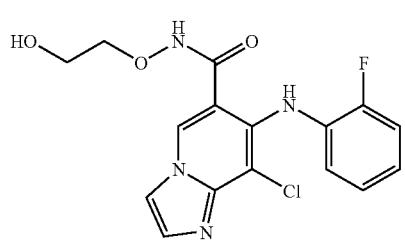

8-Chloro-7-(2-fluorophenylamino)-imidazo[1,2-a]pyridine-6-carboxylic acid (2-hydroxyethoxy)-amide MS ESI (+) m/z 365, 367 (M+, Cl pattern) detected. $^1$H NMR (400 MHz, CD$_3$OD) δ 8.73 (s, 1H), 7.89 (s, 1H), 7.59 (s, 1H), 7.10 (m, 1H), 7.00 (m, 1H), 6.94 (m, 1H), 6.77 (m, 1H), 3.78 (t, 2H), 3.62 (t, 2H). $^{19}$F NMR (376 MHz, CD$_3$OD) δ-131.9.

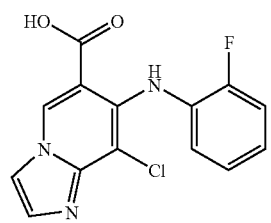

8-Chloro-7-(2-fluorophenylamino)-imidazo[1,2-a]pyridine-6-carboxylic acid

MS ESI (+) m/z 306, 308 (M+, Cl pattern) detected. $^1$H NMR (400 MHz, DMSO-d6) δ 9.30 (s, 1H), 8.09 (s, 1H), 7.67 (s, 1H), 7.22 (dd, 1H), 7.06 (dd, 1H), 6.98 (m, 1H), 6.84 (m, 1H). $^{19}$F NMR (376 MHz, DMSO-d6) δ-130.5.

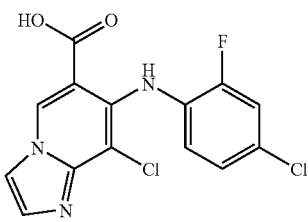

8-Chloro-7-(4-chloro-2-fluorophenylamino)-imidazo[1,2-a]pyridine-6-carboxylic acid MS ESI (+) m/z 340, 342 (M+, Cl pattern) detected. $^1$H NMR (400 MHz, DMSO-d$_6$) δ 9.29 (s, 1H), 8.10 (s, 1H). 7.68 (s, 1H), 7.43 (m, 1H), 7.12 (m, 1H), 6.83 (m, 1H). $^{19}$F NMR (376 MHz, DMSO-d$_6$) δ-127.8.

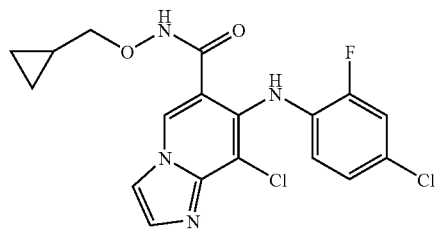

8-Chloro-7-(4-chloro-2-fluorophenylamino)-imidazo[1,2-a]pyridine-6-carboxylic acid cyclopropyl-methoxyamide MS ESI (+) m/z 409, 411 (M+, Cl pattern) detected. $^1$H NMR (400 MHz, CD$_3$OD) δ 9.97 (br s, 1H), 8.82 (s, 1H). 7.73 (s, 1H), 7.71 (s, 1H), 7.18 (m, 1H), 6.97 (m, 1H), 6.56 (m, 1H), 6.47 (br s, 1H), 3.60 (m, 2H), 1.00 (m, 1H), 0.56 (m, 2H), 0.24 (m, 2H). $^{19}$F NMR (376 MHz, CD$_3$OD) δ-128.7.

Example 11

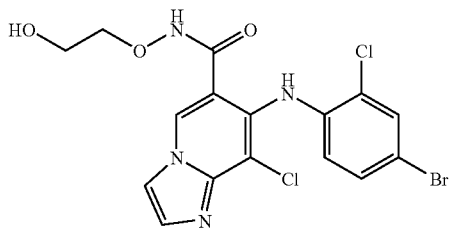

Synthesis of 7-(4-bromo-2-chlorophenylamino)-8-chloroimidazo[1,2-a]pyridine-6-carboxylic acid (2-hydroxyethoxy)-amide (33a)

The reaction scheme for the synthesis of compound 33a is shown in FIG. 9, which was prepared according to Steps A and B of Example 3 using 7-(4-bromo-2-chlorophenylamino)-8-chloroimidazo[1,2-a]pyridine-6-carboxylic acid (30) to provide 44 mg (40% yield for two steps) of the desired product. MS (APCI+) m/z 459, 461, 463 (M+: Cl, Br pattern) detected: $^1$H NMR (400 MHz, methanol-d$_4$) δ 8.90 (s, 1H), 8.08 (s, 1H), 7.93 (s, 1H), 7.69 (s, 1H), 7.45, (d, 1H), 7.06 (m, 1H), 3.86 (br s, 2H), 3.72 (br s, 2H).

Example 12

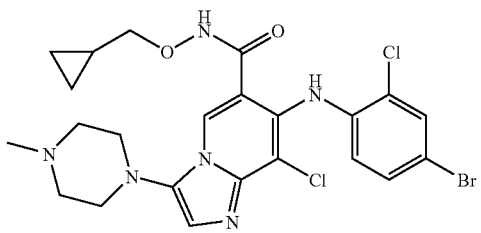

Synthesis of 7-(4-bromo-2-chlorophenylamino)-8-chloro-3-(4-methylpiperazin-1-yl)-imidazo[1,2-a]pyridine-6-carboxylic acid cyclopropylmethoxyamide (36)

Figure 10:
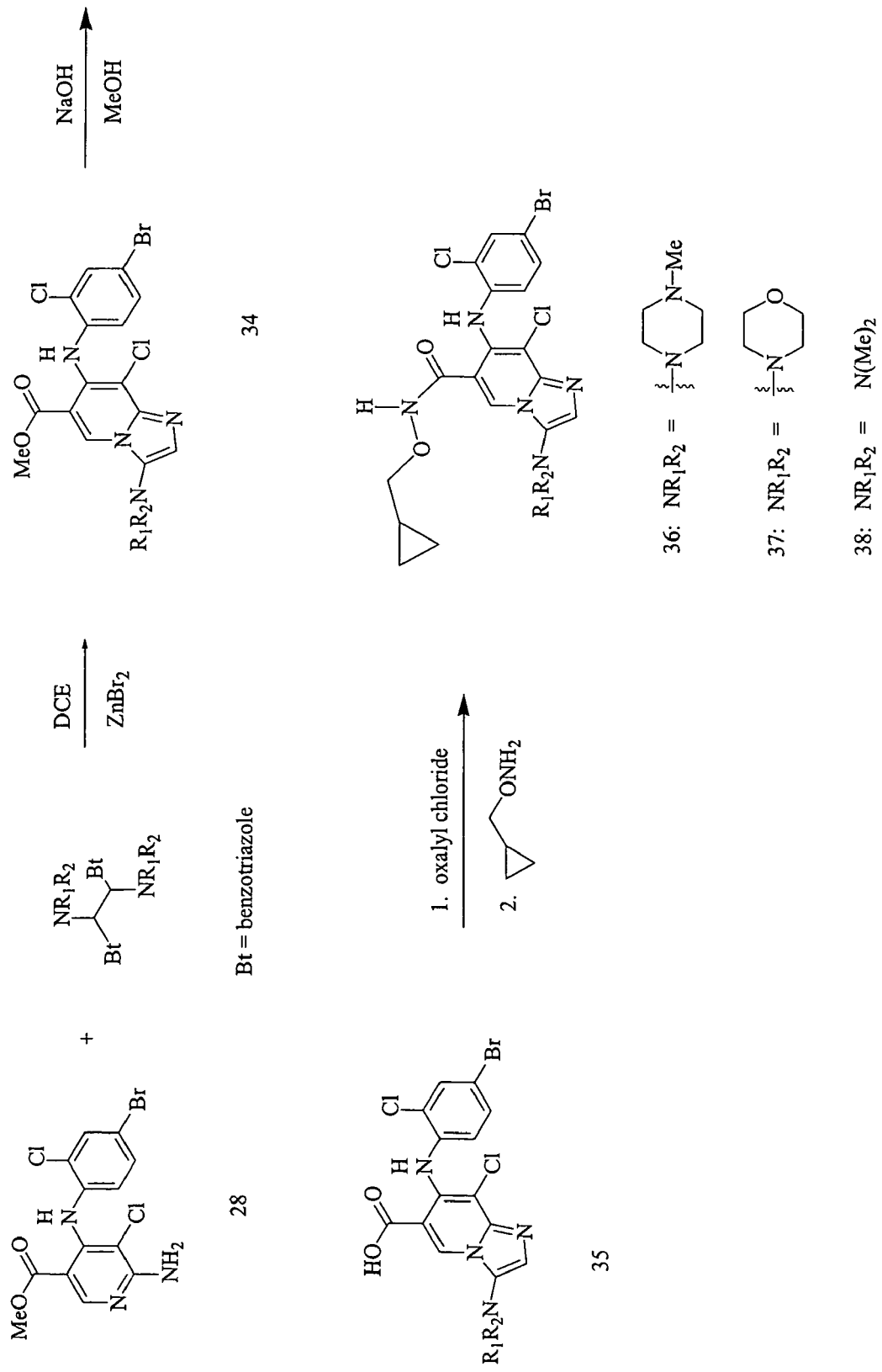
FIG. 10 shows a reaction scheme for the synthesis of compounds 36-38.

The reaction scheme for the synthesis of compound 36 is shown in FIG. 10.

Step A: 7-(4-Bromo-2-chlorophenylamino)-8-chloro-3-(4-methylpiperazin-1-yl)-imidazo[1,2-a]pyridine-6-carboxylic acid methyl ester (34): Preparation was accomplished by modification of the procedure of Katritzky et al. (*J. Org. Chem.*, 2003, 68, 4935-4937: *J. Org. Chem.*, 1990, 55, 3209-3213). Bis(benzotriazazole) adduct (formed with 1-methylpiperazine) (106 mg, 0.230 mmol) was added to a suspension of 6-amino-4-(4-bromo-2-chlorophenylamino)-5-chloronicotinic acid methyl ester (28) (30 mg, 0.076 mmol) in dichloroethylene (1 mL) followed by the addition of ZnBr$_2$ (52 mg, 0.230 mmol). The reaction mixture was stirred at reflux for 10 hours and then at room temperature for 16 hours. The reaction mixture was diluted with CH$_2$Cl$_2$ and filtered. The filtrate was washed with water. The aqueous layer was extracted with CH$_2$Cl$_2$. The combined organic extracts were washed with brine, dried (Na$_2$SO$_4$) and concentrated. Purification by flash column chromatography using the Biotage system (60:1 CH$_2$Cl$_2$:MeOH) provided the desired product (34) as a yellow solid (31 mg, 79%).

Step B: 7-(4-Bromo-2-chlorophenylamino)-8-chloro-3-(4-methylpiperazin-1-yl)-imidazo[1,2-a]pyridine-6-carboxylic acid cyclopropylmethoxyamide (36): Sodium hydroxide (59 μL, 1 M solution) was added to a suspension of 7-(4-bromo-2-chlorophenylamino)-8-chloro-3-(4-methylpiperazin-1-yl)-imidazo[1,2-a]pyridine-6-carboxylic acid methyl ester (34) in MeOH (1 mL). After stirring 18 hours, the reaction mixture was concentrated to dryness. The residue (35) was diluted with toluene and concentrated (repeated), and 31 mg of the recovered yellow residue (35) was carried forward without purification. The residue (35) was suspended in CH$_2$Cl$_2$ (1 mL), cooled to 0° C. and oxalyl chloride (150 μL of a 2 M solution in CH$_2$Cl$_2$) was added. One drop of DMF was added and the reaction mixture warmed to room temperature. After 10 minutes, concentration of the mixture was followed by concentrating from toluene twice and then drying in vacuo. The resulting yellow solid was suspended in CH$_2$Cl$_2$ (1 mL), cooled to 0° C. and cyclopropylmethylhydroxylamine (16 mg, 0.180 mmol) was added. After the reaction mixture was warmed to room temperature and stirred for 16 hours, it was diluted with EtOAc. The organic layer was washed with saturated NaHCO$_3$ and brine, dried (Na$_2$SO$_4$)

Example 13

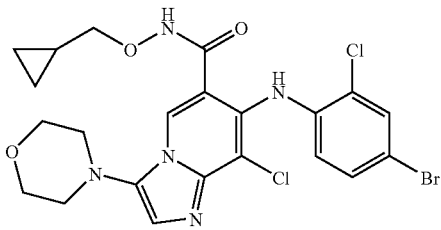

Synthesis of 7-(4-bromo-2-chlorophenylamino)-8-chloro-3-morpholin-4-yl-imidazo[1,2-a]-pyridine-6-carboxylic acid cyclopropylmethoxyamide (37)

The reaction scheme for the synthesis of compound 37 is shown in FIG. 10. Compound 37 was prepared according to Steps A and B of Example 12 using 6-amino-4-(4-bromo-2-chlorophenylamino)-5-chloronicotinic acid methyl ester (28) and the bis(benzotriazazole) adduct (formed with morpholine) to provide 2 mg (8% yield for two steps) of the desired product (37). MS ESI (+) m/z 554, 556, 558 (M+, Cl, Br pattern) detected: $^1$H NMR (400 MHz, CD$_3$OD) δ 8.41 (s, 1H), 7.55 (d, 1H), 7.38 (s, 1H), 7.26 (dd, 1H), 6.54 (d, 1H), 3.91 (t, 4H), 3.59 (d, 2H), 3.11 (t, 4H), 1.08 (m, 1H), 0.54 (m, 2H), 0.24 (m, 2H).

Example 14

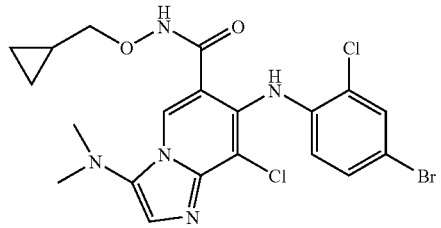

Synthesis of 7-(4-bromo-2-chlorophenylamino)-8-chloro-3-dimethylaminoimidazo[1,2-a]pyridine-6-carboxylic acid cyclopropylmethoxyamide (38)

The reaction scheme for the synthesis of compound 38 is shown in FIG. 10. Compound 38 was prepared according to Steps A and B of Example 12 using 6-amino-4-(4-bromo-2-chlorophenylamino)-5-chloronicotinic acid methyl ester (28) and the bis(benzotriazazole) adduct (formed with dimethylamine) providing 16 mg (37% yield for two steps) of the desired product (38). MS ESI (+) m/z 512, 514, 516 (M+, Cl, Br pattern) detected: $^1$H NMR (400 MHz, CD$_3$OD) δ 8.37 (s, 1H), 7.54 (d, 1H), 7.30 (s, 1H), 7.24 (dd, 1H), 6.52 (d, 1H), 3.59 (d, 2H), 2.86 (s, 6H), 1.07 (m, 1H), 0.53 (m, 2H), 0.23 (m, 2H).

Example 15

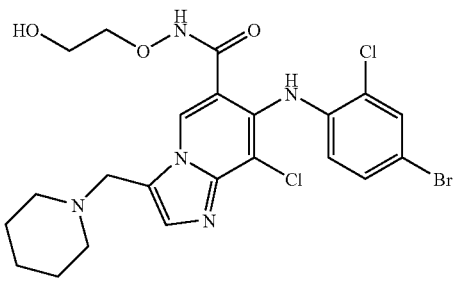

Synthesis of 7-(4-bromo-2-chlorophenylamino)-8-chloro-3-piperidin-1-ylmethylimidazo[1,2-a]pyridine-6-carboxylic acid (2-hydroxyethoxy) amide (39)

Figure 11:
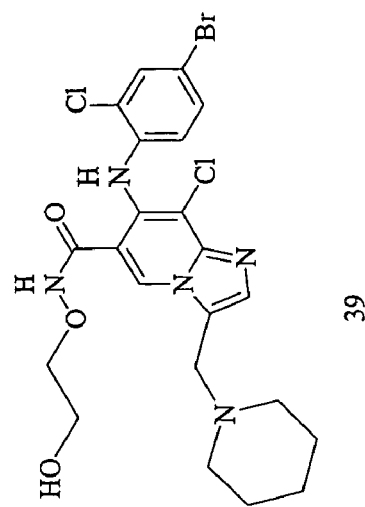
FIG. 11 shows a reaction scheme for the synthesis of compound 39.
Figure 11:
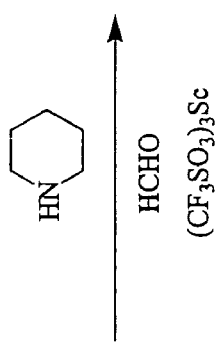
Figure 11:
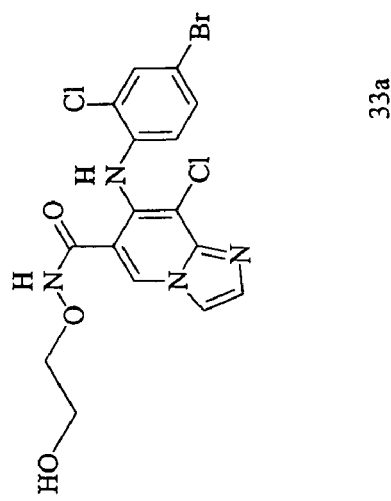

The reaction scheme for the synthesis of compound 39 is shown in FIG. 11. Compound 39 was prepared by a modification of the procedure of Kercher et al. (manuscript in preparation). Piperidine (4 μL, 0.043 mmol) and 37% aqueous formaldehyde (5 μL, 0.065 mmol) were dissolved in 6:1 MeCN:water (0.5 ml), and stirred 30 minutes. 7-(4-bromo-2-chlorophenylamino)-8-chloroimidazo[1,2-a]pyridine-6-carboxylic acid (2-hydroxyethoxy)amide (33a) (10 mg, 0.022 mmol) was added followed by scandium triflate (1 mg, 0.002 mmol). After stirring 16 hours, additional scandium triflate (1 mg), piperidine (3.8 μL) and aqueous formaldehyde (3.8 μL) were added. After about 60 hours, the reaction mixture was diluted with EtOAc and washed with water, 10% K$_2$CO$_3$, and brine. The organic layer was dried (Na$_2$SO$_4$) and concentrated. Purification by flash column chromatography using the Biotage system (40:1 CH$_2$Cl$_2$:MeOH to 20:1 CH$_2$Cl$_2$:MeOH to 9:1 CH$_2$Cl$_2$:MeOH) provided the desired product (39) as a white solid (6 mg, 50%). MS APCI (+) m/z 556, 558, 560 (M+, Cl, Br pattern) detected: $^1$H NMR (400 MHz, CD$_3$OD) δ 8.83 (s, 1H), 7.56 (s, 1H), 7.54 (s, 1H), 7.27 (dd, 1H), 6.56 (d, 1H), 3.91 (m, 4H), 3.70 (m, 2H), 2.51 (broad s, 4H), 1.60 (broad s, 4H), 1.50 (broad s, 2H).

The following compounds were synthesized in a similar manner as shown in FIG. 11.

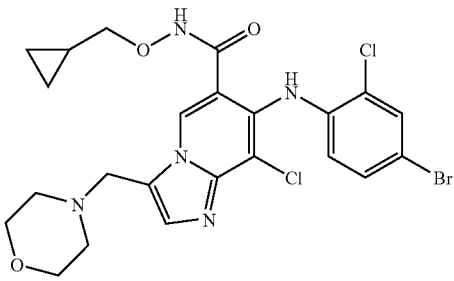

7-(4-Bromo-2-chlorophenylamino)-8-chloro-3-morpholin-4-ylmethyl-imidazo [1,2-a]pyridine-6-carboxylic acid cyclopropylmethoxy-amide The reaction scheme for the synthesis of 7-(4-bromo-2-chlorophenylamino)-8-chloro-3-morpholin-4-ylmethyl-imidazo[1,2-a]pyridine-6-carboxylic acid cyclopropylmethoxyamide is similar to that shown in FIG. 11 using 7-(4-bromo-2-chlorophenylamino)-8-chloroimidazo[1,2-a]pyridine-6-carboxylic acid (2-hydroxyethoxy)amide (33a) and morpholine to provide the desired product. MS APCI (+) m/z 568, 570, 572 (M+, Cl, Br pattern) detected; $^1$H NMR (400 MHz, CDCl$_3$) δ 8.76 (s, 1H), 8.04 (s, 1H), 7.56 (d, 1H), 7.21 (dd, 1H), 6.68 (d, 1H), 4.51 (s, 2H), 4.00 (m, 4H), 3.78 (d, 2H), 1.68 (m, 1H), 0.56 (m, 2H), 0.26 (m, 2H).

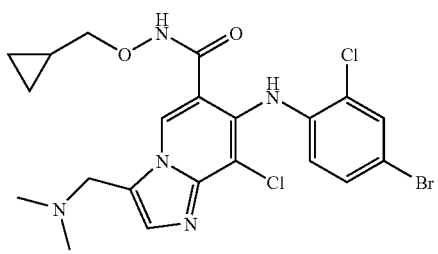

7-(4-Bromo-2-chlor-phenylamino)-8-chloro-3-dimethylaminomethyl-imidazo[1,2-a]pyridine-6-carboxylic acid cyclopropylmethoxyamide The reaction scheme for the synthesis of 7-(4-bromo-2-chlor-phenylamino)-8-chloro-3-dimethylaminomethyl-imidazo[1,2-a]pyridine-6-carboxylic acid cyclopropylmethoxyamide was similar to that shown in FIG. 11, using 7-(4-bromo-2-chlorophenylamino)-8-chloroimidazo[1,2-a]pyridine-6-carboxylic acid (2-hydroxyethoxy)amide (33a) and dimethylamine to provide the desired product. MS APCI (+) m/z 528, 530, 532 (M+, Cl, Br pattern) detected; $^1$H NMR (400 MHz, CD$_3$OD) δ 8.71 (s, 1H), 7.50 (d, 1H), 7.44 (s, 1H), 7.20 (dd, 1H), 6.55 (d, 1H), 3.80 (s, 2H), 3.74 (d, 2H), 2.04 (s, 6H), 1.18 (m, 1H), 0.51 (m, 2H), 0.27 (m, 2H).

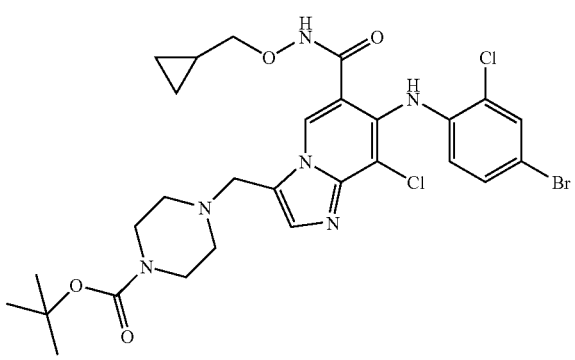

4-[7-(4-Bromo-2-chlorophenylamino)-8-chloro-6-cyclopropylmethoxycarbamoylimidazo[1,2-a]pyridin-3-ylmethyl]-piperazine-1-carboxylic acid tert-butyl ester The reaction scheme for the synthesis of 4-[7-(4-bromo-2-chlorophenylamino)-8-chloro-6-cyclopropylmethoxycarbamoylimidazo[1,2-a]pyridin-3-ylmethyl]-piperazine-1-carboxylic acid tert-butyl ester was similar to that shown in FIG. 11, using 7-(4-bromo-2-chlorophenylamino)-8-chloroimidazo[1,2-a]pyridine-6-carboxylic acid (2-hydroxyethoxy)amide (33a) and piperazine-1-carboxylic acid tert-butyl ester to provide the desired product. MS APCI (+) m/z 669, 671, 673 (M+, Cl, Br pattern) detected; $^1$H NMR (400 MHz, CDCl$_3$) δ 8.80 (s, 1H), 8.00 (s, 1H), 7.56 (d, 1H), 7.27 (dd, 1H), 6.67 (d, 1H), 4.54 (s, 2H), 3.76 (d, 4H), 3.27 (m, 4H), 1.50 (s, 9H), 1.12 (m, 1H), 0.55 (m, 2H), 0.28 (m, 2H).

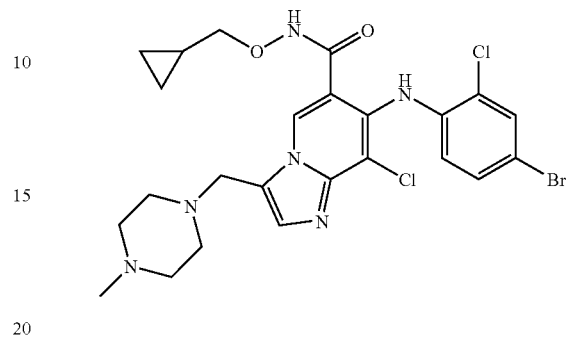

7-(4-Bromo-2-chlorophenylamino)-8-chloro-3-(4-methylpiperazin-1-ylmethyl)-imidazo[1,2-a]pyridine-6-carboxylic acid cyclopropylmethoxyamide The reaction scheme for the synthesis of 7-(4-bromo-2-chlorophenylamino)-8-chloro-3-(4-methylpiperazin-1-ylmethyl)-imidazo[1,2-a]pyridine-6-carboxylic acid cyclopropylmethoxyamide was similar to that shown in FIG. 11 using 7-(4-bromo-2-chlorophenylamino)-8-chloroimidazo[1,2-a]pyridine-6-carboxylic acid (2-hydroxyethoxy)amide (33a) and 1-methylpiperazine to provide the desired product. MS APCI (+) m/z 581, 583, 585 (M+, Cl, Br pattern) detected; $^1$H NMR (400 MHz, CDCl$_3$) δ 8.90 (s, 1H), 7.57 (s, 1H), 7.56 (d, 1H), 7.22 (dd, 1H), 6.47 (d, 1H), 3.83 (s, 2H), 3.60 (d, 2H), 2.47 (m, 8H), 2.31 (s, 3H), 1.02 (m, 1H), 0.56 (m, 2H), 0.26 (m, 2H).

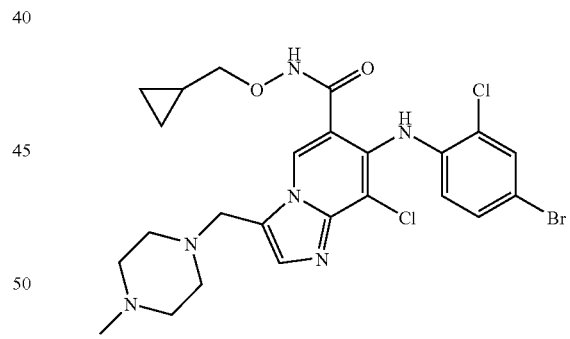

7-(4-Bromo-2-chlorophenylamino)-8-chloro-3-(4-methylpiperazin-1-ylmethyl)-imidazo[1,2-a]pyridine-6-carboxylic acid cyclopropylmethoxyamide 7-(4-Bromo-2-chlorophenylamino)-8-chloro-3-(4-methylpiperazin-1-ylmethyl)-imidazo[1,2-a]pyridine-6-carboxylic acid cyclopropylmethoxyamide was prepared using 7-(4-bromo-2-chlorophenylamino)-8-chloroimidazo[1,2-a]pyridine-6-carboxylic acid (2-hydroxyethoxy)amide (33a) and 1-methyl-piperazine to provide the desired product. MS APCI (+) m/z 581, 583, 585 (M+, Cl, Br pattern) detected; $^1$H NMR (400 MHz, CDCl$_3$) δ 8.90 (s, 1H), 7.57 (s, 1H), 7.56 (d, 1H), 7.22 (dd, 1H), 6.47 (d, 1H), 3.83 (s, 2H), 3.60 (d, 2H), 2.47 (m, 8H), 2.31 (s, 3H), 1.02 (m, 1H), 0.56 (m, 2H), 0.26 (m, 2H).

Example 16

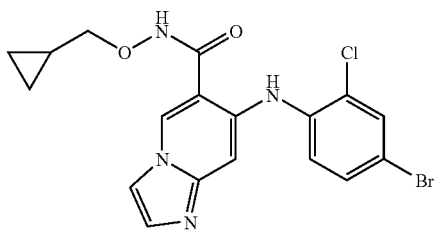

Synthesis of 7-(4-bromo-2-chlorophenylamino)-imidazo[1,2-a]pyridine-6-carboxylic acid cyclopropylmethoxyamide (44a)

Figure 12:
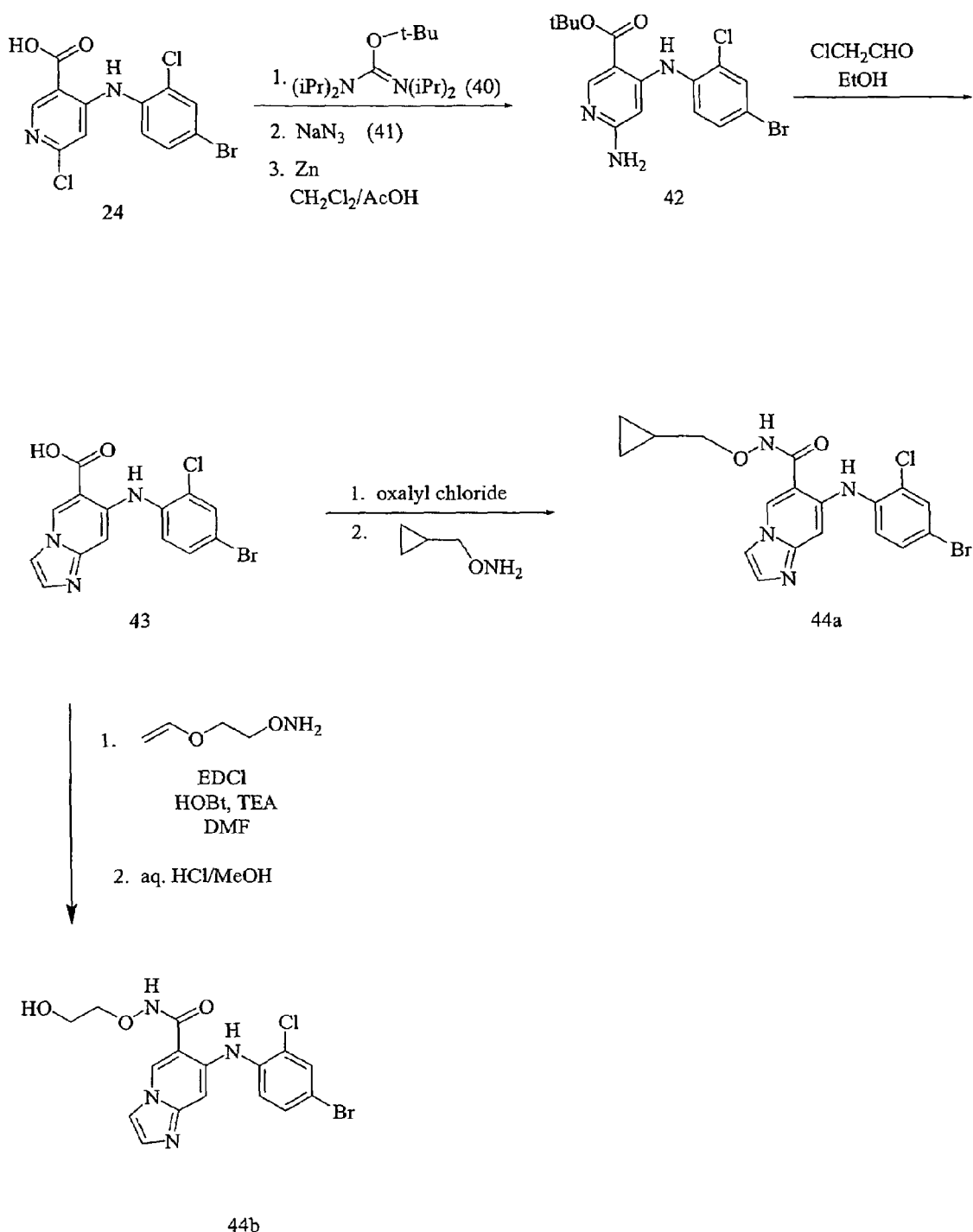
FIG. 12 shows a reaction scheme for the synthesis of compounds 44a and 44b.

The reaction scheme for the synthesis of compound 44a is shown in FIG. 12.

Step A: Preparation of 4-(4-bromo-2-chlorophenylamino)-6-chloronicotinic acid tert-butyl ester (40): 2-tert-Butyl-1,3-diisopropylisourea (8.04 g, 40.1 mmol) was added to a mixture of 4-(4-bromo-2-chlorophenylamino)-6-chloronicotinic acid hydrochloride salt (24) (2.91 g, 7.31 mmol) in THF (165 mL). After stirring for 2 hours at room temperature and 30 minutes at reflux, the reaction mixture was cooled to room temperature and diluted with EtOAc. The organic layer was washed with 10% $K_2CO_3$ and brine, dried ($Na_2SO_4$) and concentrated. The resulting residue was dissolved in $CH_2Cl_2$ and filtered. The filtrate was concentrated and purified by flash column chromatography using the Biotage system ($CH_2Cl_2$) to give the desired product (40) (3.28 g, 78%).

Step B: Preparation of 6-azido-4-(4-bromo-2-chlorophenyl-amino)nicotinic acid tert-butyl ester (41): Sodium azide (1.51 g, 23.2 mmol) was added to a mixture of 4-(4-bromo-2-chlorophenylamino)-6-chloronicotinic acid tert-butyl ester (40) (3.23 g, 7.73 mmol) in DMF (60 mL). The reaction mixture was heated to 80° C. and stirred for 16 hours. After cooling to room temperature, the reaction was diluted with EtOAc and washed with water, saturated $NaHCO_3$ and brine. The organic layer was dried ($Na_2SO_4$) and concentrated. Purification by flash column chromatography using the Biotage system ($CH_2Cl_2$) (repeated) provided the desired product (41) (1.41 g, 43%).

Step C: Preparation of 6-amino-4-(4-bromo-2-chlorophenylamino)-nicotinic acid tert-butyl ester (42): Compound 42 was prepared as described in Step G of Example 9 using 6-azido-4-(4-bromo-2-chlorophenylamino)nicotinic acid tert-butyl ester (41).

Step D: Preparation of 7-(4-bromo-2-chlorophenylamino)imidazo[1,2-a]pyridine-6-carboxylic acid (43): Chloroacetaldehyde (12 μL, 0.188 mmol) was added to a mixture of 6-amino-4-(4-bromo-2-chlorophenylamino)-nicotinic acid tert-butyl ester (42) (50 mg, 0.125 mmol) in EtOH (630 μL). After stirring the reaction mixture at 80° C. for 5 hours, an additional 12 μL of chloroacetaldehyde were added and heating was continued for 10 hours. The reaction mixture was cooled to room temperature and diluted with EtOAc to give a cloudy semi-solution. The organic layer was washed with water, saturated $NaHCO_3$ and brine. The organic layer contains a precipitate, which was collected by filtration to give the desired product (43) (15 mg, 33%).

Step E: Preparation of 7-(4-bromo-2-chlorophenylamino)-imidazo[1,2-a]pyridine-6-carboxylic acid cyclopropyl-methoxyamide (44a): Oxalyl chloride (102 μL of a 2.0 M solution in $CH_2Cl_2$) was added to a stirred suspension of 7-(4-bromo-2-chlorophenylamino)imidazo[1,2-a]pyridine-6-carboxylic acid (43) (15 mg, 0.041 mmol) in $CH_2Cl_2$ (1 mL) at 0° C. One drop of DMF was added. The reaction mixture was warmed to room temperature, stirred for 25 minutes, and then concentrated. The residue was twice concentrated from toluene and dried in vacuo. The residue was suspended in $CH_2Cl_2$ (1 mL), cooled to 0° C. and cyclopropylmethylhydroxylamine (36 mg, 0.409 mmol) was added. The reaction mixture was warmed to room temperature, stirred for 2 hours and diluted with EtOAc. The organic layer was washed with saturated $NaHCO_3$ and brine, dried ($Na_2SO_4$) and concentrated. Purification by flash column chromatography using the Biotage system (40:1 $CH_2Cl_2$:MeOH to 20:1 $CH_2Cl_2$:MeOH) provided the desired product (44a) as a tan solid (6 mg, 31%). MS APCI (−) m/z 433, 435 (M−, Cl, Br pattern) detected: $^1$H NMR (400 MHz, $CDCl_3$) δ 8.68 (s, 1H), 7.69 (m, 1H), 7.67 (d, 1H), 7.52-7.44 (m, 3H), 7.08 (s, 1H), 3.83 (d, 2H), 0.90 (m, 1H), 0.62 (m, 2H), 0.35 (m, 2H).

The following compounds were synthesized in a similar manner as shown in FIG. 12 using the appropriate aniline in Step C of Example 9.

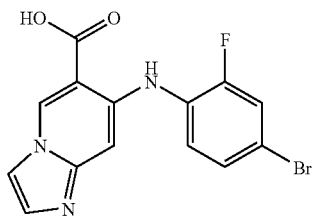

7-(4-Bromo-2-fluorophenylamino)-imidazo[1,2-a]pyridine-6-carboxylic acid

MS ESI (+) m/z 350, 352 (M+, Br pattern) detected. (400 MHz, DMSO-$d_6$) δ 9.13 (s, 1H), 7.94 (d, 1H). 7.70 (dd, 1H), 7.67 (d, 1H), 7.59 (t, 1H), 7.47 (m, 1H), 6.84 (s, 1H). $^{19}$F NMR (376 MHz, DMSO-d6) δ-128.9.

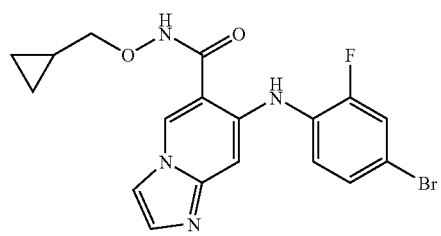

7-(4-Bromo-2-fluorophenylamino)-imidazo[1,2-a]pyridine-6-carboxylic acid cyclopropylmethoxyamide MS ESI (+) m/z 419, 421 (M+, Br pattern) detected. $^1$H NMR (400 MHz, DMSO-d6) δ 11.91 (br s, 1H), 8.79 (s, 1H), 8.72 (br s, 1H), 7.81 (s, 2H), 7.64 (m, 1H), 7.50 (m, 1H), 7.45 (m, 1H), 7.39 (m, 1H), 6.90 (s, 1H), 3.74 (d, 2H), 1.14 (m, 1H), 0.55 (m, 2H), 0.29 (m, 2H). $^{19}$F NMR (376 MHz, DMSO-d6) δ-124.3.

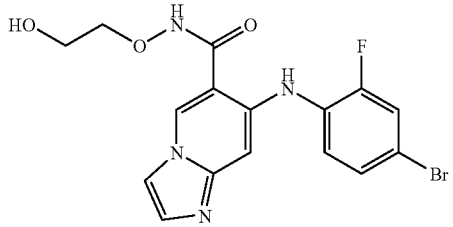

7-(4-bromo-2-fluorophenylamino)-imidazo[1,2-a]pyridine-6-carboxylic acid (2-hydroxyethoxy)-amide MS ESI (+) m/z 409, 411 (M+, Br pattern) detected. $^1$H NMR (400 MHz, DMSO-d$_6$) δ 12.02 (br s, 1H), 8.83 (s, 1H), 7.80 (s, 1H), 7.63 (s, 1H), 7.51 (m, 1H), 7.45 (m, 1H), 7.39 (m, 1H), 6.91 (s, 1H), 4.79 (br s, 1H), 3.94 (t, 2H), 3.64 (t, 2H). $^{19}$F NMR (376 MHz, DMSO-d$_6$) δ-124.4.

Example 17

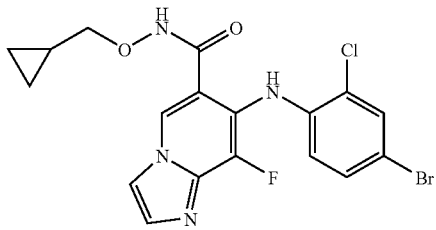

Synthesis of 7-(4-bromo-2-chlorophenylamino)-8-fluoroimidazo[1,2-a]pyridine-6-carboxylic acid cyclopropylmethoxyamide (47a)

Figure 13:
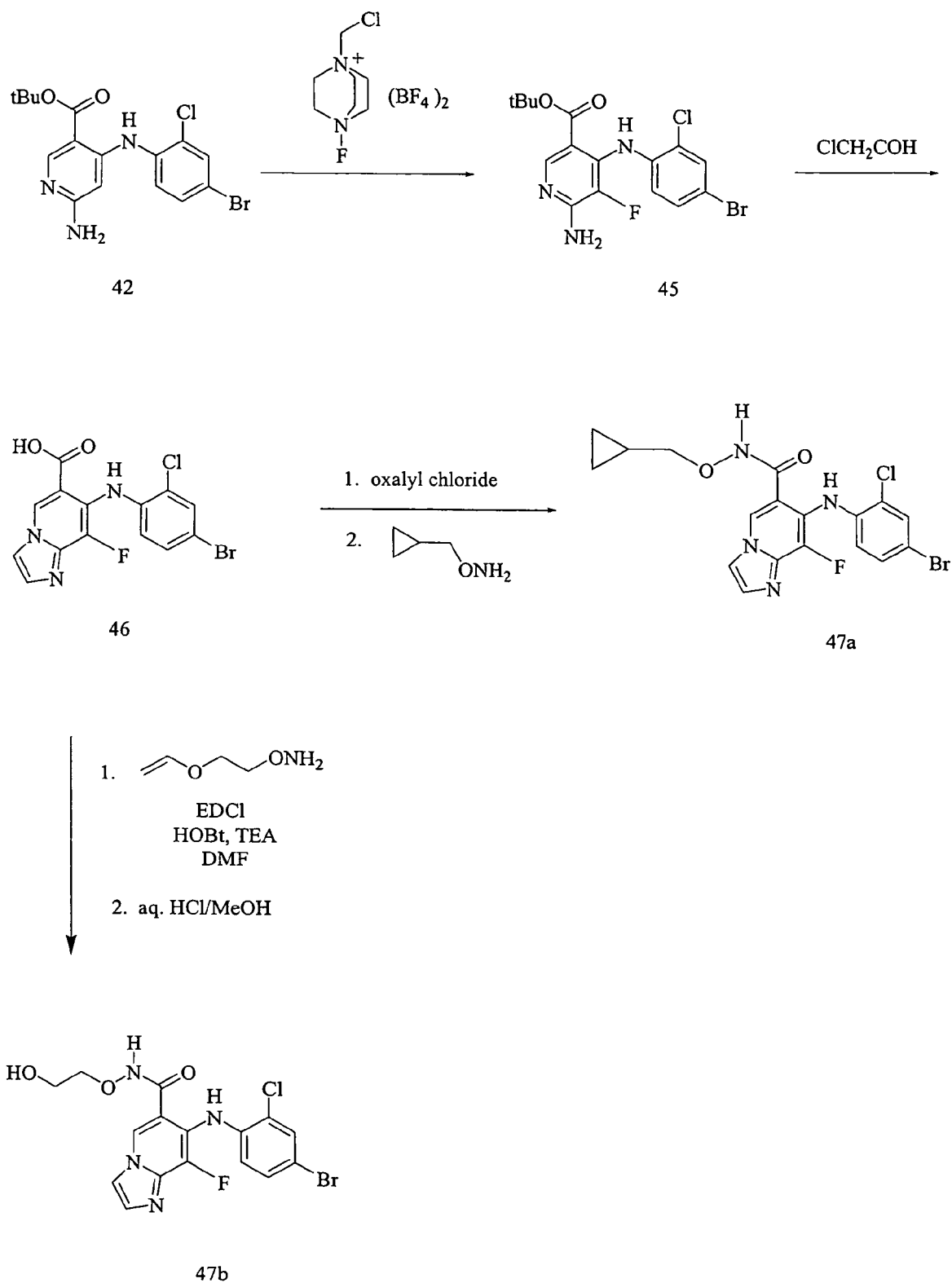
FIG. 13 shows a reaction scheme for the synthesis of compounds 47a and 47b.

The reaction scheme for the synthesis of compound 47a is shown in FIG. 13.

Step A: Preparation of 6-amino-4-(4-bromo-2-chlorophenylamino)-5-fluoronicotinic acid tert-butyl ester (45): 1-Chloromethyl-4-fluoro-1,4-diazoniabicyclo[2.2.2]octane bis(tetrafluoroborate) (889 mg, 2.508 mmol) was added to a mixture of 6-amino-4-(4-bromo-2-chlorophenylamino)nicotinic acid tert-butyl ester (42) (1.00 g, 2.51 mmol) in 1:1 MeOH:water (25 mL). After about 2 hours, the reaction mixture was diluted with EtOAc and water. The layers were separated and the organic layer washed with 0.5 N HCl and brine. The aqueous washes were back extracted with EtOAc. The combined organic extracts were dried (Na$_2$SO$_4$) and concentrated. Purification by flash column chromatography using the Biotage system (20:1 hexanes:EtOAc to 15:1 hexanes:EtOAc) provided the desired product (45) as a yellow solid (75 mg, 7%).

Step B: Preparation of 7-(4-bromo-2-chlorophenylamino)-8-fluoroimidazo[1,2-a]pyridine-6-carboxylic acid (46): Chloroacetaldehyde (23 µL, 0.360 mmol) was added to a mixture of 6-amino-4-(4-bromo-2-chlorophenylamino)-5-fluoronicotinic acid tert-butyl ester (45) (75 mg, 0.180 mmol) in EtOH (1 mL). After stirring the reaction mixture at 70° C for 10 hours, an additional 10 µL chloro-acetaldehyde was added and heating was continued for 33 hours. The reaction mixture was cooled to room temperature and desired product (46) was collected by filtration. The filtrate was diluted with EtOAc and washed with water, saturated NaHCO$_3$ and brine. The organic layer was dried (Na$_2$SO$_4$) and concentrated to give additional product (46) (51 mg, 74% combined recovery).

Step C: Preparation of 7-(4-bromo-2-chlorophenylamino)-8-fluoroimidazo[1,2-a]pyridine-6-carboxylic acid cyclopropylmethoxyamide (47a): Compound 47 was prepared as described in Step E of Example 16 using 7-(4-bromo-2-chlorophenylamino)-8-fluoroimidazo[1,2-a]pyridine-6-carboxylic acid (46) to give 15 mg (24%) of the desired product (47a) as a white solid. MS APCI (+) m/z 453, 455, 457 (M+, Cl, Br pattern) detected: $^1$H NMR (400 MHz, CD$_3$OD) δ 8.66 (s, 1H), 7.93 (m, 1H), 7.61 (s, 1H), 7.56 (d, 1H), 7.32 (dd, 1H), 6.73 (q, 1H) 3.70 (d, 2H), 1.14 (m, 1H), 0.56 (m, 2H), 0.26 (m, 2H): $^{19}$F (400 MHz, CD$_3$OD) –139.4 (s, 1F).

The following compounds were synthesized in a similar manner as shown in FIG. 13.

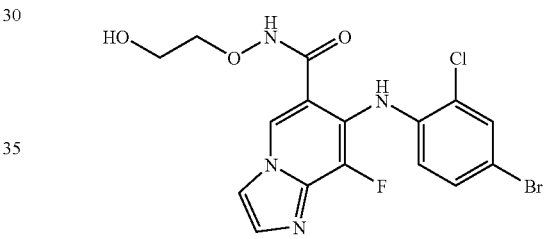

7-(4-Bromo-2-chlorophenylamino)-8-fluoroimidazo[1,2-a]pyridine-6-carboxylic acid (2-hydroxyethoxy)amide MS APCI (+) m/z 443, 445, 447 (M+, Cl, Br pattern) detected; $^1$H NMR (400 MHz, CD$_3$OD) δ 8.69 (s, 1H), 7.89 (m, 1H), 7.59 (s, 1H), 7.55 (d, 1H), 7.31 (dd, 1H), 6.72 (q, 1H), 4.01 (t, 2H), 3.76 (t, 2H); $^{19}$F (400 MHz, CD$_3$OD) –139.7 (s, 1F).

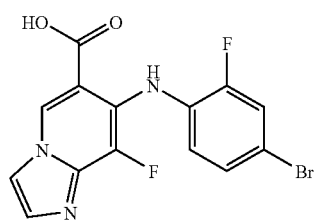

7-(4-Bromo-2-fluorophenylamino)-8-fluoroimidazo[1,2-a]pyridine-6-carboxylic acid MS ESI (+) m/z 368, 370 (M+, Br pattern) detected.

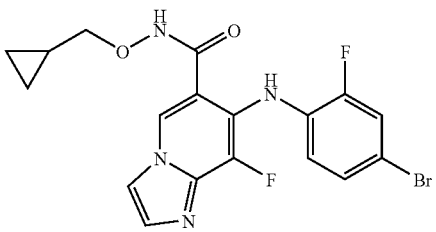

7-(4-Bromo-2-fluorophenylamino)-8-fluoroimidazo[1,2-a]pyridine-6-carboxylic acid cyclopropylmethoxyamide MS ESI (+) m/z 437, 439 (M+, Br pattern) detected. $^1$H NMR (400 MHz, CD$_3$OD) δ 9.55 (br s, 1H), 8.57 (s, 1H). 7.68 (s, 2H), 7.65 (s, 1H), 7.28 (m, 1H), 7.14 (m, 1H), 6.78 (br s, 1H), 6.63 (m, 1H), 3.72 (m, 2H), 1.07 (m, 1H), 0.59 (m, 2H), 0.28 (m, 2H). $^{19}$F NMR (376 MHz, CD$_3$OD) δ-128.9,-138.1.

Example 18

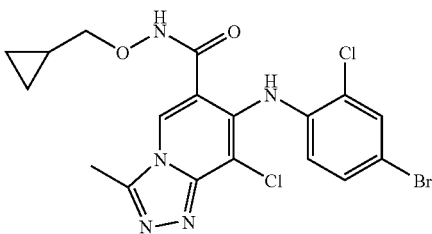

Synthesis of 7-(4-bromo-2-chlorophenylamino)-8-chloro-3-methyl-[1,2,4]-triazolo-[4,3-a]pyridine-6-carboxylic acid cyclopropylmethoxyamide (53a)

The reaction scheme for the synthesis of compound 53a is shown in FIG. 14.

Step A: Preparation of 4-(4-bromo-2-chlorophenylamino)-5-chloro-6-hydrazinonicotinic acid ethyl ester (49): 4-(4-Bromo-2-chlorophenylamino)-5,6-dichloronicotinic acid ethyl ester (48) was prepared by standard methods from 4-(4-bromo-2-chlorophenylamino)-5,6-dichloronicotinic acid. Hydrazine monohydrate (0.59 mL, 12.16 mmol) was added to a solution of 4-(4-bromo-2-chlorophenylamino)-5,6-dichloronicotinic acid ethyl ester (48) (1.72 g, 4.05 mmol) in N,N-dimethylacetamide (20 mL). After stirring at 90° C. for 1 hour, the reaction mixture was cooled to room temperature and diluted with EtOAc. The organic layer was washed with water and brine, dried (Na$_2$SO$_4$) and concentrated. Purification by flash column chromatography using the Biotage system (20:1 CH$_2$Cl$_2$:EtOAc) provided the desired product (49) (307 mg, 18%).

Step B: Preparation of 7-(4-bromo-2-chlorophenylamino)-8-chloro-3-methyl-[1,2,4]triazolo[4,3-a]pyridine-6-carboxylic acid ethyl ester (51a): Acetic anhydride (22 μL, 0.238 mmol) was added to a solution of 4-(4-bromo-2-chlorophenylamino)-5-chloro-6-hydrazinonicotinic acid ethyl ester (49) (0.100 g, 0.238 mmol) and triethylamine (66 μL, 0.476 mmol) in CH$_2$Cl$_2$ (2.5 mL) at 0° C., and then the solution was warmed to room temperature to provide compound 50a (not isolated). After 10 minutes, POCl$_3$ (87 μL, 0.952 mmol) was added dropwise and the reaction mixture was warmed to room temperature. After 16 hours, the reaction mixture was heated to reflux and stirred for 3 days. The reaction mixture was cooled to room temperature and concentrated. The residue was diluted with EtOAc and saturated NaHCO$_3$ was added and the mixture stirred for 20 minutes. The layers were separated and the organic layer was washed with brine. The aqueous washings were back extracted with EtOAc. The combined organic extracts were dried (Na$_2$SO$_4$) and concentrated. Purification by flash column chromatography using the Biotage system (9:1 CH$_2$Cl$_2$:EtOAc) provided compound 51a (80 mg, 75%).

Step C: Preparation of 7-(4-bromo-2-chlorophenylamino)-8-chloro-3-methyl-[1,2,4]triazolo[4,3-a]pyridine-6-carboxylic acid (52a): Sodium hydroxide (715 μL of a 1 M solution) was added to a solution of 7-(4-bromo-2-chlorophenylamino)-8-chloro-3-methyl-[1,2,4]triazolo[4,3-a]pyridine-6-carboxylic acid ethyl ester (51a) (79 mg, 179 mmol) in 3:1 THF:water (4.5 mL). After 16 hours, the reaction mixture was poured into a separatory funnel, diluted with brine and acidified with 1 N HCl to about pH 2. The aqueous layer was extracted with 1:1 EtOAc:THF. The combined organic extracts were dried (Na$_2$SO$_4$) and concentrated and the residue (52a) was carried forward without further purification.

Step D: Preparation of 7-(4-bromo-2-chlorophenylamino)-8-chloro-3-methyl-[1,2,4]triazolo[4,3-a]pyridine-6-carboxylic acid cyclopropylmethoxyamide (53a): Compound 53a was prepared as described in Example 2 using 7-(4-bromo-2-chlorophenylamino)-8-chloro-3-methyl-[1,2,4]triazolo[4,3-a]pyridine-6-carboxylic acid (52a) to give 2 mg (5%) of the desired product. MS APCI (−) m/z 482, 484, 486 (M−, Cl, Br pattern) detected.

Example 19

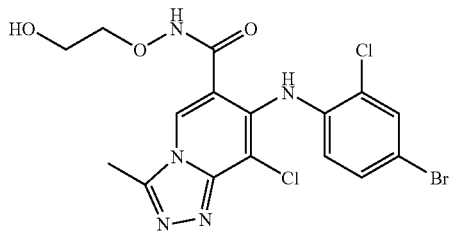

Synthesis of 7-(4-bromo-2-chlorophenylamino)-8-chloro-3-methyl-[1,2,4]triazolo[4,3-a]pyridine-6-carboxylic acid (2-hydroxyethoxy)-amide (54a)

The reaction scheme for the synthesis of compound 54a is shown in FIG. 14. Compound 54a was prepared as described herein starting with 7-(4-bromo-2-chlorophenylamino)-8-chloro-3-methyl-[1,2,4]triazolo[4,3-a]pyridine-6-carboxylic acid (52a) to give 1 mg (2% for the two steps) desired product (54a). MS APCI (−) m/z 472, 474, 476 (M−, Cl, Br pattern) detected.

Example 20

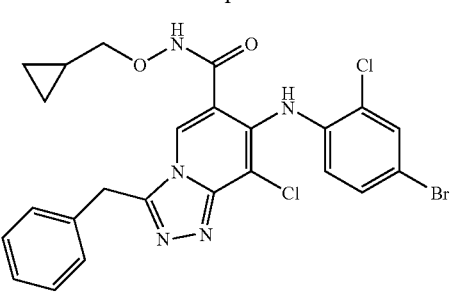

Synthesis of 3-benzyl-7-(4-bromo-2-chlorophenylamino)-8-chloro-[1,2,4]triazolo [4,3-a]pyridine-6-carboxylic acid cyclopropylmethoxyamide (53b)

The reaction scheme for the synthesis of compound 53b is shown in FIG. 14.

Step A: Preparation of 3-benzyl-7-(4-bromo-2-chlorophenylamino)-8-chloro-[1,2,4]triazolo[4,3-a]pyridine-6-carboxylic acid methyl ester (51b): Phenylacetyl chloride (152 μL, 1.148 mmol) was added to a solution of 4-(4-bromo-2-chlorophenylamino)-5-chloro-6-hydrazinonicotinic acid methyl ester (49) (0.233 g, 0.574 mmol) and triethylamine (160 μL, 1.148 mmol) in CH$_2$Cl$_2$ (5.7 mL) at 0° C. After warming to room temperature, an additional 75 μL phenylacetyl chloride was added. After 6 hours, the reaction mixture was concentrated and diluted with EtOAc. The organic layer was washed with water and brine, dried (Na$_2$SO$_4$) and concentrated. The residue (50b) was diluted with dichloroethylene (2 mL) and POCl$_3$ (465 μL, 5.082 mmol) was added. After stirring at reflux for 12 hours, the reaction mixture was cooled to room temperature and concentrated. The residue was diluted with EtOAc and saturated NaHCO$_3$ was added and the mixture stirred for 20 minutes. The resulting solid was collected by filtrate to give the desired product (51b) (97 mg, 30%).

Step B: Preparation of 3-benzyl-7-(4-bromo-2-chlorophenylamino)-8-chloro-[1,2,4]triazolo[4,3-a]pyridine-6-carboxylic acid cyclopropylmethoxyamide (53b): Compound 53b was prepared as described in Step C of Example 18 and Example 2 using 3-benzyl-7-(4-bromo-2-chloro-phenylamino)-8-chloro-[1,2,4]triazolo[4,3-a]pyridine-6-carboxylic acid methyl ester (51b) as the starting material to give 5 mg (4% for the two steps) of the desired product (53b). MS APCI (−) m/z 558, 560, 562 (M−, Cl, Br pattern) detected; $^1$H NMR (400 MHz, CDCl$_3$) δ 8.22 (s, 1H), 7.30 (m, 6H), 6.50 (d, 1H), 4.53 (s, 2H), 3.49 (m, 2H), 0.94 (m, 1H), 0.51 (m, 2H), 0.19 (m, 2H).

Example 21

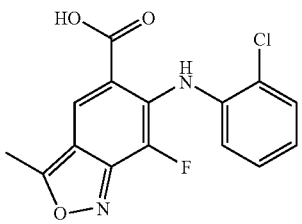

Synthesis of 6-(2-chlorophenylamino)-7-fluoro-3-methylbenzo[c]isoxazole-5-carboxylic acid (56)

The synthesis of compound 56 is shown in FIG. 15.

Step A: Preparation of 6-(2-chlorophenylamino)-7-fluoro-3-methyl-benzo[c]-isoxazole-5-carboxylic acid methyl ester (55): Sodium azide (128 mg, 1.95 mmol) was added to a mixture of 5-acetyl-2-(2-chlorophenylamino)-3,4-difluorobenzoic acid methyl ester (6) (601 mg, 1.59 mmol) in 3:1 acetone:water (16 ml) and heated to reflux. After 16 hours, the reaction mixture was cooled to room temperature, and diluted with EtOAc and water. The organic layer was washed with water, dried (MgSO$_4$) and concentrated. The resulting residue was diluted with water (8 mL) and heated to reflux. After 5 hours, the mixture was cooled to room temperature and diluted with EtOAc. The organic layer was washed with water, dried (MgSO$_4$) and concentrated. Purification by flash column chromatography using the Biotage system (20% EtOAc in hexanes) provided the desired product (55) (410 mg, 77%).

Step B: Preparation of 6-(2-chlorophenylamino)-7-fluoro-3-methylbenzo[c]-isoxazole-5-carboxylic acid (56): To a solution of 6-(2-chlorophenylamino)-7-fluoro-3-methyl-benzo[c]-isoxazole-5-carboxylic acid methyl ester (55) (100 mg, 0.299 mmol) in 6:1 THF:water (3.5 mL) was added LiOH (0.60 ml of a 1 M solution in water). After 1 hour, the reaction was acidified to pH 1 with 1 N HCl, diluted with water and extracted with EtOAc. The combined organic extracts were washed with water, dried (MgSO4) and concentrated to give the desired product (56) (87 mg, 91%). MS APCI (−) m/z 319, 321 (M+, Cl pattern) detected: $^1$H NMR (400 MHz, CD$_3$OD) δ 8.45 (s, 1H), 7.38 (dd, 1H), 7.20 (m, 1H), 6.91 (m, 2H), 2.88 (s, 3H): $^{19}$F NMR (376 MHz, CD$_3$OD) −136.40 (s, 1F).

Example 22

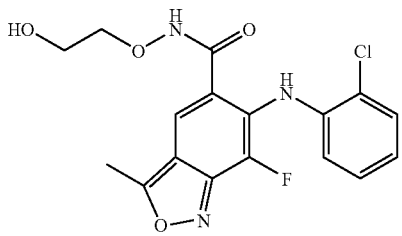

Synthesis of 6-(2-chlorophenylamino)-7-fluoro-3-methylbenzo[c]isoxazole-5-carboxylic acid (2-hydroxyethoxy)amide (57a)

Compound 57a was prepared as shown in FIG. 15 using 6-(2-chlorophenylamino)-7-fluoro-3-methylbenzo[c]isoxazole-5-carboxylic acid (56) to give 35 mg (44%) desired product. MS APCI (−) m/z 388, 390 (M+, Cl pattern) detected; $^1$H NMR (400 MHz, CD$_3$OD) δ 7.73 (s, 1H), 7.36 (d, 1H), 7.17 (t, 1H), 6.89 (t, 1H), 6.81 (dd, 1H), 3.72(d, 2H), 2.87 (s, 3H), 1.15 (m, 1H), 0.54 (d, 2H), 0.26 (d, 2H); 19F NMR (376 MHz, CD$_3$OD) −135.08 (s, 1F).

Example 23

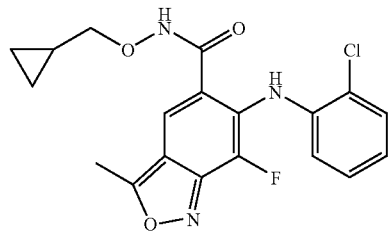

Synthesis of 6-(2-Chloro-phenylamino)-7-fluoro-3-methyl-benzo[c]isoxazole-5-carboxylic acid cyclopropylmethoxy-amide (57b)

Compound 57b was prepared as shown in FIG. 15 and described in Example 2 using 6-(2-chlorophenylamino)-7- fluoro-3-methylbenzo[c]isoxazole-5-carboxylic acid (56) to give 35 mg (44%) desired product. MS APCI (−) m/z 388, 390 (M+, Cl pattern) detected; ¹H NMR (400 MHz, CD₃OD) δ 7.73 (s, 1H), 7.36 (d, 1H), 7.17 (t, 1H), 6.89 (t, 1H), 6.81 (dd, 1H), 3.72(d, 2H), 2.87 (s, 3H), 1.15 (m, 1H), 0.54 (d, 2H), 0.26 (d, 2H); 19F NMR (376 MHz, CD₃OD) −135.08 (s, 1F).

Example 24

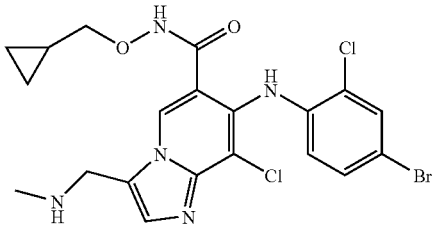

Synthesis of 7-(4-bromo-2-chlorophenylamino)-8-chloro-3-methylaminomethyl-imidazo[1,2-a]pyridine-6-carboxylic acid cyclopropylmethoxy-amide (63)

The synthesis of compound 63 is shown in FIG. 16.

Step A: Preparation of 7-(4-bromo-2-chlorophenylamino)-8-chloro-3-formyl-imidazo[1,2-a]pyridine-6-carboxylic acid methyl ester (58): A suspension of 6-amino-4-(4-bromo-2-chlorophenylamino)-5-chloro-nicotinic acid methyl ester (28) (1.06 g, 2.72 mmol) and 2-chloro-malonaldehyde (587 mg, 5.43 mmol) was heated to 80° C. for 45 minutes. The solution was allowed to cool to room temperature, and then washed with saturated aqueous NaHCO₃, and brine. The organic layer was dried over NaSO₄, filtered, concentrated in vacuo, and purified by column chromatography (20:1 methylene chloride/methanol) to give the desired product as a dark yellow solid. The solid was triturated with ethyl acetate and isolated by filtration to provide the desired product as a yellow solid (0.436 g, 36%). MS (APCI+) m/z 442, 444, 446 (M+; Cl, Br pattern) detected.

Step B: Preparation of 7-(4-bromo-2-chloro-phenylamino)-8-chloro-3-methylaminomethyl-imidazo[1,2-a]pyridine-6-carboxylic acid methyl ester (59): A suspension of 7-(4-bromo-2-chlorophenylamino)-8-chloro-3-formylimidazo[1,2-a]pyridine-6-carboxylic acid methyl ester (58) (25 mg, 0.056 mmol), acetic acid (7 μL, 0.11 mmol), and methylamine (2.0 M solution in THF, 56 μL, 0.11 mmol) was stirred for 0.5 hours. Sodium triacetoxyborohydride (36 mg, 0.17 mmol) was added and the solution allowed to stir overnight. The reaction mixture was concentrated to dryness and flashed (dichloromethane followed by 10:1 dichloromethane/methanol) to provide the desired product as a yellow solid (12 mg, 46%). MS (APCI+) m/z 455, 457, 459 (M+; Cl, Br pattern) detected.

Step C: Preparation of 7-(4-bromo-2-chlorophenylamino)-3-[(tert-butoxycarbonyl-methyl-amino)-methyl]-8-chlor-oimidazo[1,2-a]pyridine-6-carboxylic acid methyl ester (60): Di-tert-butyl dicarbonate (6 mg, 0.029 mmol) and triethylamine (4 μL, 0.029 mmol) were added to a solution of 7-(4-bromo-2-chlorophenylamino)-8-chloro-3-methyaminomethylimidazo[1,2-a]pyridine-6-carboxylic acid methyl ester (59) (12 mg, 0.026 mmol) in dichloromethane. The solution was stirred at room temperature for 0.5 hr after which time HPLC analysis indicated the reaction had gone to completion. The solution was rotovapped to dryness to provide the desired product as a yellow foam (15 mg, quantitative). MS (APCI+) m/z 557, 559, 561 (M+; Cl, Br pattern) detected.

Step D: Preparation of 7-(4-bromo-2-chlorophenylamino)-3-[(tert-butoxycarbonyl-methylamino)-methyl]-8-chloroimidazo[1,2-a]pyridine-6-carboxylic acid (61): Sodium hydroxide (1.0 M aqueous solution, 0.16 mL, 0.16 mmol) is added to a solution of 7-(4-bromo-2-chlorophenylamino)-3-[(tert-butoxycarbonylmethylamino)-methyl]-8-chloroimidazo[1,2-a]pyridine-6-carboxylic acid methyl ester (60) (15 mg, 0.026 mmol) in 4:1 MeOH/water (5 mL). When the reaction was complete, the solution was diluted with water, acidified to pH 3 by addition of 1.0 M aqueous HCl, and extracted with ethyl acetate. The organic extracts were dried over NaSO₄, filtered, concentrated in vacuo to provide the desired product as a white crystalline solid (12 mg, 84%). MS (APCI-) m/z 541, 543, 545 (M−; Cl, Br pattern) detected.

Step E: Preparation of [7-(4-bromo-2-chlorophenylamino)-8-chloro-6-cyclopropylmethoxycarbamoylimidazo[1,2-a]pyridin-3-ylmethyl]-methylcarbamic acid tert-butyl ester (62): EDCl (6 mg, 0.033 mmol) and HOBt (5 mg, 0.033 mmol) were added to a solution of 7-(4-bromo-2-chlorophenylamino)-3-[(tert-butoxycarbonylmethylamino)-methyl]-8-chloro-imidazo[1,2-a]pyridine-6-carboxylic acid (61) in dimethylacetamide (0.4 mL). The yellow solution was allowed to stir at room temperature for 0.5 hours after which time O-cyclopropylmethyl-hydroxylamine (6 mg, 0.066 mmol) and triethylamine (6 μL, 0.044 mmol) were added and the solution allowed to stir overnight. The reaction mixture was diluted with ethyl acetate, washed with water, saturated aqueous ammonium chloride, saturated aqueous potassium carbonate and brine. The organic phase was dried over NaSO₄, filtered, concentrated in vacuo to provide the desired product as a yellow residue (11.5 mg, 85%). MS (APCI+) m/z 612, 614, 616 (M+; Cl, Br pattern) detected.

Step F: Preparation of 7-(4-bromo-2-chlorophenylamino)-8-chloro-3-methylaminomethylimidazo[1,2-a]pyridine-6-carboxylic acid cyclopropylmethoxyamide (63): A solution of [7-(4-bromo-2-chlorophenylamino)-8-chloro-6-cyclopropylmethoxy-carbamoyl-imidazo[1,2-a]pyridin-3-ylmethyl]-methyl-carbamic acid tert-butyl ester (62) in 1:1 dichloromethane/trifluoroacetic acid was stirred for two hours. Solvent was removed under reduced pressure and the residue redissolved into ethyl acetate. The organic solution was washed with saturated aqueous potassium carbonate and brine. The aqueous washes were back-extracted with ethyl acetate. The combined organic extracts are dried over NaSO₄, filtered, and concentrated in vacuo to provide the desired product as a yellow solid (8 mg, 83%). MS (APCI+) m/z 512, 514, 516 (M+; Cl, Br pattern) detected. ¹H NMR (400 MHz, methanol-d₄) δ 8.72 (s, 1H), 7.58 (s, 1H), 7.54 (s, 1H), 7.25 (d, 1H), 6.55 (d, 1H), 4.23 (s, 2H), 3.67 (d, 2H), 2.51 (s, 3H), 1.13 (m, 1H), 0.50 (d, 2H), 0.24 (d, 2H).

Example 25

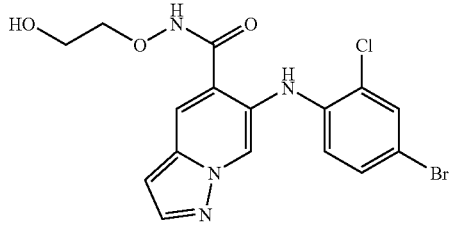

Synthesis of 6-(4-bromo-2-chlorophenylamino)-pyrazolo[1,5-a]pyridine-5-carboxylic acid (2-hydroxyethoxy)amide (73a)

Compound 73a, where W═Br, Y═Cl, and X═H, can be prepared as shown in FIG. 17.

Example 26

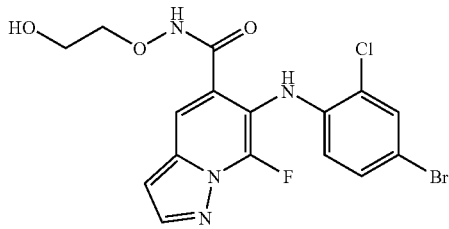

Synthesis of 6-(4-bromo-2-chlorophenylamino)-7-fluoropyrazolo[1,5-a]pyridine-5-carboxylic acid (2-hydroxyethoxy)-amide (73b)

Compound 73b, where W=Br, Y=Cl, and X=F, can be prepared as shown in FIG. 17.

Example 27

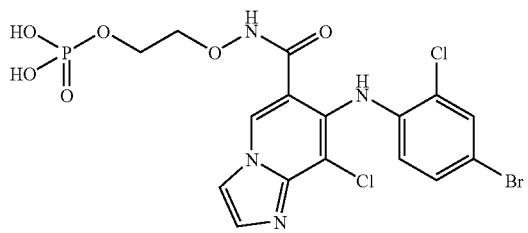

Synthesis of phosphoric acid mono-(2-{[7-(4-bromo-2-chloro-phenylamino)-8-chloro-imidazo[1,2-a]pyridine-6-carbonyl]-aminooxy}-ethyl) ester (74)

The synthesis of compound 74 is shown in FIG. 18. 7-(4-bromo-2-chlorophenylamino)-8-chloroimidazo[1,2-a]pyridine-6-carboxylic acid (2-hydroxyethoxy)-amide (33a) (100 mg, 0.234 mmol), tetrazole (23 mg, 0.327 mmol) and di-tert-butyl diisopropylphosphoramidite (0.096 mL, 0.304 mmol) were dissolved/suspended in 30 mL of anhydrous DMF under an atmosphere of dry $N_2$. The reaction mixture was stirred for about 3 hours, after which time the reaction was cooled to −78° C. and tert-butyl hydrogen peroxide (0.100 mL of 70% solution in water) was added. The cooling bath was then taken away and the reaction was slowly warmed up to room temperature and reacted over night. The reaction mixture was then partitioned between a solution of ethyl ether/ethyl acetate (5:1) and saturated aqueous $NaHCO_3$. The organic layer was saved and successively washed with 10% aqueous sodium sulfite, 3 times with water and finally with brine. The resulting organic layer was dried over $MgSO_4$, filtered and concentrated under vacuum. The residue was dissolved in 3 mL of a solution of TFA/DCM (2:1) under an atmosphere of dry $N_2$. The reaction was stirred at room temperature for about 2 hours after which time it was concentrated under vacuum and the resulting residue was stirred in methanol for about 1 hour. The off-white solid was collected via suction filtration, washed with methanol followed by ethyl ether and then air-dried to give the desired compound (74).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound of the Formula III

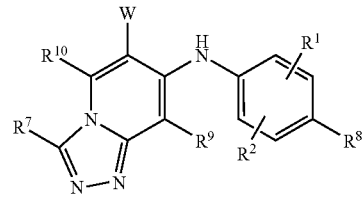

and solvates and pharmaceutically acceptable salts thereof, wherein:

$R^1, R^2, R^7, R^8, R^9$, and $R^{10}$ are independently selected from hydrogen, halogen, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$ ($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl and —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO$_2$R''', —SO$_2$NR'R'', —C(O)R', —C(O)OR', —OC(O)R', —NR'C(O)OR''', —NR'C(O)R'', —C(O)NR'R'', —SR', —S(O)R''', —SO$_2$R''', —NR'R''', —NR'C(O)NR''R''', —NR'C(NCN)NR''R''',
—OR', aryl, heteroaryl, arylalkyl, heteroarylalkyl, heterocyclyl, and heterocyclylalkyl, or $R^3$ and $R^4$ together with the atom to which they are attached form a 4 to 10 membered saturated, unsaturated, or partially saturated heterocyclic ring, wherein any of said saturated, unsaturated, or partially saturated heterocyclic rings are optionally substituted with one or more groups independently selected from halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R', R'' and R''' are independently hydrogen, lower alkyl, lower alkenyl, aryl or arylalkyl, R'''' is lower alkyl, lower alkenyl, aryl or arylalkyl, or any two of R', R'', R''' or R'''' together with the atom to which they are attached form a 4 to 10 membered saturated, unsaturated, or partially saturated heterocyclic ring, wherein any of said alkyl, alkenyl, aryl, arylalkyl saturated, unsaturated, and partially saturated heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^4$ and $R^5$ are independently hydrogen or $C_1$-$C_6$ alkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl, or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halogen, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R', —NR'C(O)NR''R''', —NR'C(NCN)N''R''', —OR', aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), and CR$^3$OR$^3$ are optionally substituted with one or more groups independently selected from —NR$^3$R$^4$, —OR$^3$, —R$^2$, C$_1$-C$_{10}$ alkyl, C$_2$-C$_{10}$ alkenyl, and C$_2$-C$_{10}$ alkynyl, wherein any of said C$_1$-C$_{10}$ alkyl, C$_2$-C$_{10}$ alkenyl, and C$_2$-C$_{10}$ alkynyl are optionally substituted with 1 or more groups independently selected from —NR$^3$R$^4$ and —OR$^3$;

m is 0, 1, 2, 3, 4 or 5; and j is 1 or 2.

2. The compound of claim 1, wherein $R^1$ is halogen.

3. The compound of claim 2, where $R^1$ is Cl.

4. The compound of claim 1, wherein $R^7$ is alkyl or arylalkyl.

5. The compound of claim 4, where $R^7$ is methyl or benzyl.

6. The compound of claim 1, wherein $R^8$ is halogen.

7. The compound of claim 6, where $R^8$ is Br.

8. The compound of claim 1, wherein $R^9$ is halogen.

9. The compound of claim 8, where $R^9$ is Cl.

10. The compound of claim 1, wherein W is —C(O)NR$^4$OR$^3$.

11. The compound of claim 10, where W is —C(O)NHOCH$_2$-(cyclopropyl) or —C(O)NHO(CH$_2$)$_2$OH.

12. The compound of claim 1, having the formula

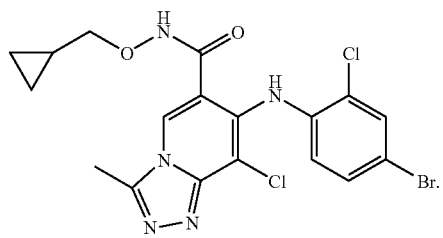

13. The compound of claim 1, having the formula

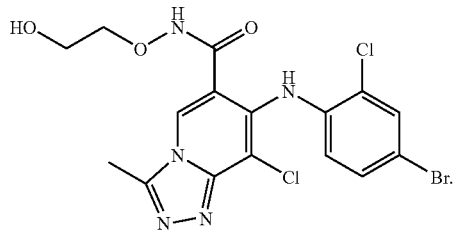

14. The compound of claim 1, having the formula

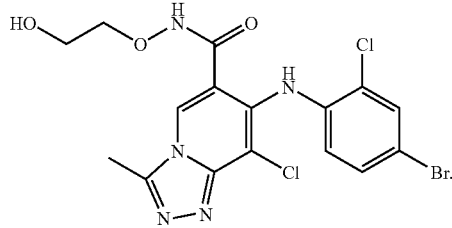

15. A composition comprising a compound of claim 1 or a pharmaceutically acceptable salt thereof and a pharmaceutically acceptable carrier.

16. The compound of claim 1, wherein $R^3$ is an amino acid residue.

17. The compound of claim 16, wherein the amino acid residue is valine.

18. The compound of claim 1, wherein $R^3$ is a phosphate.

* * * * *